(12) United States Patent
Miller

(10) Patent No.: US 10,278,816 B2
(45) Date of Patent: May 7, 2019

(54) CATHETER ASSEMBLY WITH PROSTHESIS CRIMPING AND PROSTHESIS RETAINING ACCESSORIES

(71) Applicant: Medtronic Vascular Galway, Ballybrit, Galway (IE)

(72) Inventor: Noam Miller, Netanya (IL)

(73) Assignee: Medtronic Vascular Galway, Galway (IE)

( * ) Notice: Subject to any disclaimer, the term of this patent is extended or adjusted under 35 U.S.C. 154(b) by 176 days.

(21) Appl. No.: 15/182,419

(22) Filed: Jun. 14, 2016

(65) Prior Publication Data
US 2016/0361166 A1 Dec. 15, 2016

Related U.S. Application Data

(63) Continuation of application No. 13/114,826, filed on May 24, 2011, now Pat. No. 9,387,077.
(Continued)

(51) Int. Cl.
*A61F 2/24* (2006.01)
*A61F 2/95* (2013.01)
*A61F 2/966* (2013.01)

(52) U.S. Cl.
CPC .......... *A61F 2/2436* (2013.01); *A61F 2/2418* (2013.01); *A61F 2/95* (2013.01);
(Continued)

(58) Field of Classification Search
CPC .. A61F 2/2436; A61F 2/95; A61F 2002/9522; A61F 2/2412; A61F 2/2418;
(Continued)

(56) References Cited

U.S. PATENT DOCUMENTS 3,657,744 A 4/1972 Ersek
5,350,397 A 9/1994 Palermo et al.
(Continued)

FOREIGN PATENT DOCUMENTS

EP 0903122 3/1999
EP 2208483 7/2010
(Continued)

OTHER PUBLICATIONS

EP Application No. 16201170.4-1651, Extended European Search Report, dated Mar. 6, 2017, 7pgs.

*Primary Examiner* — Amy R Weisberg
(74) *Attorney, Agent, or Firm* — Medler Ferro Woodhouse & Mills PLLC

(57) ABSTRACT

A prosthesis retaining assembly for securing an implantable prosthesis to a catheter assembly can include a first member including a prosthesis retaining slot configured to retain a portion of the prosthesis. The retaining slot can have a first portion with a first width and a second portion with a second width. The first portion can be distal to the second portion. The second width can be larger than the first width, and the retaining slot can have an opening at a first surface of the first member. The prosthesis retaining assembly can also include a second member configured to be move relative to the first member. The second member can be configured to move to a position that obstructs a portion of the opening of the retaining slot.

13 Claims, 54 Drawing Sheets

Related U.S. Application Data

(60) Provisional application No. 61/348,760, filed on May 27, 2010.

(52) U.S. Cl.
CPC ..... *A61F 2/2412* (2013.01); *A61F 2002/9522* (2013.01); *A61F 2002/9665* (2013.01)

(58) Field of Classification Search
CPC ...... A61F 2002/9665; A61F 2002/9505; A61F 2002/9511; A61F 2002/9517; A61F 2002/9528; A61F 2002/9534; A61F 2/954; A61F 2/958; A61F 2002/9583; A61F 2002/9586; A61F 2/962; A61F 2/966; A61F 2/97
USPC ............... 606/108, 200; 623/1.11–1.35, 2.11
See application file for complete search history.

(56) References Cited

U.S. PATENT DOCUMENTS

| | | | |
|---|---|---|---|
| 5,370,685 A | 12/1994 | Stevens | |
| 5,545,214 A | 8/1996 | Stevens | |
| 5,733,325 A | 3/1998 | Robinson et al. | |
| 5,814,097 A | 9/1998 | Sterman et al. | |
| 5,817,104 A * | 10/1998 | Bilitz | A61B 17/221 606/127 |
| 6,077,297 A | 6/2000 | Robinson et al. | |
| 6,214,036 B1 * | 4/2001 | Letendre | A61F 2/07 623/1.11 |
| 6,814,746 B2 | 11/2004 | Thompson et al. | |
| 6,830,584 B1 | 12/2004 | Seguin | |
| 6,936,058 B2 * | 8/2005 | Forde | A61F 2/01 606/108 |
| 7,175,654 B2 | 2/2007 | Bonsignore et al. | |
| 7,235,093 B2 | 6/2007 | Gregorich | |
| 7,771,463 B2 | 8/2010 | Ton et al. | |
| 7,927,362 B2 | 4/2011 | Shippy et al. | |
| 8,066,755 B2 | 11/2011 | Zacharias et al. | |
| 8,236,040 B2 | 8/2012 | Mayberry et al. | |
| 8,414,644 B2 | 4/2013 | Quadri et al. | |
| 8,562,668 B2 | 10/2013 | Ma et al. | |
| 8,568,472 B2 | 10/2013 | Marchand et al. | |
| 8,652,192 B2 | 2/2014 | St. Germain et al. | |
| 8,882,828 B2 | 11/2014 | Kinkade et al. | |
| 9,414,914 B2 | 8/2016 | Duffy et al. | |
| 2002/0016598 A1 | 2/2002 | Kurz | |
| 2002/0055767 A1 | 5/2002 | Forde et al. | |
| 2002/0120323 A1 | 8/2002 | Thompson et al. | |
| 2003/0225445 A1 | 12/2003 | Derus et al. | |
| 2004/0093063 A1 | 5/2004 | Wright et al. | |
| 2004/0148008 A1 | 7/2004 | Goodson et al. | |
| 2004/0254627 A1 | 12/2004 | Thompson et al. | |
| 2005/0113864 A1 | 5/2005 | Gandshi et al. | |
| 2006/0004434 A1 | 1/2006 | Forde et al. | |
| 2006/0111771 A1 * | 5/2006 | Ton | A61F 2/88 623/1.15 |
| 2006/0241682 A1 * | 10/2006 | Kurz | A61B 17/12022 606/200 |
| 2006/0259120 A1 | 11/2006 | Vongphakdy et al. | |
| 2006/0286145 A1 * | 12/2006 | Horan | A61F 2/95 424/426 |
| 2008/0004688 A1 | 1/2008 | Spenser et al. | |
| 2008/0125848 A1 | 5/2008 | Kusleika et al. | |
| 2008/0140178 A1 | 6/2008 | Rasmussen et al. | |
| 2008/0234797 A1 | 9/2008 | Styrc | |
| 2008/0262590 A1 | 10/2008 | Murray | |
| 2008/0264102 A1 | 10/2008 | Berra | |
| 2009/0234279 A1 | 9/2009 | Goldstein | |
| 2009/0287290 A1 | 11/2009 | Macaulay et al. | |
| 2009/0319037 A1 | 12/2009 | Rowe et al. | |
| 2010/0049313 A1 * | 2/2010 | Alon | A61F 2/2418 623/2.11 |
| 2010/0057185 A1 | 3/2010 | Melsheimer et al. | |
| 2010/0121424 A1 | 5/2010 | Kubena et al. | |
| 2010/0324647 A1 | 12/2010 | Rincon | |
| 2012/0022633 A1 | 1/2012 | Olson et al. | |
| 2012/0078350 A1 * | 3/2012 | Wang | A61F 2/2436 623/2.11 |
| 2012/0239142 A1 * | 9/2012 | Liu | A61F 2/0095 623/2.11 |
| 2013/0085562 A1 | 4/2013 | Rincon et al. | |
| 2013/0172977 A1 | 7/2013 | Forde et al. | |
| 2013/0289698 A1 * | 10/2013 | Wang | A61F 2/2436 623/1.12 |
| 2014/0207175 A1 | 7/2014 | Aggerholm | |
| 2014/0222059 A1 * | 8/2014 | Leopold | A61B 17/12145 606/200 |
| 2014/0257369 A1 * | 9/2014 | Leopold | A61B 17/12145 606/200 |

FOREIGN PATENT DOCUMENTS

| | | |
|---|---|---|
| FR | 9914462 | 11/1999 |
| WO | WO93/01768 | 2/1993 |
| WO | WO97/28807 | 8/1997 |
| WO | WO06/026371 | 3/2006 |
| WO | WO2007/134290 | 11/2007 |
| WO | WO09/111241 | 9/2009 |
| WO | WO2009/149457 | 12/2009 |
| WO | WO2010/030766 | 3/2010 |

* cited by examiner

CATHETER ASSEMBLY WITH PROSTHESIS CRIMPING AND PROSTHESIS RETAINING ACCESSORIES

CROSS-REFERENCE TO RELATED APPLICATION

This application is a Continuation of and claims the benefit of U.S. patent application Ser. No. 13/114,826, filed May 24, 2011, now allowed, which claims the benefit of U.S. Provisional Application No. 61/348,760 to Miller, filed May 27, 2010, the entire disclosures of which are incorporated by reference in their entirety herein.

BACKGROUND OF THE INVENTION

Field of the Invention

The present invention relates to catheter assemblies, crimping accessories, prosthesis retaining accessories and methods of crimping prostheses onto a catheter and retaining the prostheses on a catheter during delivery to a desired body location. More specifically, the present invention provides for catheters, crimping accessories, and retaining accessories that simplify the process of crimping a prosthetic valve to a catheter.

Background

Recently, minimally invasive approaches have been developed to facilitate catheter-based implantation of valve prostheses on the beating heart, intending to obviate the need for the use of classical sternotomy and cardiopulmonary bypass. For example, French Patent Application No. 99 14462 illustrates a technique and a device for the ablation of a deficient heart valve by percutaneous route, with a peripheral valvular approach. International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques that are not very invasive as well as instruments for implementation of these techniques.

With regard to the positioning of a replacement heart valve, attaching a valve on a support with a structure in the form of a wire or network of wires, forming a frame, has been proposed. This frame can be contracted radially in such a way that it can be introduced into the body of the patient percutaneously by means of a catheter, and it can be deployed so as to be radially expanded once it is positioned at the desired target site. U.S. Pat. No. 3,657,744 to Ersek discloses a cylindrical, frame-supported, tri-leaflet tissue heart valve that can be delivered through a portion of the vasculature using an elongate tool. The frame is mounted onto the expansion tool prior to delivery to the target location where the frame and valve are expanded into place.

Current techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter is transcatheterally advanced toward the native valve, where it is either forcefully deployed using a balloon catheter, or, alternatively, passively deployed using a self-expandable system. Accurate positioning of the replacement valve in the native annulus is critical to the success of the implantation.

In order to prepare such valve prostheses for implantation, the valve prosthesis can be initially provided in an expanded or uncrimped condition, then crimped or compressed around the catheter until it is as close to the diameter of the catheter as possible. Various methods and devices are available for crimping the valve onto the catheter, which may include hand-held devices or tabletop devices, for example. These crimping devices can initially provide an opening that is large enough to accommodate a valve in its expanded condition and positioned over a desired section of a catheter. This valve can then be compressed by reconfiguring the opening of the crimping device in some way to uniformly decrease the size of the opening until the valve is compressed to a desired size. However, crimping a prosthetic valve using known hand held or tabletop devices requires a user to assemble and position the crimping device over a separately acquired catheter, resulting in the possibility of user error. In addition, positioning a crimping device over a catheter assembly can be complicated, for example, where the catheter assembly has a distal tip with a diameter larger than the final crimped diameter of the valve. In such situations, the known crimping devices are difficult to position on and remove from the catheter body.

The present invention provides a catheter assembly and crimping accessories for crimping a valve onto the catheter assembly. Crimping accessories according to the present invention can be provided pre-loaded onto a catheter assembly, and can be easily removed from the catheter assembly after a prosthetic valve has been crimped onto the catheter assembly, particularly with reference to catheter assemblies with enlarged distal tips. The crimping accessories described herein can also be provided separately from a catheter assembly and later positioned over the catheter. The catheter assemblies and associated crimping accessories described herein simplify the process of crimping a prosthetic valve and improve the accuracy of positioning the prosthetic valve within a body channel.

BRIEF SUMMARY OF THE INVENTION

The catheter assemblies and crimping accessories and methods described herein seek to remedy one or more of the disadvantages of previous crimping methods by providing catheters and crimping accessories that simplify the process of crimping a prosthetic valve or stent to a catheter. The crimping accessories and methods described herein are particularly useful for crimping a prosthetic valve onto a catheter having a distal tip with a diameter larger than the final crimped diameter of the prosthetic valve. In one embodiment of the present invention, a catheter assembly includes a handle assembly located on the proximal end of the catheter assembly and a distal tip assembly located on the distal end of the catheter assembly. A crimping funnel is slidably positioned along the catheter. The crimping funnel includes a distal end having a first diameter and a proximal end having a second diameter smaller than the first diameter. An axial split is formed in the proximal end. A first collar is provided encompassing a portion of the proximal end. The first collar is configured to hold the axial split in the proximal end together when the first collar is at a first axial location along the proximal end, and to allow the axial split in the proximal end to open when the first collar is at a second axial location along the proximal end, such that the crimping funnel can be removed from the catheter assembly. Various prosthesis retaining assemblies to securely retain a prosthesis to a catheter assembly during delivery of the prosthesis to a desired body location are described herein.

BRIEF DESCRIPTION OF THE FIGURES

The accompanying figures, which are incorporated herein, form part of the specification and illustrate embodiments of crimpers for prosthetic valves and methods of crimping and retaining prosthetic valves and other prostheses for transcatheter delivery. Together with the description, the figures further serve to explain the principles of and to enable a person skilled in the relevant art(s) to make and use the prosthetic valve crimpers and methods of crimping prosthetic valves for transcatheter delivery described herein. In the drawings, like reference numbers indicate identical or functionally similar elements.

DETAILED DESCRIPTION OF THE INVENTION

The following detailed description of crimpers and retainers for prostheses and methods of crimping and retaining prostheses for transcatheter delivery refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, while the description provided is directed to accessories for crimping and loading a prosthetic heart valve onto a catheter, the crimping and retaining accessories described herein should not be limited to crimping and retaining of a prosthetic valve. One of skill in the art would readily understand how to incorporate the features and structures described herein into crimping and retaining accessories for other purposes. For example, features of the crimping and retaining accessories described herein can be incorporated into catheters intended for other types of procedures, such as delivery of other implantable prostheses such as stents, valves, or other prostheses to a variety of areas in the body.

Figure 1:
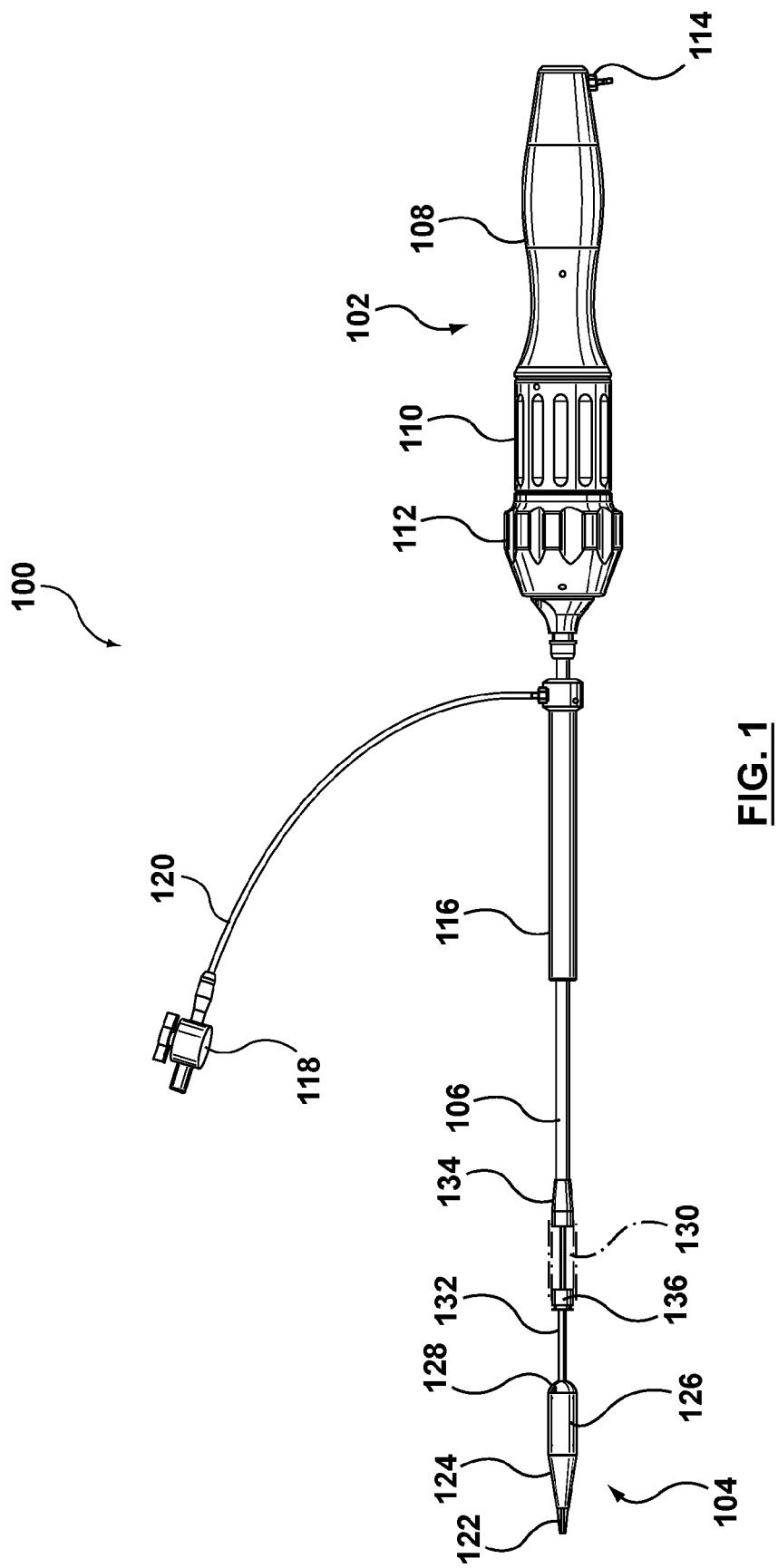
FIG. 1 illustrates a catheter assembly in accordance with one embodiment presented herein.

FIG. 1 illustrates a catheter assembly 100 in accordance with one embodiment presented herein. Catheter assembly 100 is depicted in FIG. 1 in a closed configuration. Catheter assembly 100 generally includes a handle assembly 102 located at the proximal end of the catheter, a distal tip assembly 104 located at the distal end of the catheter, and an introducer 116 slidably located along an outer delivery shaft 106 between the distal tip assembly 104 and the handle assembly 102.

Outer delivery shaft 106 is preferably a tubular flexible braided structure. Outer delivery shaft 106 can be formed of braided material fabricated from materials such as, but not limited to, polyethylene naphthalate (PEN), polyester (PET), stainless steel, titanium, nitinol, cobalt nickel alloy, polyamide, polyimide, or the like. In some embodiments, outer delivery shaft may contain reinforcing materials or structures. These structures can include an inner layer of polymer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of a polymeric material. In other embodiments, the inner layer of polymeric material is overlaid by a braided layer, which is overlaid by the coil winding, which is overlaid by another layer of braid, which is in turn overlaid by an outer polymeric layer. Preferably, however, any reinforcing layer used allows outer delivery shaft 106 to retain a degree of flexibility. Other suitable flexible materials can also be used to form outer delivery shaft 106 consistent with embodiments of the present invention.

Handle assembly 102 includes a main handle 108, a proximal control knob 110, and a distal control knob 112. Main handle 108, a proximal control knob 110, and distal control knob 112 can be formed of any suitable material. For example, in some embodiments the handle and control knobs are formed of a polymer material. Other materials are possible, as would be understood in the art. A flushing port 114 can also be included on main handle 108. Flushing port 114 can be used to de-air the catheter assembly. Also, the native annulus is exposed to the blood pressure in a patient's cardiovascular system during use of a heart valve delivery catheter. As a consequence, in the absence of any counter pressure in this annulus, blood can flow inside towards the proximal end of the catheter, where it may coagulate and cause thrombosis. Thus, flushing port 114 can also allow fluid to be introduced into the native annulus to prevent such complications. In some embodiments, flush port 114 can also be used for site specific drug delivery or to introduce radiopaque fluid into the body.

As will be described herein, proximal control knob 110, and distal control knob 112 can be manipulated by a user in order to control operation of the distal tip assembly 104 of catheters described herein. Distal tip assembly 104 includes a tip 122, which is preferably slotted for the reasons described herein, a tip connector 124, and a support arm sleeve 126. Support arm sleeve 126 defines an annular chamber. A flushing tap 118 and a flushing tap lead 120 can be connected to an introducer 116. Introducer 116 is preferably a tubular member that is slidably located over outer delivery shaft 106. Introducer 116 may be formed of a variety of materials, for example, stainless steel or various polymer materials. Catheter 100 is configured to be advanced along a guide wire (not shown). Preferably, the catheter is advanced over a 0.035 inch guide wire. However, the dimensions of the catheter components can be adjusted for advancement over guide wires with larger or smaller diameters.

Catheter assembly 100 further includes a valve retaining sleeve 130, a valve retaining sleeve connector 134, a valve retainer 132, and a tip guard 128. Valve retaining sleeve connector 134 secures valve retaining sleeve 130 to the distal end of the outer delivery shaft 106. The outer delivery shaft 106 therefore extends from the interior of handle assembly 102 to sleeve connector 134. Slotted tip 122 and tip guard 128 are positioned on and connected to the distal end of an intermediate delivery shaft 132. Intermediate delivery shaft 132 extends from the interior of handle assembly 102 to slotted tip 122, to which the distal end of intermediate delivery shaft 132 is attached. Intermediate delivery shaft 132 is encompassed by outer delivery shaft 106 from the interior of handle assembly 102 until the outer delivery shaft 106 ends at sleeve connector 134. Tip guard 128 is attached to the proximal end of slotted tip 122. In one embodiment, tip guard 128 can be attached directly to intermediate shaft 132. Intermediate shaft 132 is preferably a tubular member.

It is understood that handle assembly 102 is merely an exemplary embodiment of a catheter handle that can be used in conjunction with the crimping devices and method described herein. The present invention is not limited to catheters having handles such as those described herein. The crimping devices and methods described herein can be used with catheter having different types of handles, including, e.g., conventional hand controlled catheter handles. It is further understood that other devices described with reference to FIG. 1, but not essential to the crimping devices and methods of the present invention, are optional and can be replaced with similar devices or can be left out entirely if not necessary for a particular application. For example, depending on the delivery method, catheters assemblies for use with the crimping devices and methods described herein can be provided without an introducer.

A guide wire shaft is encompassed within intermediate shaft 132 and extends from the inside of handle assembly 102 to the proximal end of slotted tip 122. Thus, in one embodiment of the present invention, at least three shafts extend from the main handle, and the shafts are nested along at least a part of their lengths. Specifically, guide wire shaft 504 is encompassed by the intermediate delivery shaft 132 from a position inside of handle assembly 102 to the interior of slotted tip 122, which is preferably hollow through at least a portion thereof. Intermediate delivery shaft 132 is connected to, and ends at, the proximal end of slotted tip 122. In turn, intermediate delivery shaft 132 is encompassed by the outer delivery shaft 106 from a position inside of handle assembly 102 to the valve retaining sleeve connector 134. Outer delivery shaft 106 is connected to, and ends at, the retaining sleeve connector 134. Intermediate shaft 132 and guide wire shaft can be constructed of various polymer materials, and may be braided structures using materials described above with reference to outer delivery shaft 106.

Figure 2:
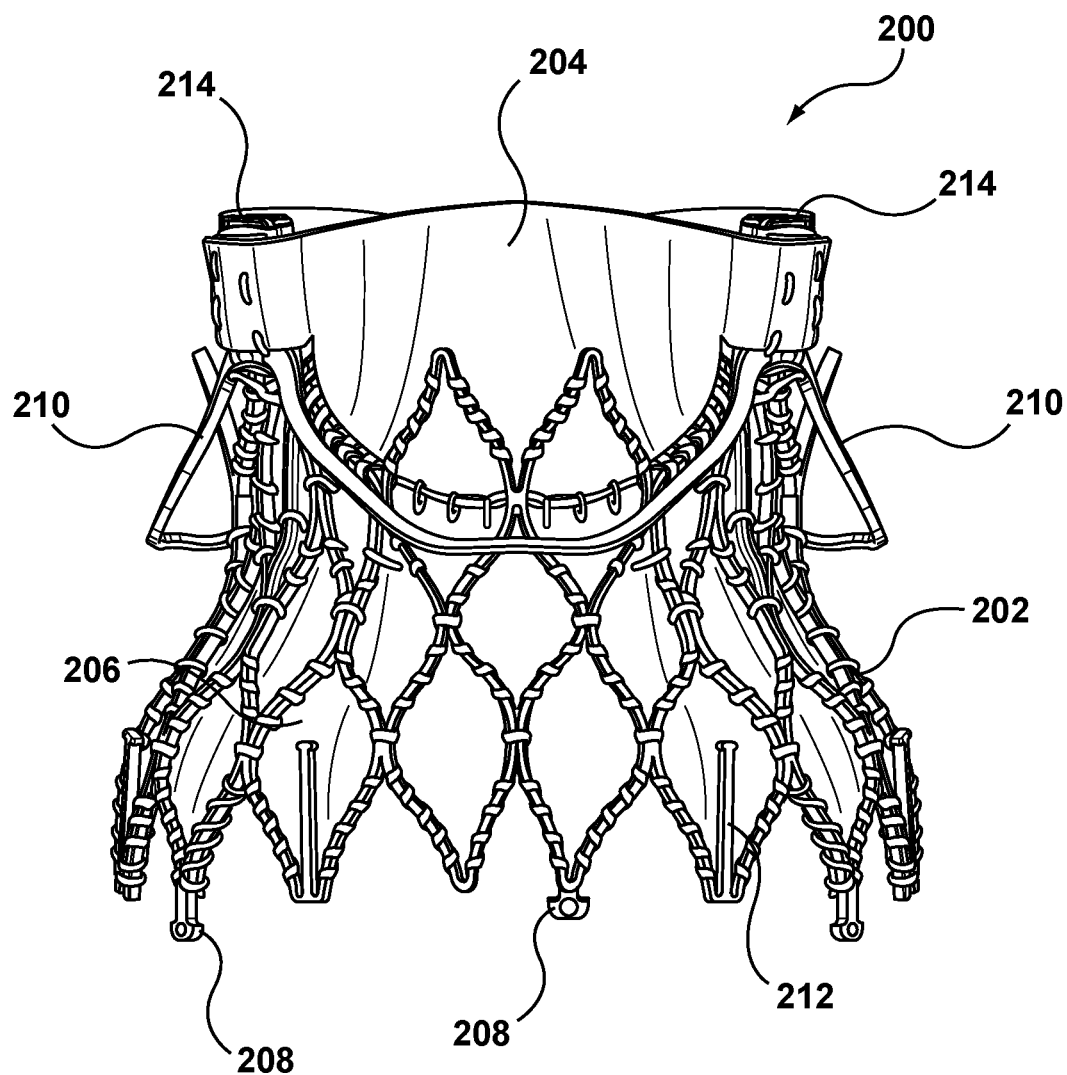
FIG. 2 is a depiction of one of the many types of prosthetic valves that are compatible with the valve crimping accessories described herein. The exemplary prosthetic valve is shown herein to facilitate explanation of the structure and operation of the crimping accessories and methods described herein.

FIG. 2 depicts an exemplary prosthetic heart valve 200. Heart valve 200 is illustrated herein in order to facilitate description of the crimping accessories according to embodiments of the present invention. It is understood that any number of alternate prosthetic heart valves can be used with the crimping accessories described herein. Prosthetic heart valve 200 is merely exemplary. Prosthetic heart valve 200 includes support frame 202, valve leaflets 204 located towards the distal end of support frame 202, valve skirt 206, and three fixation hooks 208 extending from the proximal end of valve support 208.

Support frame 202 is preferably formed of a self-expanding material, e.g., nitinol. Other self-expanding or shape memory materials can be used instead of nitinol. Preferably, three valve leaflets 204 are provided to form a tricuspid valve structure within prosthetic heart valve 200. It is understood that alternate valve leaflet configurations, e.g., bicuspid valves, can be included in prosthetic heart valves for use in conjunction with the crimping devices and methods described herein. Leaflets 204 and skirt 206 are preferably formed of animal pericardium tissue, e.g., bovine pericardium or porcine pericardium. In other embodiments, leaflets 204 and skirt 206 can be formed from synthetic materials. Leaflets 204 and skirt 206 are attached to support frame 202, preferably using sutures, as shown in FIG. 2. It is understood that various types of sutureless bonding methods can be used to attach leaflets 204 and skirt 206 to frame 202. Fixation hooks 208 extend from the proximal end of support frame 202 and include eyelets at their proximal end. Fixation hooks 208, which are optional, can be formed in various configurations other than that shown. For example, fixation hooks 208 can be J shaped hooks or eyelets, and fixation hooks 208 can take on any number of sizes or shapes while remaining compatible with the crimping devices and methods described herein. Support frame 202 further includes three support arms 210, which are attached to support frame 202 towards its distal end. Alternately, support arms 210 can be formed integrally with support frame 202. Support arms 202 are preferably formed of a self-expanding material, e.g., nitinol. Other self-expanding or shape memory materials can be used instead of nitinol. Support arms 202 can be attached to support frame 202 such that they are biased away from support frame 202 but can pivot radially with respect to support frame 202. A plurality of barbs 212 can be provided on the proximal end of support frame 202. Barbs 212 extend for a distance towards the distal end of support frame 202. Preferably, barbs 212 extend in an approximately axial direction. Barbs 212, which are optional, can also be biased or curved slightly inward, but with less inward curve than the surrounding section of support frame 202. Because the distal end of barbs 212 define a greater diameter than the surrounding support frame, they receive the majority of forces when the proximal end of support frame 202 is crimped using the techniques described herein. This prevents damage to support frame 202 and, more particularly, to the sutures attaching skirt 206 to support frame 202.

Figure 3:
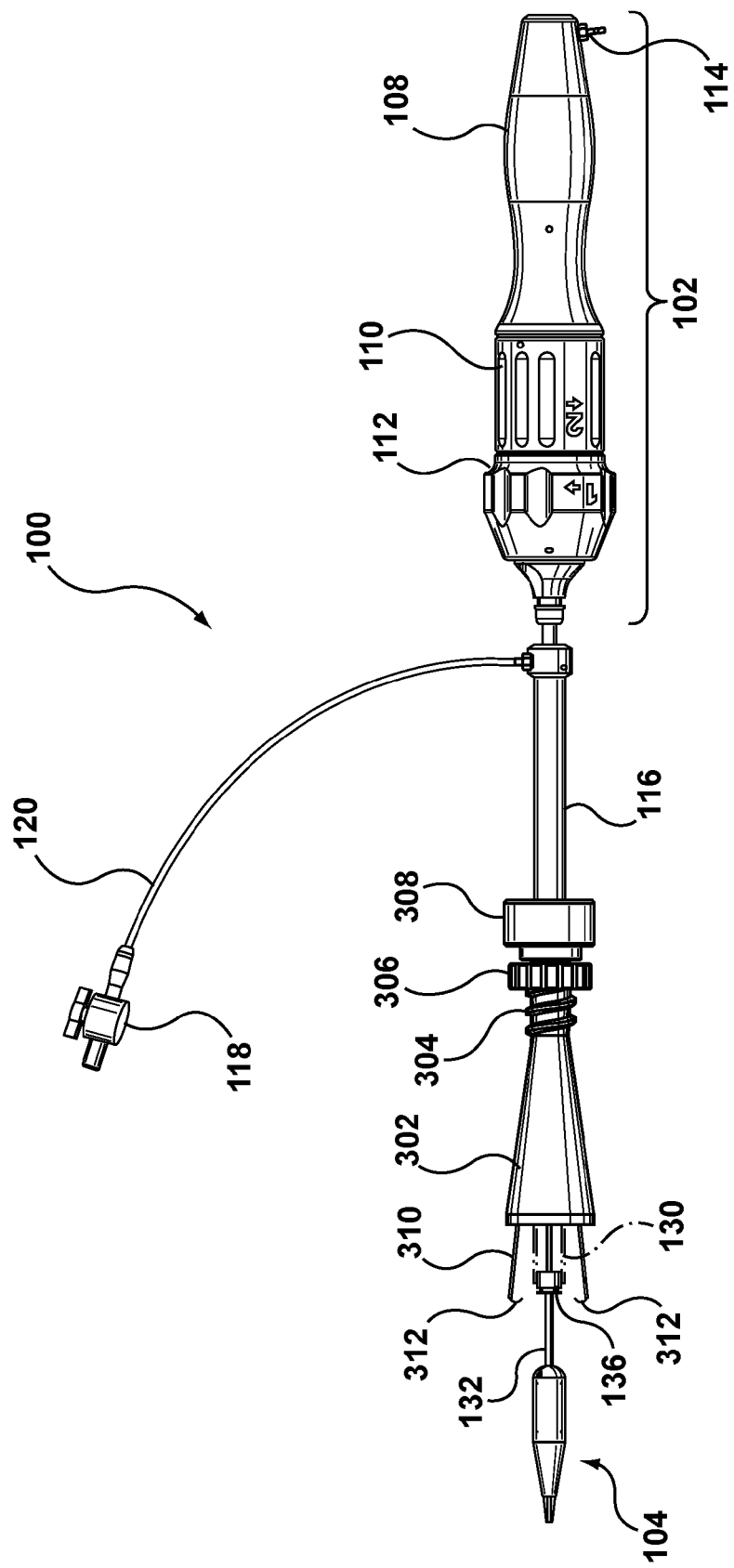
FIG. 3 illustrates the catheter assembly of FIG. 1 including accessories for crimping a prosthetic valve onto the catheter assembly.

FIG. 3 illustrates the catheter assembly 100 as shown in FIG. 1, further including accessories for crimping a prosthetic heart valve onto the catheter assembly. Specifically, FIG. 3 depicts catheter assembly 100 with a crimping funnel 302 loaded thereon. Crimping funnel 302 has a split proximal end 304. A funnel collar 306 is threaded around split proximal end 304 in order to hold split proximal end 304 together during the crimping process. Although FIG. 3 depicts funnel collar 306 secured to threads provided on the proximal end 304, it is understood that other methods could be used to removably secure a funnel collar to crimping funnel 302. For example, removable clips could be used to secure the funnel collars to crimping funnel 302. Alternately, sliding collars could be used. A wire loading ring 308 is initially positioned proximally to the crimping funnel 302. Crimping wires 310 are connected to wire loading ring 308 and extend distally through the funnel 302 and protrude from the distal end of funnel 302. Each crimping wire 310 has an eyelet hook 312 on the end thereof for securing the eyelets of a valve. For example, each eyelet 208 of prosthetic valve 200, shown in FIG. 2, can be connected to an eyelet hook 312 in order to a fix the valve 200 in position for crimping. Crimping accessories shown in FIG. 3 can be preloaded onto catheter assembly 100. It is understood that the crimping accessories shown in FIG. 3 can be used with a variety of existing catheter assemblies other than those shown in the figures of the present application. Crimping funnel 302, funnel collar 306, and wire loading ring 308 can be formed of a variety of materials. Preferably, the crimping funnel 302, funnel collar 306, and wire loading ring 308 are formed generally of a polymer material.

Figure 4:
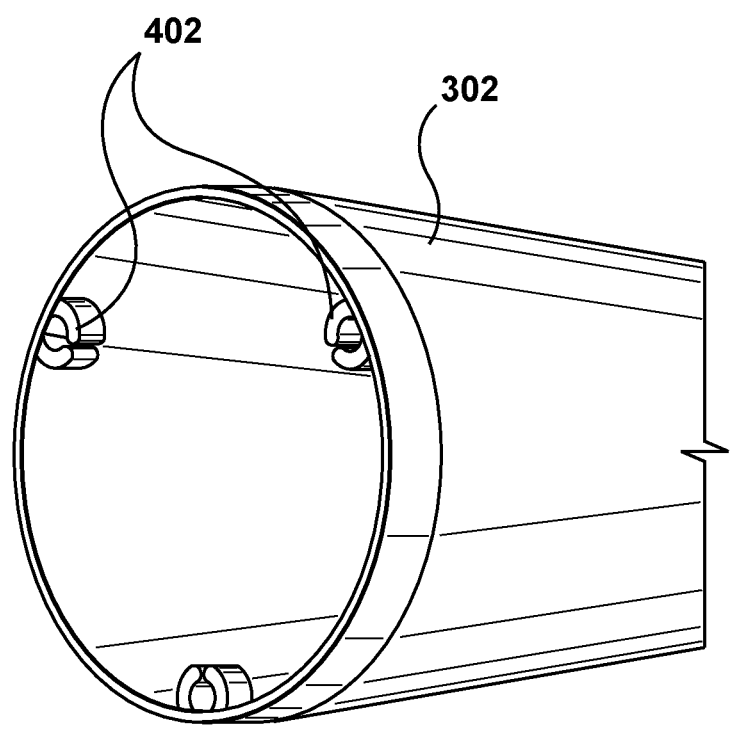
FIG. 4 is a detailed view of the distal end of a funnel according to one embodiment of the present invention.

FIG. 4 is a perspective view of the distal end of crimping funnel 302. As shown in FIG. 4, three clips 402 are provided on the inside of the distal end of crimping funnel 302. When catheter assembly 100 with crimping accessories loaded thereon is in the configuration shown in FIG. 3, each clip 402 retains one of the crimping wires 310. Such a configuration holds the crimping wires at a desired circumferential position. In operation, a prosthetic valve, such as valve 200 shown in FIG. 2, is loaded onto catheter assembly 100 when funnel 302 and crimping wires 310 are generally in the position shown in FIG. 3. At this point eyelet hooks 312 are positioned distally of the valve retainer 136. Preferably, three crimping wires 310 are used. It is understood that one, two, or more than three crimping wires can be provided, each corresponding to an eyelet 208 on a prosthetic valve to be loaded onto the catheter assembly 100. Wire loading ring 308 is preferably removably attached to introducer 116. As noted above, crimping wires 310 are connected wire loading ring 308. Therefore, when eyelet hooks 312 are positioned within eyelets 208, valve 200 can be held in a fixed axial position as funnel 302 is moved distally down the catheter assembly 100.

Figure 5:
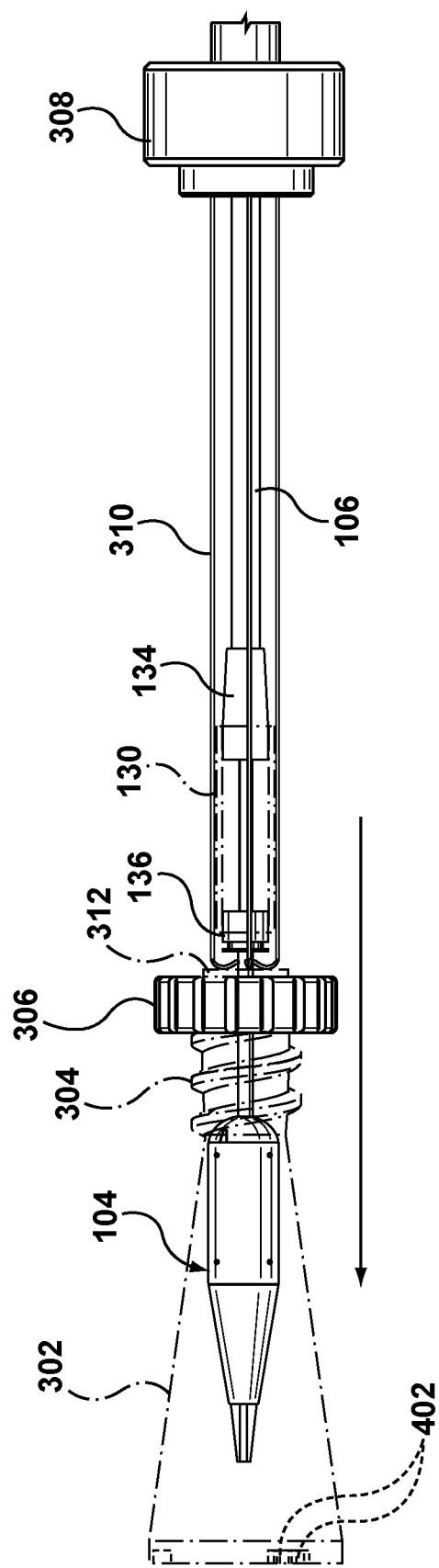
FIG. 5 illustrates a catheter assembly with crimping accessories in one stage of the crimping process. At this stage, the crimping funnel has been advanced over the prosthetic valve to crimp the valve.

FIG. 5 illustrates the distal end of catheter assembly 100 after crimping funnel 302 has been advanced distally down the catheter assembly. Because the prosthetic valve assembly 200 is held in place by the crimping wires 310 as funnel 302 is forced distally down the catheter assembly 100, the diameter of the prosthetic valve assembly 200 is gradually decreased until the valve 200 is crimped and positioned substantially within the split proximal end 304 of crimping funnel 302. At this point the entire funnel 302 is positioned distally of valve retainer 136 and valve retaining sleeve 130. Eyelet hooks 312 of crimping wires 310 remain hooked in eyelets 208 of prosthetic valve assembly 200.

Figure 6:
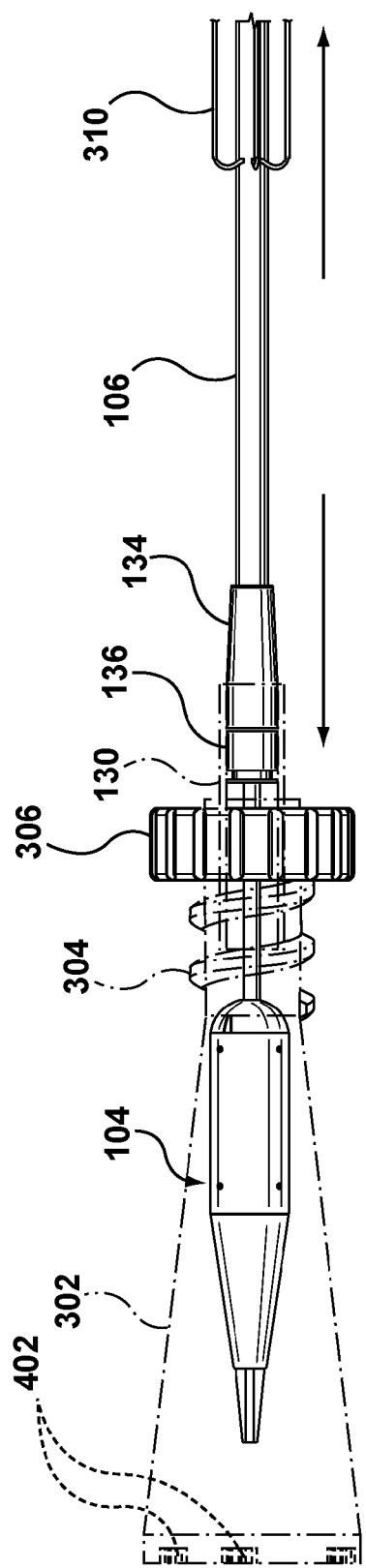
FIG. 6 illustrates the distal end of a catheter assembly with crimping accessories in another stage of the crimping process. At this stage, the wire crimping hooks have been removed from the prosthetic valve and the wire loading ring has been retracted.

Eyelet hooks 312 are then removed from eyelets 208 of the prosthetic valve 200. The wire loading ring 308 is then retracted proximally along the catheter assembly 100. At this point outer delivery shaft 106 can be advanced distally, thereby advancing valve retaining sleeve 130 over the crimped valve, as shown in FIG. 6. As valve retaining sleeve is advanced, its distal end primarily contacts barbs 212 of prosthetic valve assembly 200, thereby reducing friction that could be caused by the inner surface of valve retaining sleeve 130 sliding over support frame 202. This reduces damage to the support frame 202 and the sutures securing the valve skirt 206 to the support frame 200. It is understood that the crimping methods described herein can be used to crimp valves that do not have barbs provided thereon. Alternate methods can be used to prevent damage to support frame 202. For example, in other embodiments, skirt 206 can be bonded to the interior of frame 202, or the sutures securing the skirt to the frame can be secured to eyelets on the interior of frame 202 or passages can be provided in frame 202 such that the sutures are not exposed on the exterior of frame 202. In such embodiments, there is a reduced risk of damage to support frame 202 as the valve retaining sleeve 130 is advanced over the prosthetic valve assembly 200.

Figure 7:
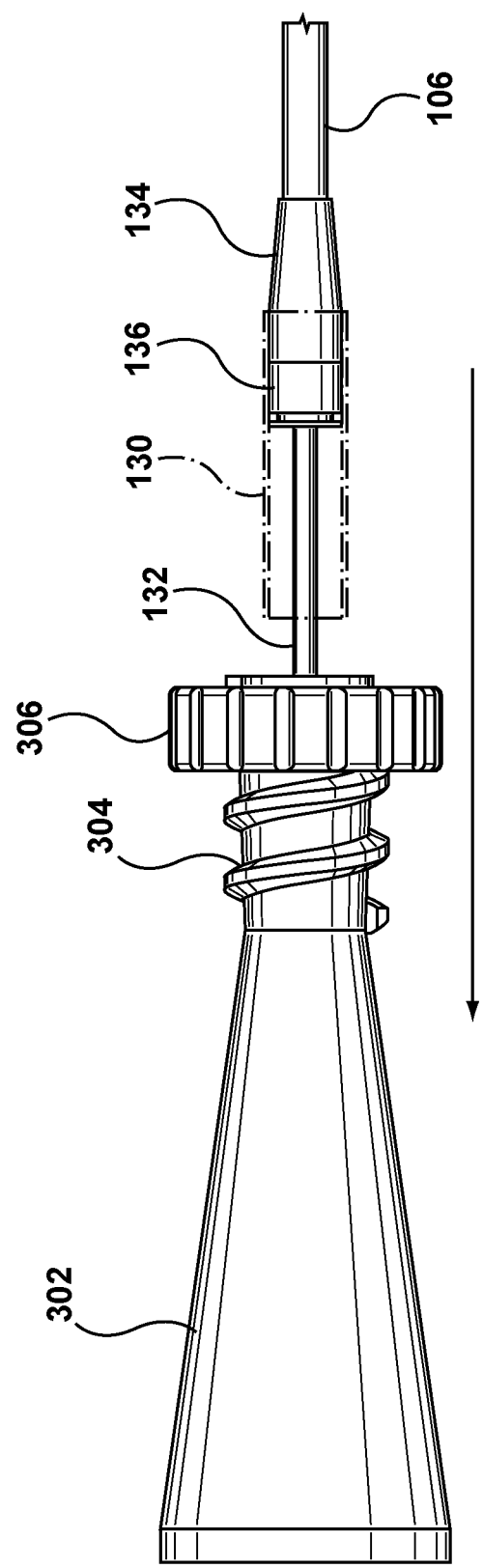
FIG. 7 illustrates the distal end of a catheter assembly with crimping accessories in another stage of the crimping process. At this stage, the crimping funnel has been removed from the valve.

As shown in FIG. 7, crimping funnel 302 is then advanced further distally, such that the distal end of valve assembly 200 is no longer encompassed by the split proximal end 304 of the crimping funnel 302. At this point the eyelets 208 of valve prosthesis 200 would be retained within valve retainer 136, as will be described in further detail with reference to FIGS. 17-18 and FIGS. 23-24. Furthermore, the proximal end of prosthetic valve assembly 200 is encompassed by valve retaining sleeve 130. The distal end of the prosthetic valve 200, including support arms 210, protrude from the distal end of valve retaining sleeve 130. At this position, support arms 210 are in the fully deployed position. Support arm sleeve 126 and the remainder of distal tip assembly 104 is encompassed by crimping funnel 302.

Figure 9:
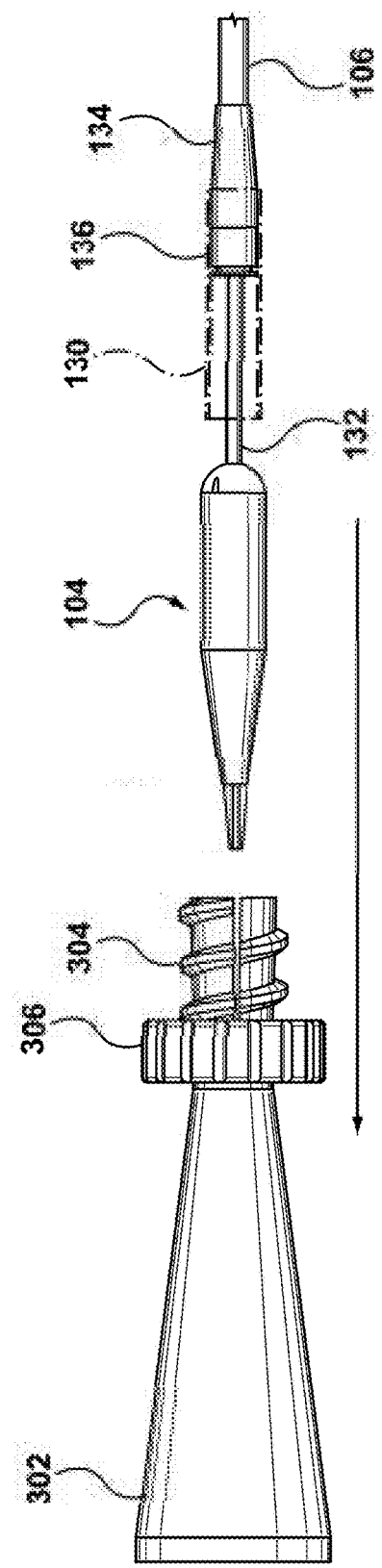
FIG. 9 illustrates the distal end of a catheter assembly with crimping accessories in another stage of the crimping process. At this stage, the funnel collar has been advanced over the distal tip of the catheter assembly.

Crimping funnel 302 is then removed from the catheter assembly by sliding it over distal tip assembly 104. Because the diameter of support arm sleeve 126 is approximately equal to or slightly larger than the diameter of split proximal end 304 of funnel 302 when funnel collar 306 is holding split proximal end 304 together, funnel collar 306 can be moved distally down the split proximal end 304 of the funnel 302 to allow the two halves of the split proximal end 304 to split apart, thereby increasing the diameter of the split proximal end 304 to a diameter greater than that of support arm sleeve 126. Funnel 302 can then be removed from the distal end of the catheter assembly 100, as shown in FIG. 9. At this point the distal end of prosthetic valve 200 is still protruding from the distal end of valve retaining sleeve 130.

Figure 10:
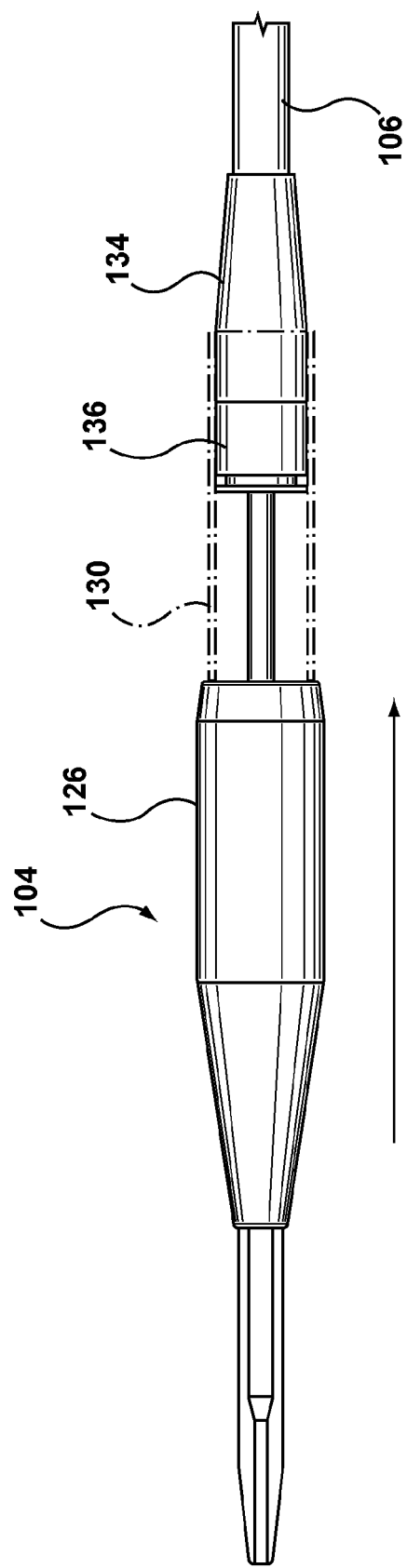
FIG. 10 illustrates the distal end of a catheter assembly with crimping accessories in another stage of the crimping process. At this stage, the support arm sleeve has been retracted to cover the distal end of the prosthetic valve.

In order to capture and crimp the distal end of prosthetic valve 200, support arm sleeve 126 is retracted proximally along the catheter 100 to reach the position shown in FIG. 10. The proximal end of the support arm sleeve 126 contacts the support arms 210 of prosthetic valve 200 thereby capturing the distal end of the prosthetic valve within support arm sleeve 126 as shown in FIG. 10. Because the inner surface of support arm sleeve 126 primarily contacts the supports arms 210, and not the main body of valve frame 202, damage to the valve frame 202 is reduced.

Figure 11:
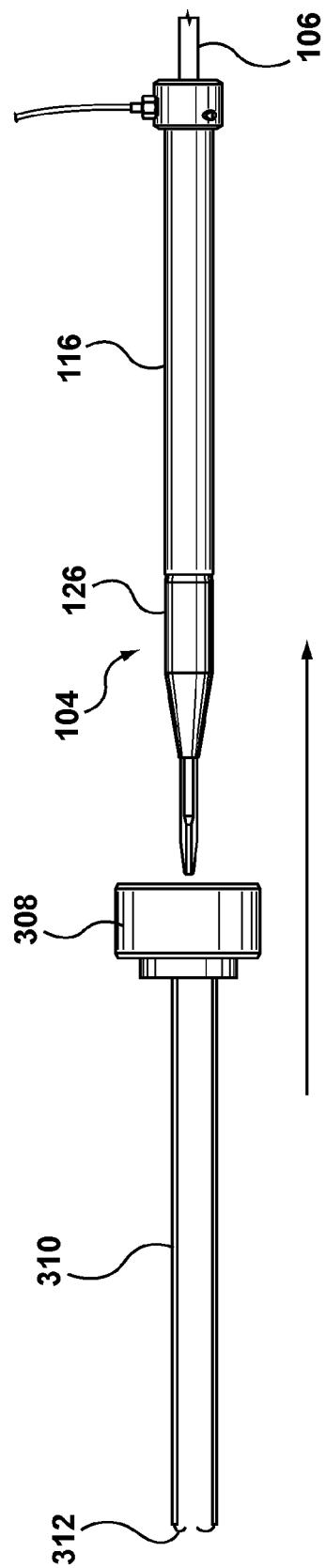
FIG. 11 illustrates the distal end of a catheter assembly with crimping accessories in another stage of the crimping process. At this stage, the wire loading ring has been removed from the catheter assembly and the introducer has been advanced.
Figure 12:
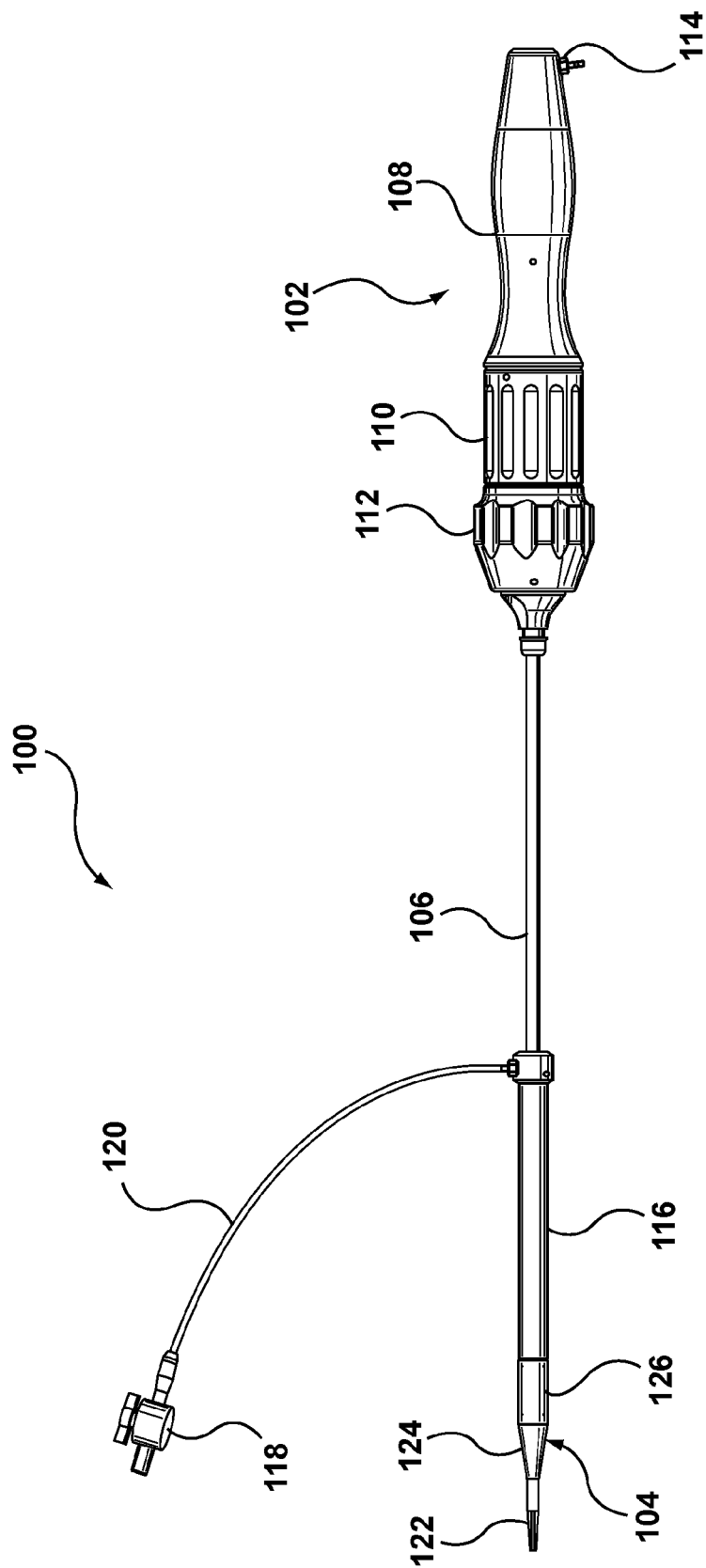
FIG. 12 illustrates a catheter assembly according to one embodiment of the present invention in a closed position after a prosthetic valve has been loaded onto the catheter.

As shown in FIG. 11, wire loading ring 308 can then be detached from introducer 116 and removed over the distal tip assembly 104. Introducer 116 can also be advanced distally to abut against the proximal end of support arm sleeve 126, thereby covering valve retaining sleeve 130. FIG. 12 shows catheter assembly 100 in a closed configuration with the prosthetic valve loaded therein. The catheter can then be used to deliver prosthetic valve assembly 200 to a desired location in a body.

Figure 8:
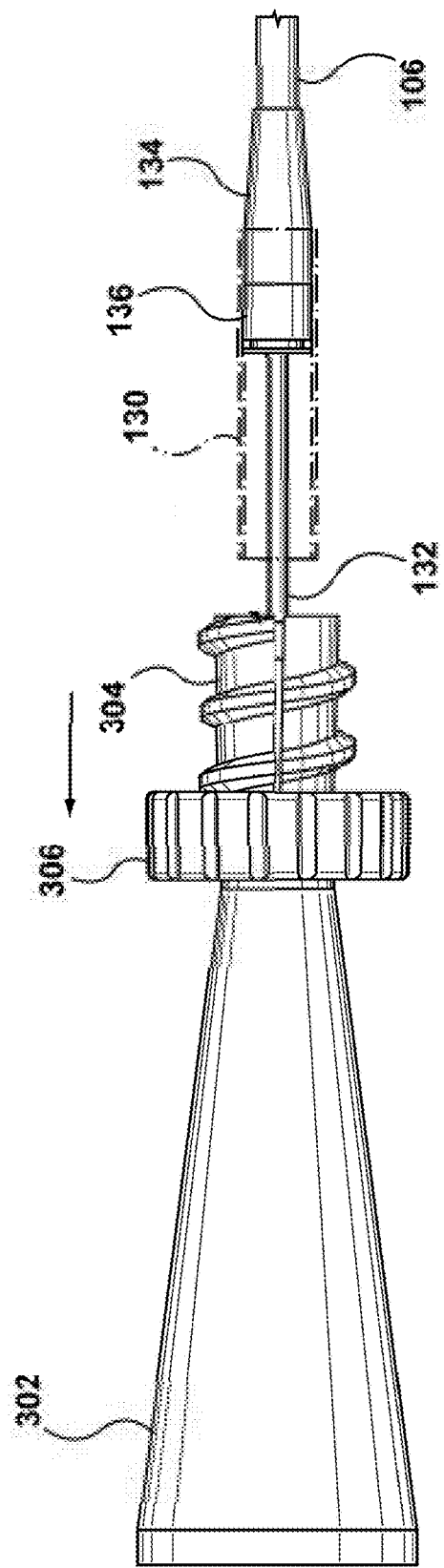
FIG. 8 illustrates the distal end of a catheter assembly with crimping accessories in another stage of the crimping process. At this stage, the funnel collar has been moved to allow the proximal end of the funnel to split, allowing the funnel to be removed over the device tip.
Figure 13:
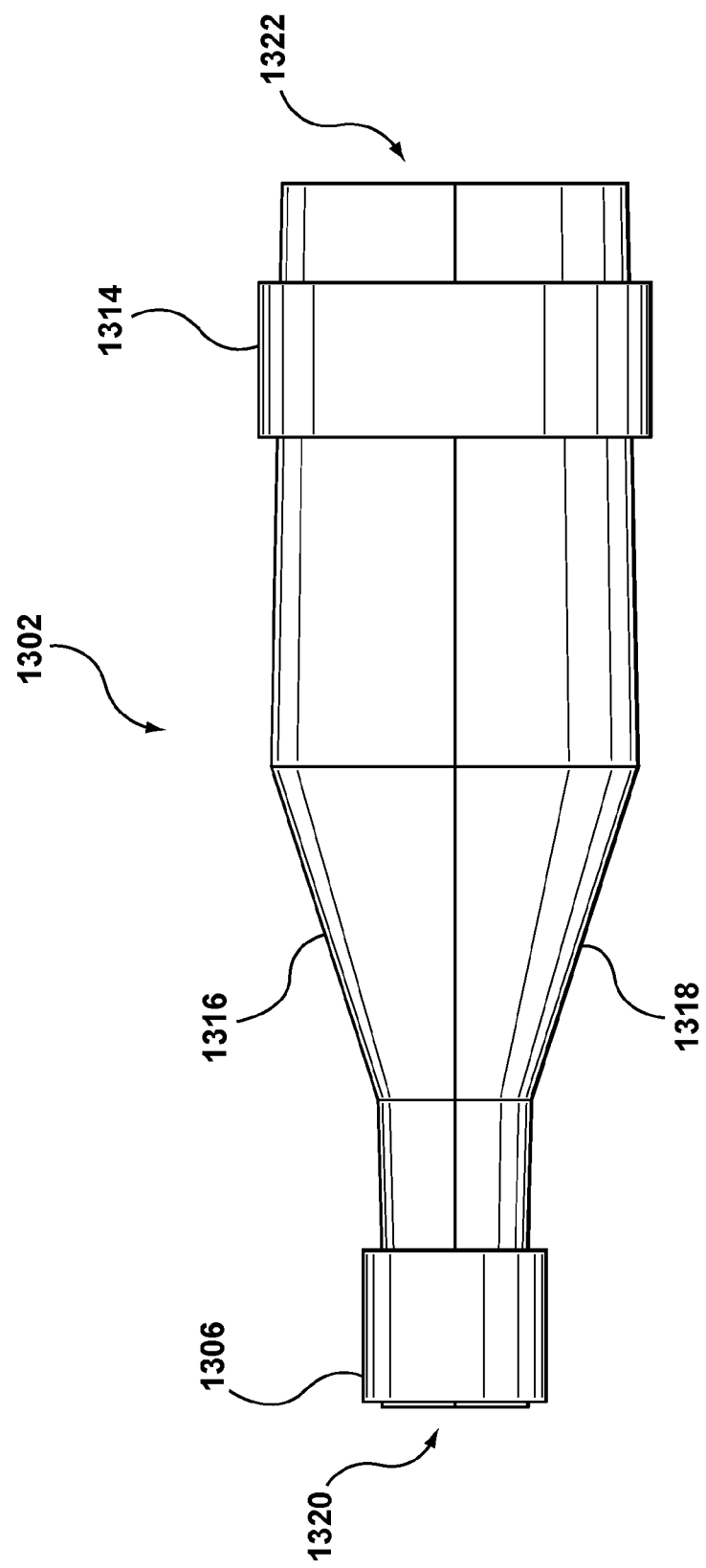
FIG. 13 illustrates an embodiment of a crimping funnel according to another embodiment of the present invention.
Figure 14:
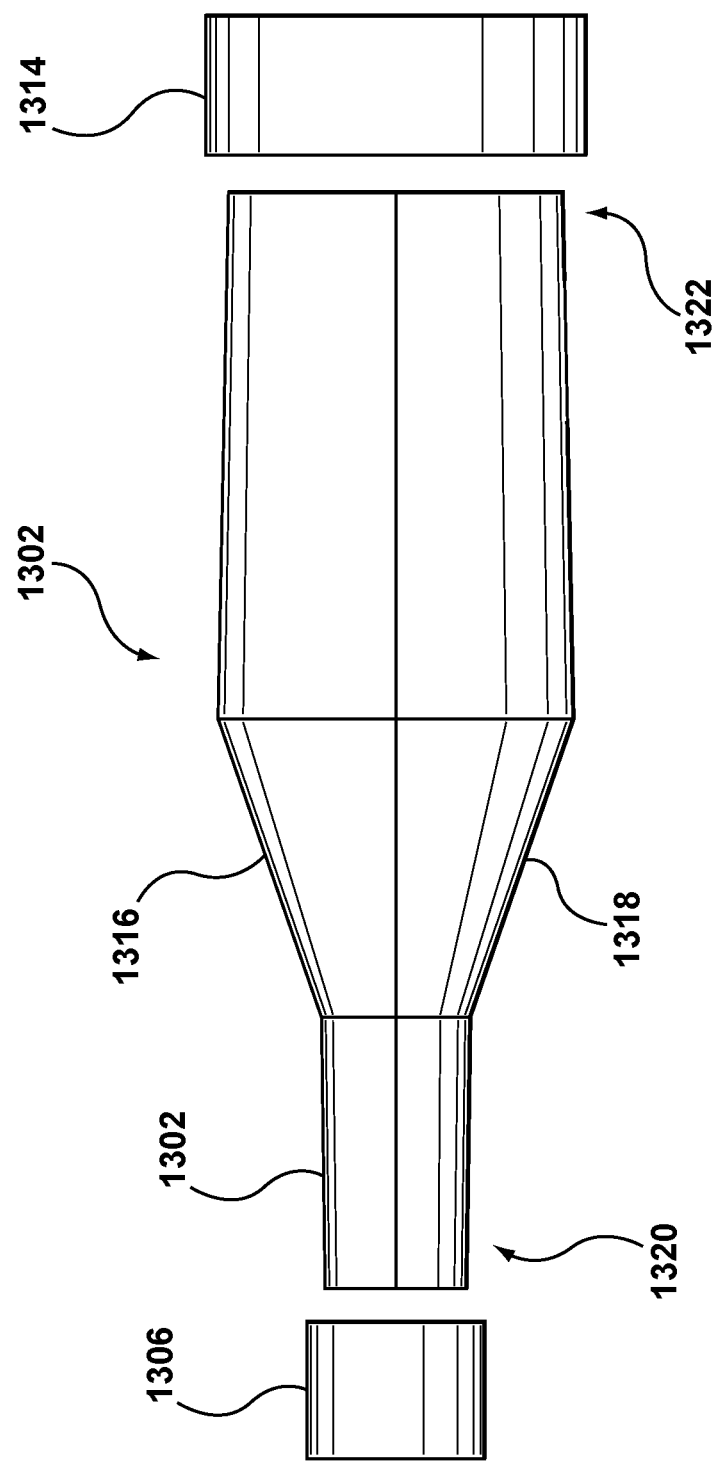
FIG. 14 illustrates the crimping funnel of FIG. 13 with the distal and proximal collars displaced from their locked position.
Figure 15:
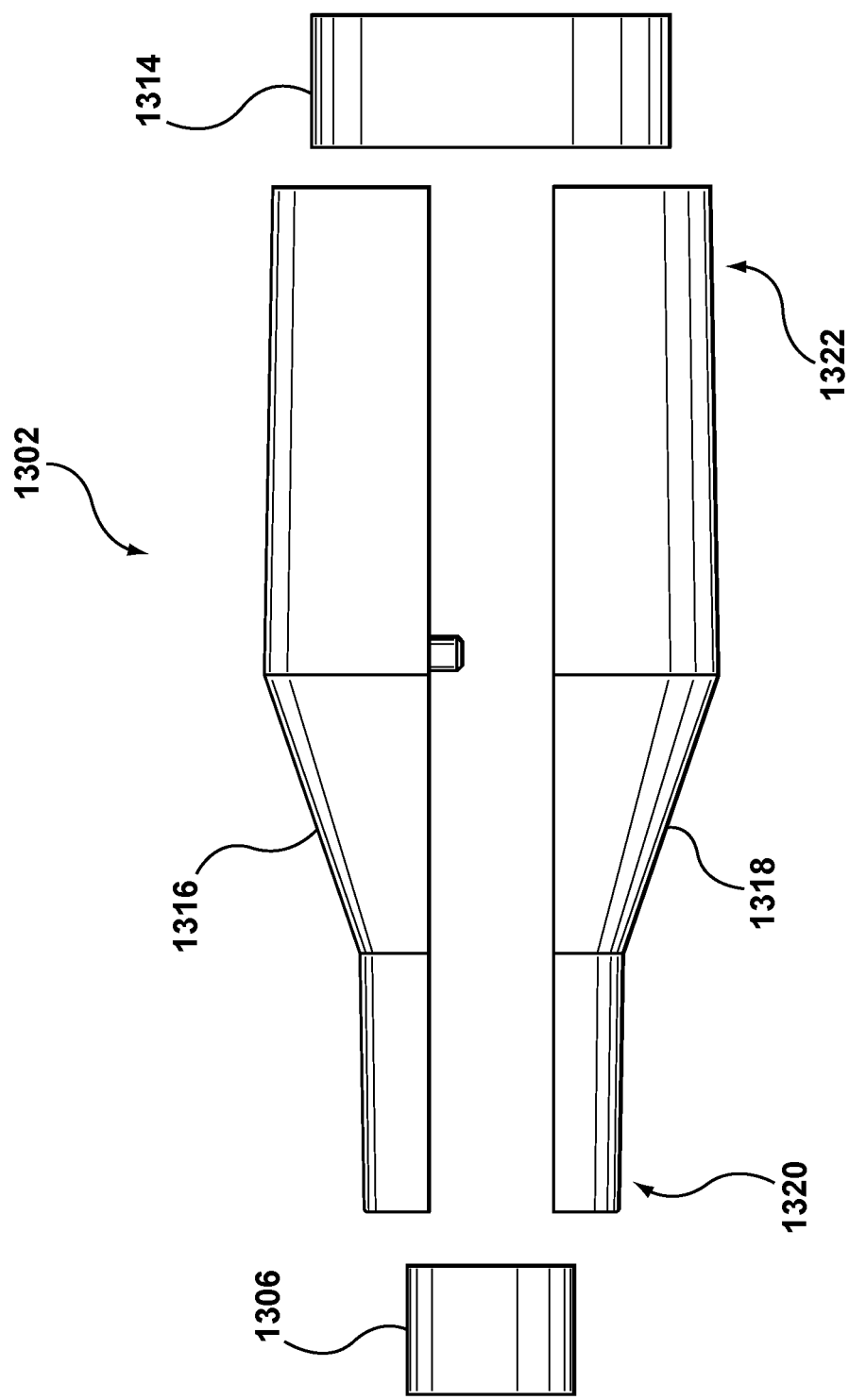
FIG. 15 illustrates the crimping funnel of FIG. 13 in its open position.

FIG. 13 shows another embodiment of a crimping funnel in accordance with the present invention. Crimping funnel 1302 has two halves 1316 and 1318, which are held together by two funnel collars, proximal collar 1306 and distal collar 1314. Proximal collar 1306 is located at the proximal end 1320 of funnel 1302 and distal collar 1314 is located at the distal end 1322 of funnel 1302. When used to crimp valve, funnel 1302 is placed on a catheter such that the smaller diameter proximal end 1320 is located proximally of the distal end 1322, in much the same configuration as funnel 302 shown in FIG. 3. Preferably, both the distal and proximal ends of crimping funnel 1302 are threaded on their exterior surface. The interior surfaces of collars 1306 and 1314 preferably have complimentary threads formed thereon. As shown in FIG. 14, to allow the funnel 1302 to split into its two halves 1316 and 1318, such that the funnel is able to slide over distal tip assembly 104 as described above with reference to FIGS. 8-9, proximal funnel collar 1306 and distal funnel collar 1314 are removed from crimping funnel 1302. Then, as shown in FIG. 15, the two halves 1316 and 1318 can be separated from each other to create a larger gap. The crimping accessories can then be removed over the distal tip 104 of catheter assembly 100.

In one embodiment, half 1316 can have a protrusion 1317, and half 1318 can have a recess (not shown) that corresponds to protrusion 1317 of half 1316. Protrusion 1317 can be seated within the recess of half 1318, preventing halves 1316 and 1318 from moving relative to each other in an axial direction.

In another embodiment, crimping funnel 1302 can be provided with a gradually decreasing diameter, similar to funnel 302 described above. The funnel can be provided with sections on each end with a diameter larger than the diameter of the funnel surrounding those sections. Proximal collar 1306 and distal collar 1314 can be attached to the increased diameter sections. In such embodiments, proximal collar 1306 and distal collar 1314 be moved towards the center of the funnel instead of being removed over the ends of the funnel. Because proximal collar 1306 and distal collar 1314 have diameters greater than the sections of the funnel interior to the end sections, funnel 1302 can split, thereby reaching a greater diameter for removal over distal tip assembly 104, without removing collars 1306 and 1314 from the funnel.

Although FIGS. 13-15 illustrate proximal funnel collar 1306 and distal funnel collar 1314 affixed to crimping funnel 1302 by the use of complementary threads, it is understood that other methods can be used to removably secure funnel collars 1306 and 1314 to crimping funnel 1302. For example, clips could be used to secure the funnel collars to crimping funnel 1302. Alternately, sliding collars could be used.

Figure 16:
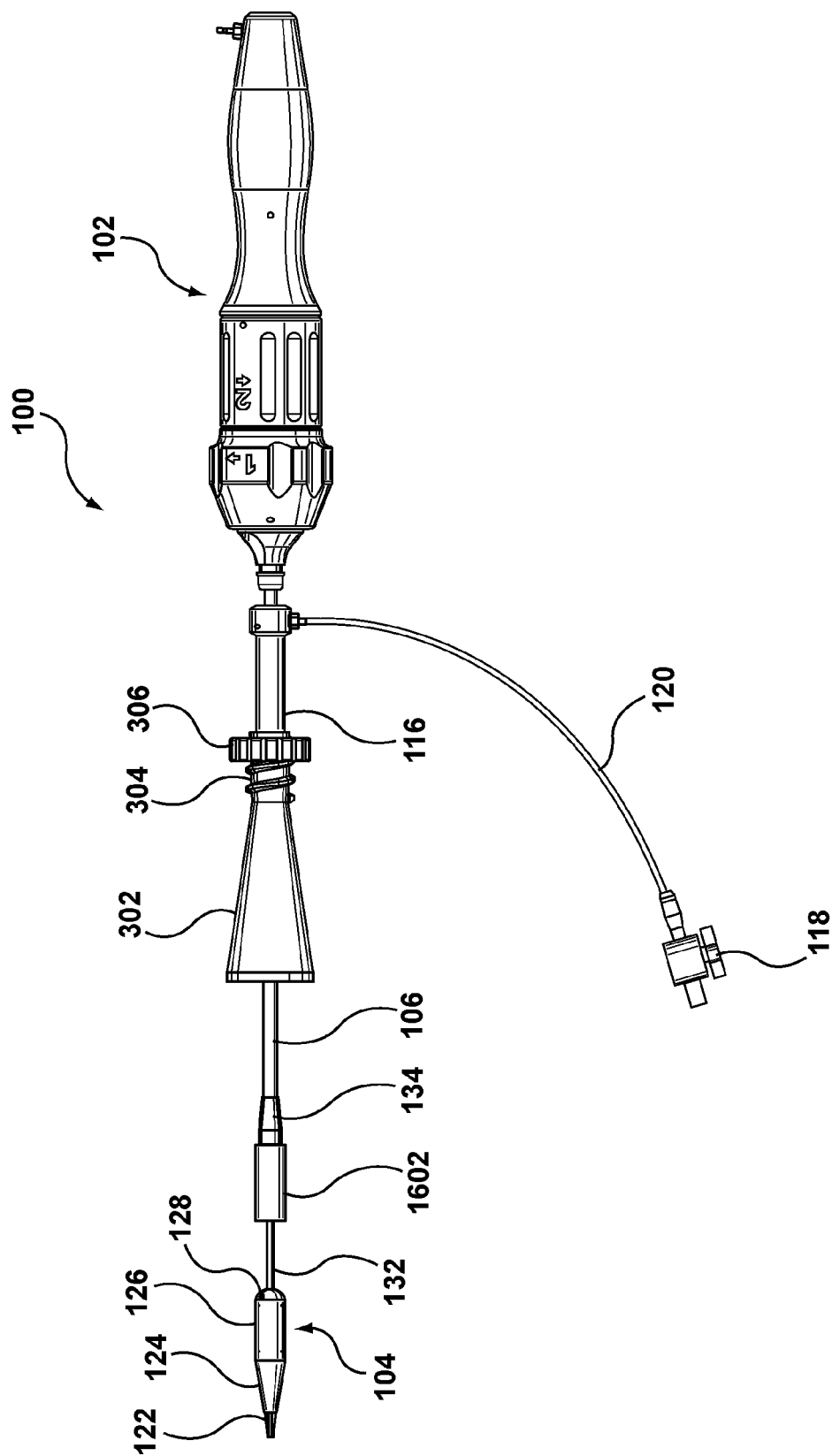
FIG. 16 illustrates a catheter assembly according to another embodiment of the present invention including accessories for crimping a prosthetic valve onto the catheter assembly.
Figure 17:
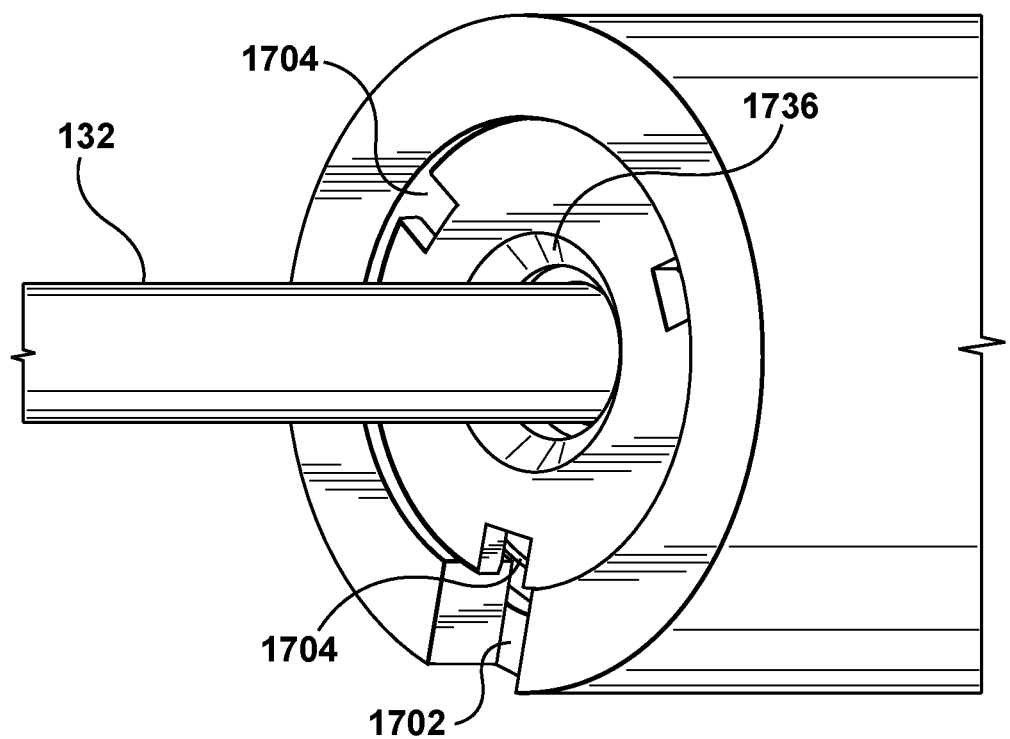
FIG. 17 is a detailed view of a valve retainer and capture sleeve according to one embodiment of the present invention.
Figure 18:
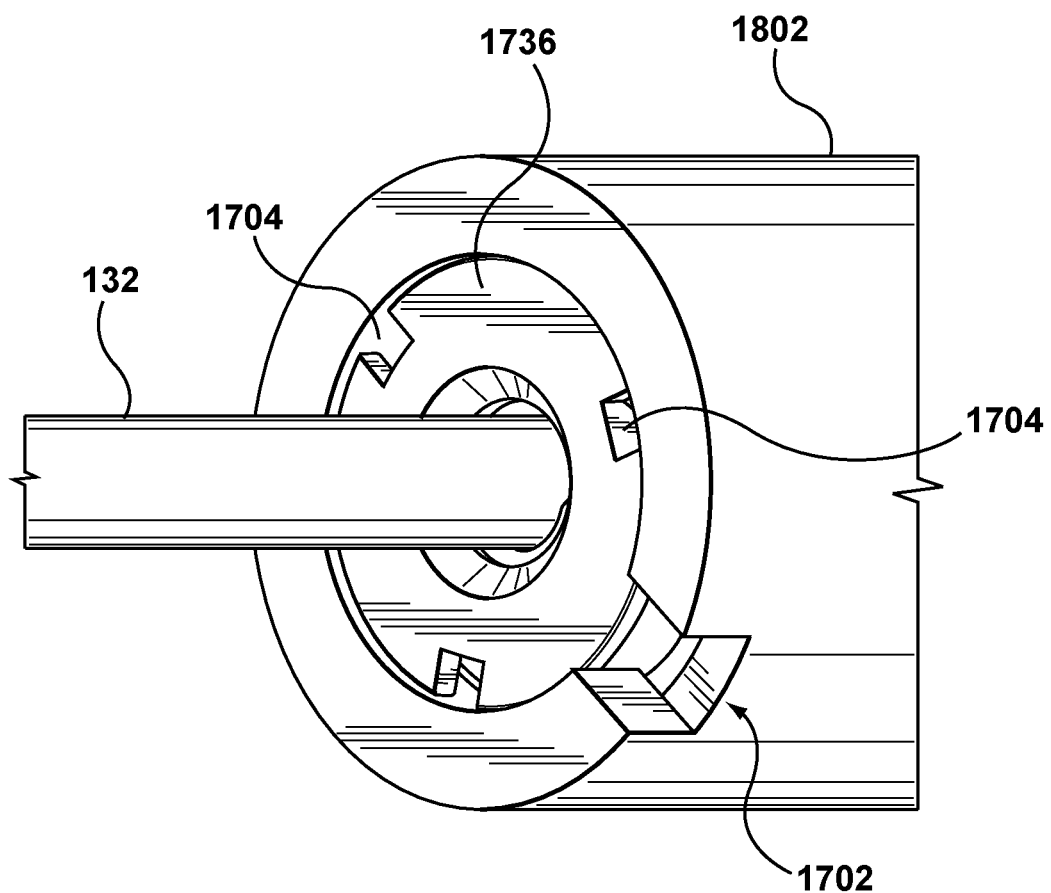
FIG. 18 illustrates the valve retainer of FIG. 16 in an alternate position.

FIG. 16 illustrates an alternate embodiment of catheter assembly 100 with crimping accessories mounted thereon. Instead of utilizing a wire loading ring to initially hold the prosthetic valve in place, the embodiment shown in FIG. 16 uses a modified valve retainer 1736, which is described in detail with reference to FIGS. 17-18, surrounded by a sleeve 1602. Catheter assembly 100 is otherwise identical to the catheter assembly shown in FIGS. 1 and 3. As with the embodiment shown in FIG. 3, the crimping accessories included with catheter 100 include a crimping funnel 302 with a split proximal end 304 and a funnel collar 306. As shown in FIG. 17, the eyelet capture sleeve 1602 is positioned around valve retainer 1736. Capture sleeve 1602 is formed with an entry notch 1702 at the distal end thereof, as shown in FIG. 17. Three retainer slots 1704 are formed in the outer perimeter of the distal end of valve retainer 1736. Retainer slots 1704 correspond to the three eyelets 208 of prosthetic valve 200, which were described in further detail above with regards to FIG. 2. Although not illustrated in FIG. 17, a circumferential channel extends around the circumference of valve retainer 1736 proximately to retainer slots 1704, much like channel 2402 shown in FIG. 24 with the respect to an alternate embodiment of a valve retainer. To load prosthetic valve 200 into valve retainer 1736, one eyelet 208 is first inserted through entry notch 702 and into a retainer slot 1704. As shown in FIG. 2, eyelets 208 are formed in generally a T-shape with the proximal end of the eyelet being wider than the face of the eyelet. Retainer slots 1704 are narrower than the proximal ends of eyelets 208. After the first eyelet has been inserted into the first retainer slot, the capture sleeve 1502 is rotated such that the first retainer slot is no longer aligned with entry notch 1702. Because the proximal end of the first eyelet 208 is wider than the retainer slot opening 1704, the first eyelet 208 is held inside the capture sleeve 1502. This process is then repeated for the remaining eyelets 208 such that all eyelets are secured within the capture sleeve 1502 and valve retainer 1736. FIG. 18 shows valve retainer sleeve 1736 and sleeve 1602 in a position where the capture sleeve 1602 has been rotated such that the entry notch 1702 is not aligned with either of the three retainer slots 1704.

Figure 19:
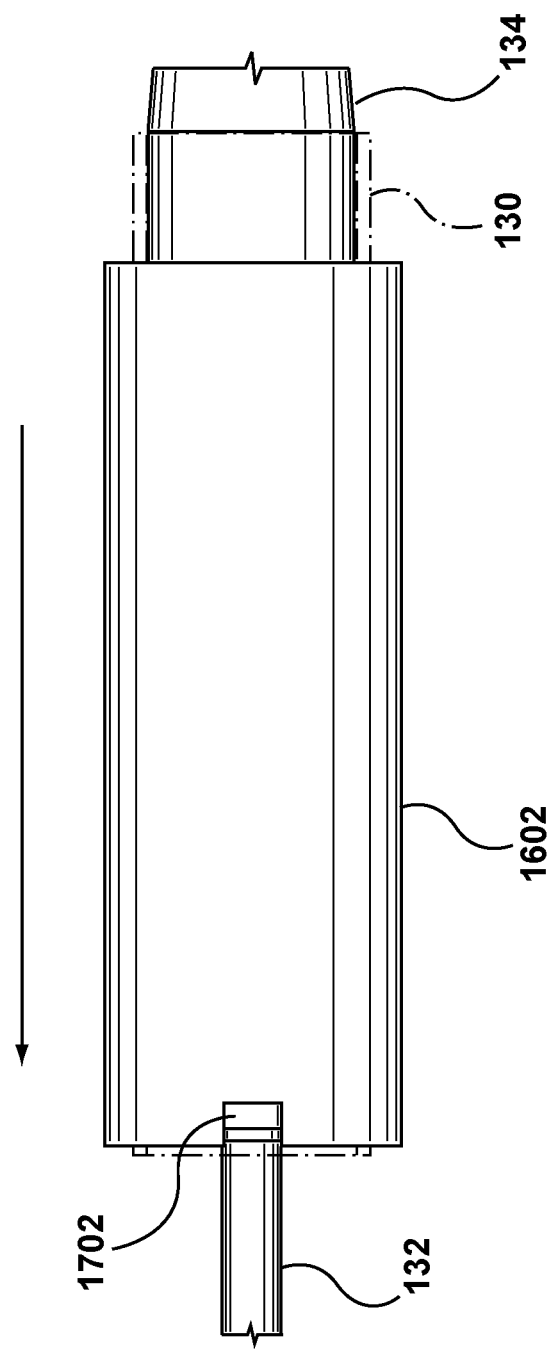
FIG. 19 illustrates removal of the capture sleeve shown in FIG. 16 from the valve retainer.

After all three eyelets 208 are secured inside the valve retainer 1736, the valve retaining sleeve 130 can be advanced underneath the capture sleeve 1602 and over valve retainer 1736, as shown in FIG. 19. After valve retaining sleeve 130 is fully advanced over the valve retainer 1736, the capture sleeve is no longer needed to retain eyelets 208 within valve retainer 1736. Capture sleeve 1602 can then be removed by sliding the sleeve distally off of the valve retaining sleeve 130. In order to remove capture sleeve 1602 from the distal end of the catheter assembly 100, the capture sleeve 1602 may need to be split for removal from the catheter assembly because its internal diameter is smaller than that of the distal tip of catheter assembly 100. Capture sleeve 1602 may be pre-slit in the manner described above with reference to crimping funnel 1302. One or more collars can be used to secure the two halves of capture sleeve 1602 together prior to removal from the catheter assembly 100. As with crimping funnel 1302, the collars can be clips or sliding snap-on collars, or can be threaded. Alternately, capture sleeve 1602 can be formed of a single piece and can be manually cut and removed after a use.

Figure 20:
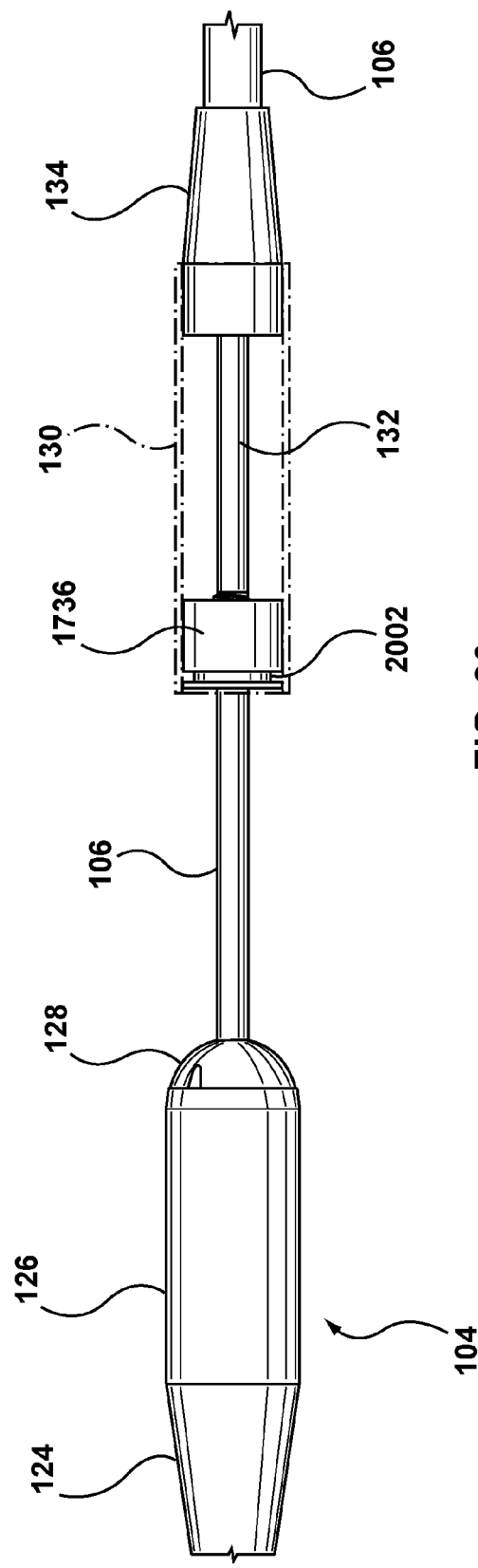
FIG. 20 illustrates the distal end of a catheter assembly according to one embodiment of the present invention prior to loading a crimping funnel onto the assembly.

After the capture sleeve 1602 is removed from the catheter assembly 100, the distal end of the catheter assembly 100 will be in the position illustrated in FIG. 20. Although prosthetic valve 200 is not depicted in FIG. 20, at this point the eyelets 208 of prosthetic valve 200 would be retained within valve retainer 1736 and the remainder of prosthetic valve 200 would be extending from the distal end of capture sleeve 130. Furthermore, although crimping funnel 302 is not shown in FIG. 20 it would at this time be positioned proximally of valve retaining sleeve 130, as shown in FIG. 16. Because the valve retainer 1736 is fixed to the intermediate shaft 132, the valve retainer serves to hold prosthetic valve assembly 200 in place as the crimping funnel is advanced over the valve assembly 200.

Figure 21:
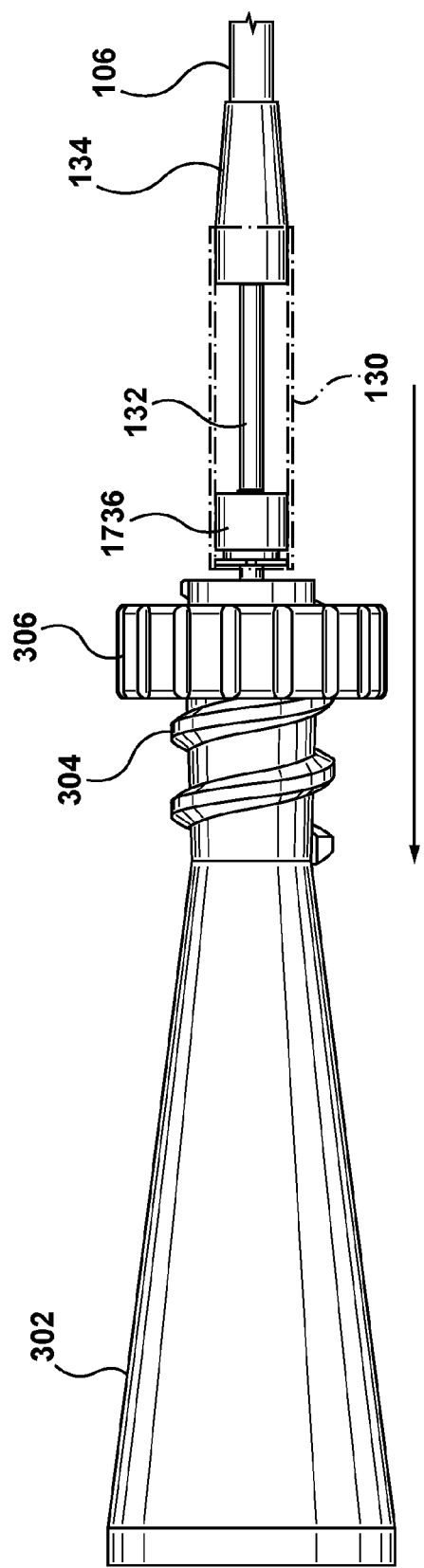
FIG. 21 illustrates the distal end of a catheter assembly according to one embodiment of the present invention with a crimping funnel loaded thereon.
Figure 22:
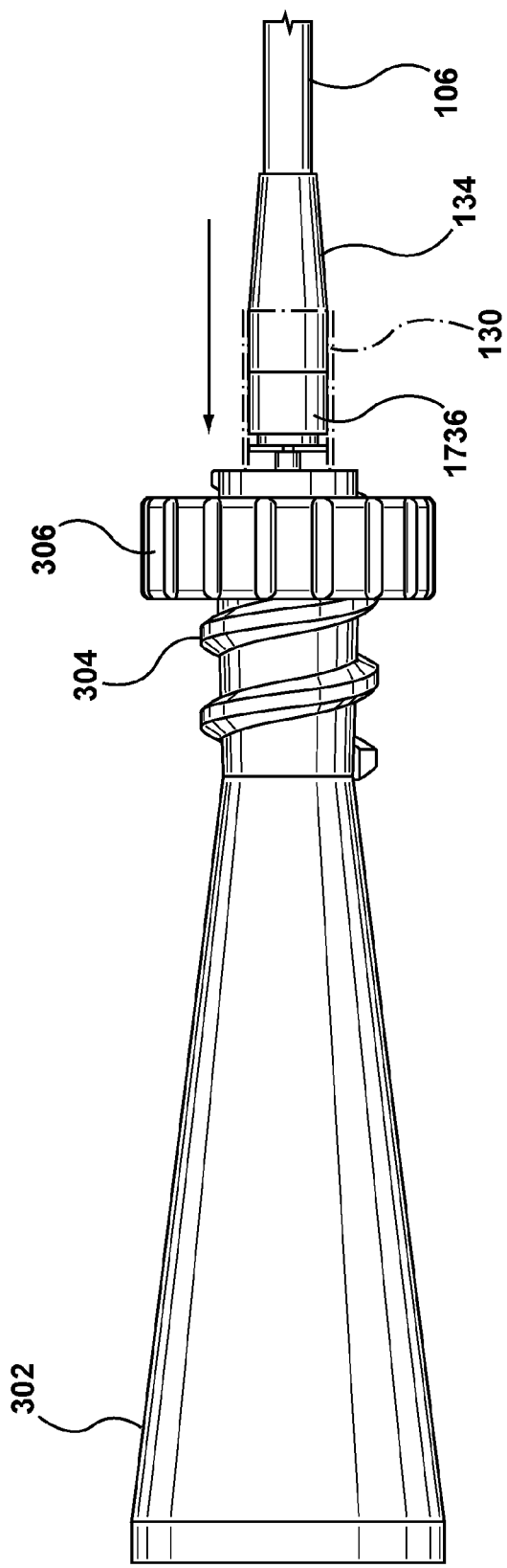
FIG. 22 illustrates a catheter assembly with crimping accessories in one stage of the crimping process. At this stage, the crimping funnel has been advanced over the prosthetic valve to crimp the valve.

Specifically, as shown in FIG. 21, the crimping funnel 302 is advanced distally while eyelets 208 of valve assembly 200 are retained within valve retainer 1736. After the prosthetic valve assembly 200 has been crimped to its delivery diameter and is housed within the split proximal end 304 of funnel 302, the sleeve 130 is advanced over the crimped valve as shown in FIG. 22. Crimping funnel 302 is then removed from the catheter assembly in the manner described above with reference to FIGS. 7-10. Catheter assembly 100 can then be moved to its closed position by advancing introducer 116 to abut against the proximal end of support arm sleeve 126 as shown in FIG. 12.

Figure 23:
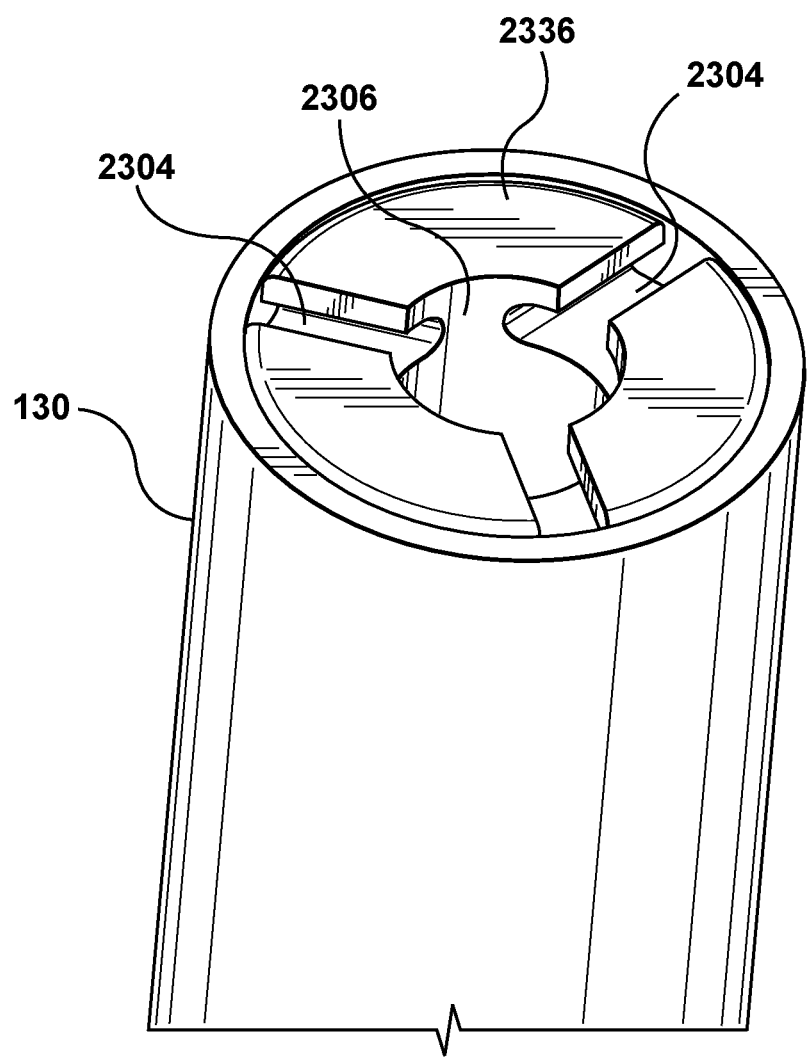
FIG. 23 illustrates a valve retainer and capture sleeve according to another embodiment of the present invention.

FIG. 23 illustrates another embodiment of a valve retainer according to the present invention. Valve retainer 2336 is configured to be operated without the need for a separate capture sleeve. Slots 2304 are opened to central lumen 2306. This configuration allows eyelets 208 to be loaded into retainer slots 2304 from the inside of central lumen 2306, thereby avoiding the need for a notch in the outer sleeve to allow introduction of the eyelets 208 into the retainer slots 2304. As a result, valve retainer 2336 can be used with valve retaining sleeve 130, eliminating the need for a separate capture sleeve and saving the user from the necessity of removing the capture sleeve after loading the valve.

Figure 24:
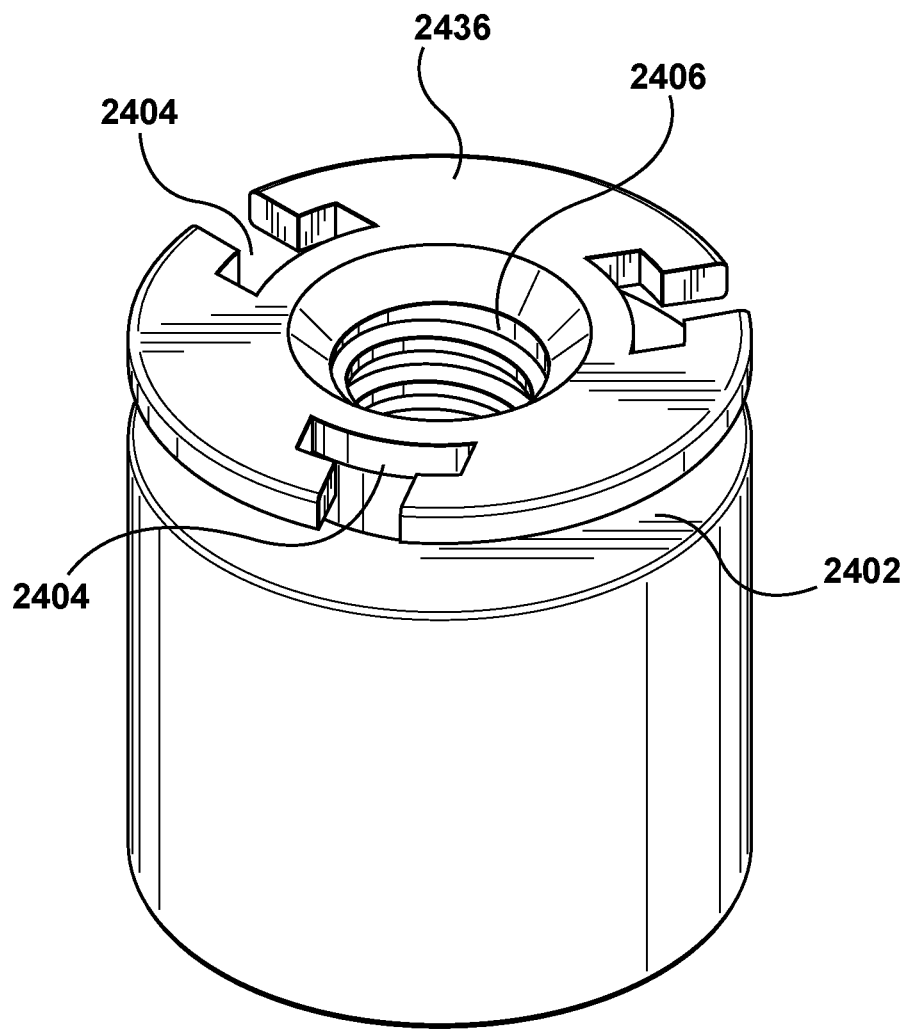
FIG. 24 illustrates a valve retainer according to another embodiment of the present invention.

FIG. 24 illustrates another embodiment of a valve retainer according to the present invention. Valve retainer 2436 has a plurality of retainer slots 2404, a circumferential channel 2402 beneath the retainer slots 2404, and a central lumen 2406 to receive intermediate delivery shaft 132. As seen in FIG. 24, the interior of retainer slots 2404 is wider than the portion of retainer slots 2404 opened to the outside of valve retainer 2436. This feature allows valve retainer 2436 to be used without the necessity of a separate capture sleeve. To load a prosthetic valve into valve retainer 2436, the ends of eyelets 208 are first inserted into the wider interior portion of slots 2404. The ends of eyelets 208 can then be moved towards the exterior of retainer slots 2404, such that the larger end of eyelets 208 are prevented from passing through the narrower portions of retainer slots 2404. Although not shown in FIG. 24, valve retainer 2436 would be encompassed by valve retaining sleeve 130 when eyelets 208 are loaded into the retainer. Therefore, eyelets 208 would be prevented from escaping the valve retainer by passing out of the retainer slots 2404 towards the exterior of valve retainer 2436. In addition, because valve 200 is preferably formed of a self expanding material, e.g., nitinol, the eyelets 208 are naturally pressed outward against valve retaining sleeve 130.

Figure 25:
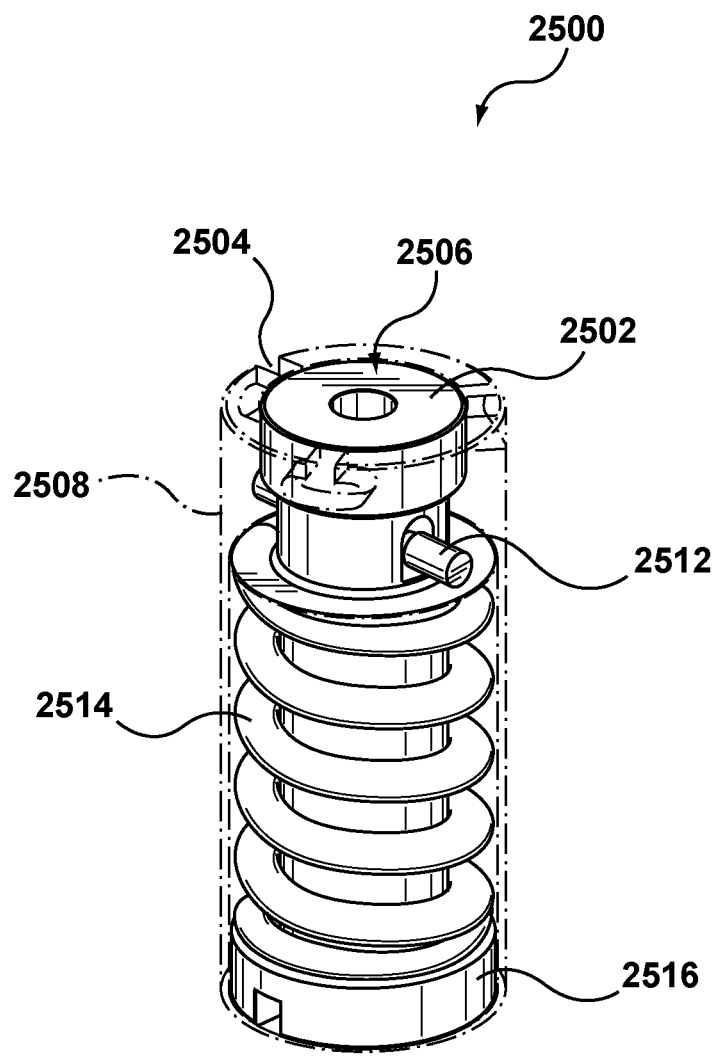
FIG. 25 illustrates a valve retaining assembly according to another embodiment of the present invention.

FIG. 25 illustrates another embodiment of a valve retaining assembly according to the present invention. Valve retaining assembly 2500 includes a housing member 2508 and a blocking member 2502. Blocking member 2502 is slidably located within housing member 2508. Retainer slots 2504 are provided on the top perimeter of housing member 2508. A central lumen 2506 extends through the blocking member 2502 and thereby through the housing member 2508. Central lumen 2506 can receive a delivery shaft therethrough. Valve retaining assembly 2500 also includes guide pins 2512 whose function is detailed with respect to FIGS. 27 and 28 herein. A spring 2514 is also included. Although spring 2514 is illustrated as a coil spring, other types of springs can be used in valve retaining assembly 2500 in place of or in addition to the coil spring. For example, any type of mechanical spring can be used, or multiple smaller mechanical springs can be used. Spring 2514 can also be formed of a resilient material, such as silicon. Blocking member 2502 is secured to a base 2516.

Figure 26:
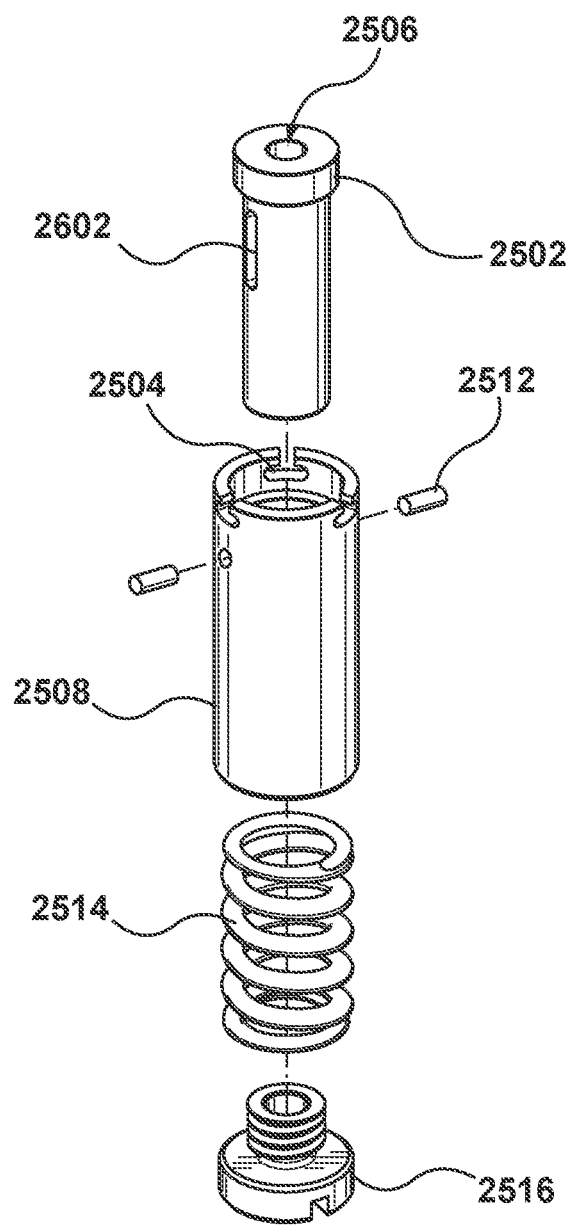
FIG. 26 illustrates the valve retaining assembly of FIG. 25 in an exploded view.

FIG. 26 is an exploded view of valve retaining assembly 2500. As seen in FIG. 26, blocking member 2502 further includes two vertical channels 2602. Guide pins 2512 extend through housing member 2508 into vertical channels 2602. The interaction of guide pins 2512 and vertical channels 2602 allows vertical movement of blocking member 2502 with respect to housing member 2508 while preventing rotational movement of blocking member 2502 with respect to housing member 2508. Base 2516 has a screw top for securing the blocking member 2502 thereto. However, it is understood that various alternate methods could be used to affix blocking member 2502 to base 2516. For example, snap-lock or ratcheting systems can be used to attach blocking member 2502 to base 2516.

Figure 27:
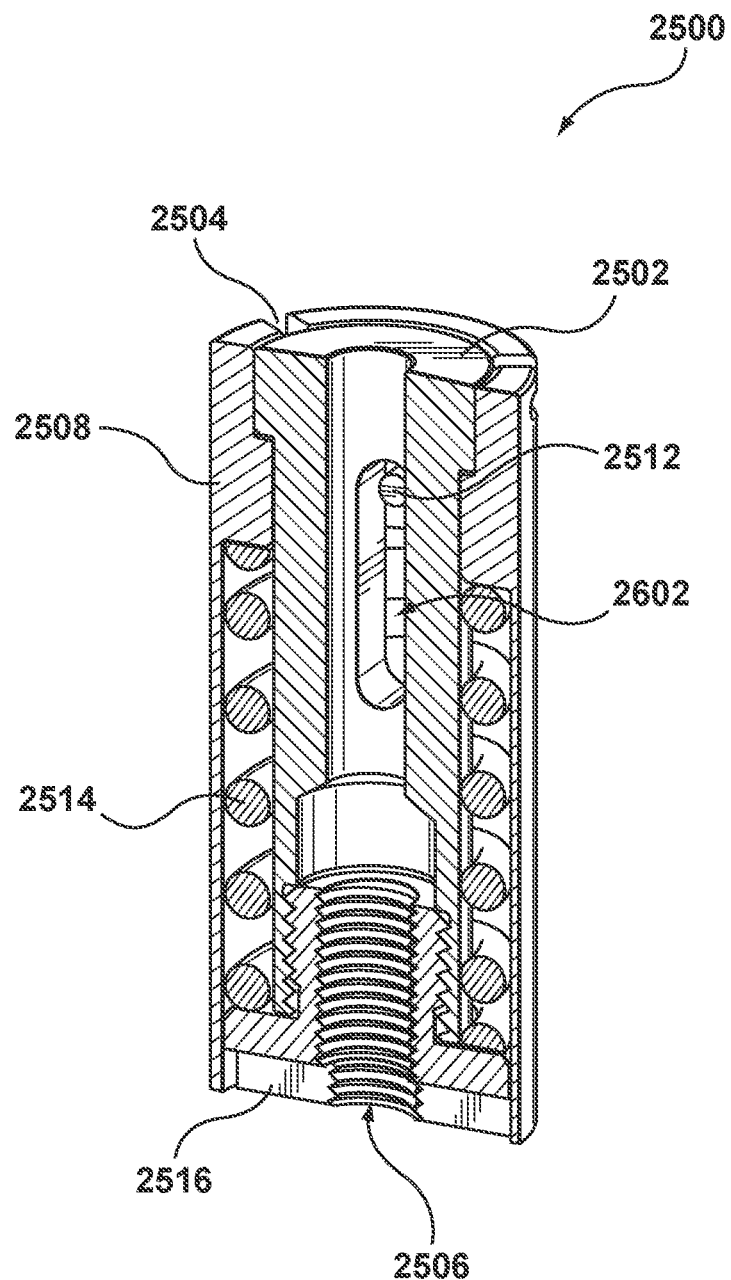
FIG. 27 illustrates a cross-section of the valve retaining assembly of FIG. 25.

FIG. 27 is a cross-sectional view of valve retaining assembly 2500 in the position shown in FIG. 25. As seen in FIG. 27, when blocking member 2502 is in its fully down position with respect to housing member 2508, the top of blocking member 2502 is flush with the top of housing member 2508. The directional orientation terms used herein to facilitate description of embodiments of the present invention, for example, fully down, upwards, downwards, upwardmost, downwardmost, etc, refer to the various assemblies and members as they are oriented in the respective figures. Other orientations may be used without departing from the scope of the present invention.

Figure 28:
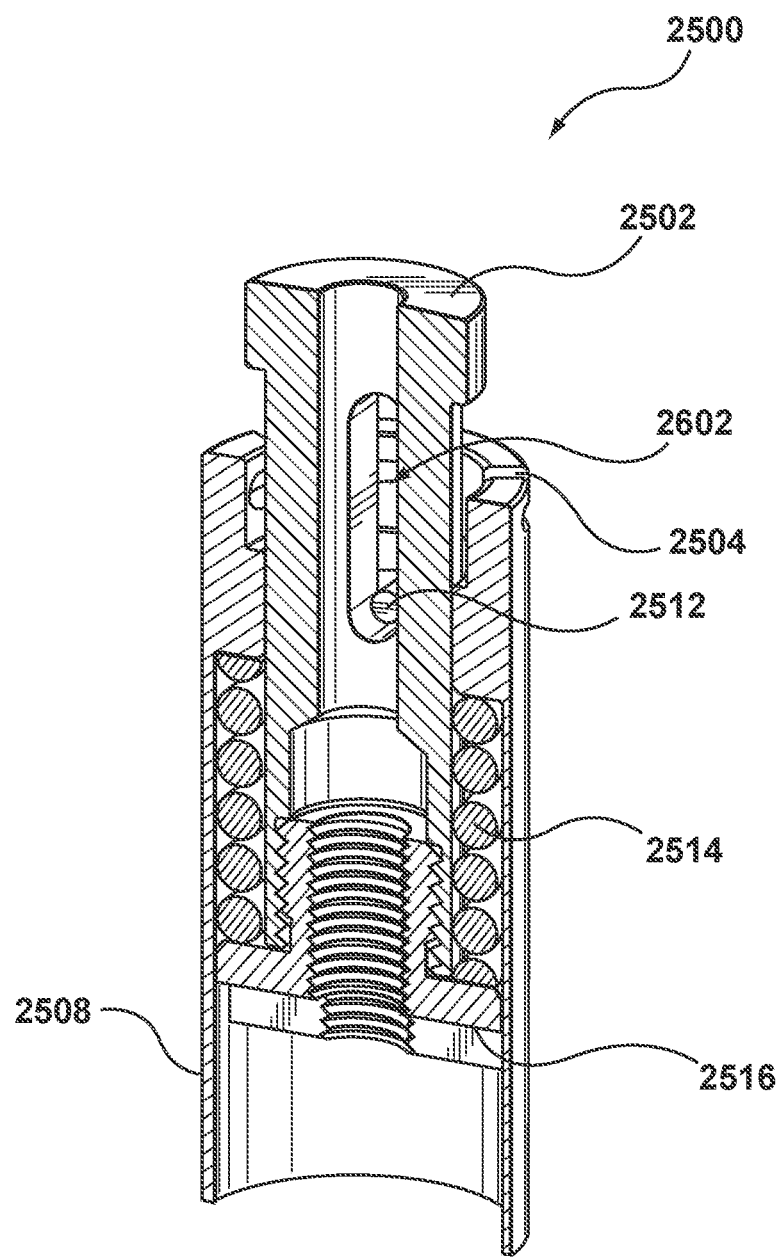
FIG. 28 illustrates a cross-section of the valve retaining assembly of FIG. 25 in a second position.
Figure 29:
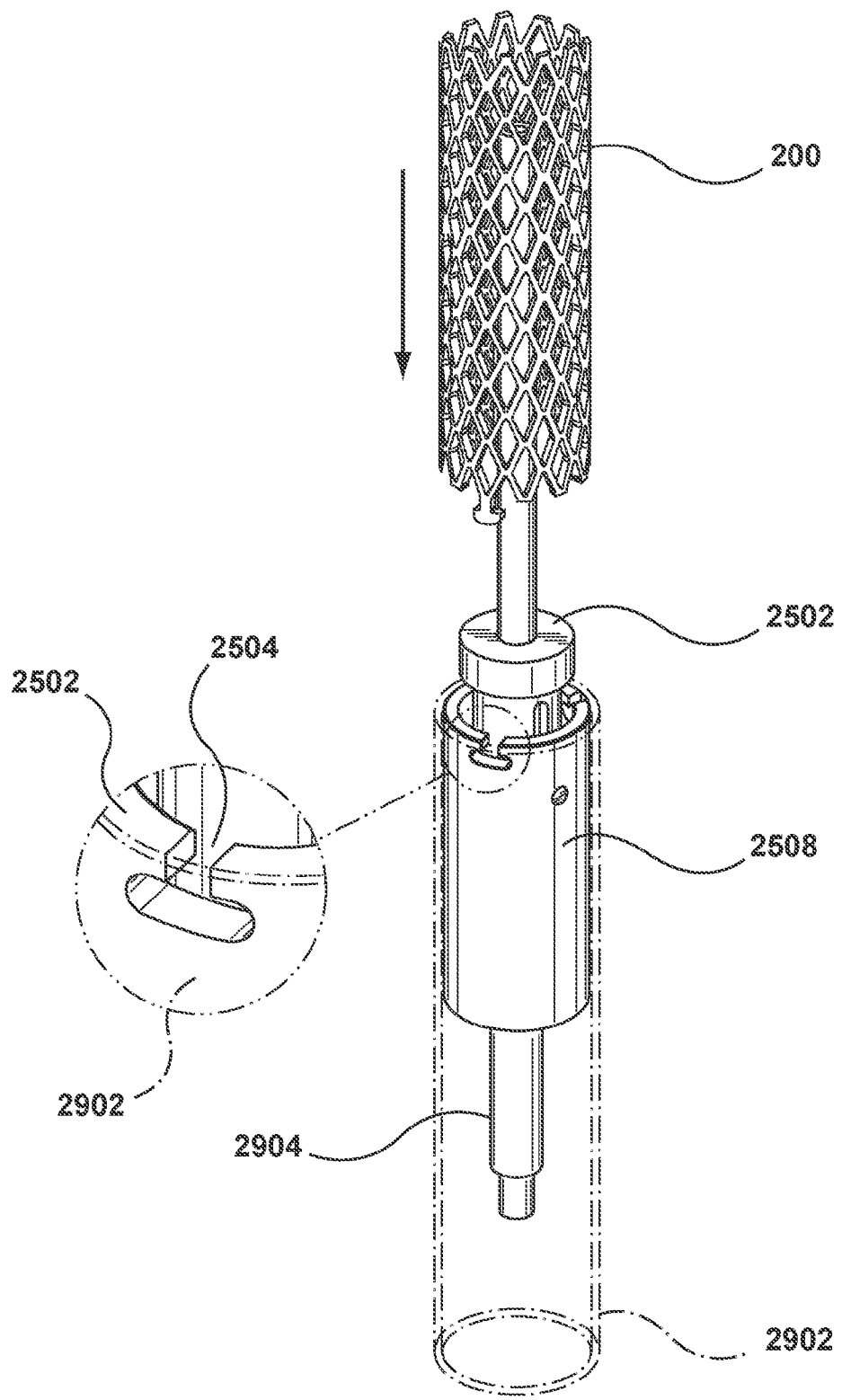
FIG. 29 is a perspective view of the valve retaining assembly of FIG. 25 prior to mounting a prosthesis thereto.

FIG. 28 shows valve retaining assembly 2500 with the blocking member in its upwardmost position with the respect to housing member 2508. As shown in FIG. 28, when blocking member 2502 is in this upwardmost position, spring 2514 is compressed. Thus, blocking member 2502 is biased to the position shown in FIG. 27, and reaches the position shown in FIG. 28 when force is applied to the spring 2514. The position shown in FIG. 28 allows fixation hooks 208 of a prosthetic valve 200 to be fitted within retainer slots 2504, as shown in FIG. 29. Although valve retaining assembly 2500 is described herein with reference to prosthetic valve 200 for ease of description, it is understood that other prosthetic valves can be used in conjunction with valve retaining assembly 2500. Other prostheses such as stents, grafts, and other types of prostheses may also be used in conjunction with all embodiments of valve retainers and valve retaining assemblies described herein.

As shown in FIG. 29, valve retaining assembly 2500 also includes an outer tube 2902 that can be positioned around housing member 2508. When outer tube 2902 is positioned as shown in FIG. 29, the outside openings of retainer slots 2504 are covered by the top portion of outer tube 2902. A prosthetic valve 200 is advanced towards the valve retaining assembly 2500 is shown in FIG. 29. Prosthetic valve 200 is already in its crimped position, although the crimping process is not illustrated in FIG. 29. It is understood that prosthetic valve 200 can be crimped according to any of the methods described in the present application. Other crimping systems and methods known in the art can also be used to compress prosthetic valve 200 to its reduced-diameter position for attachment to a valve retainer or valve retaining assembly. Prosthetic valve 200 can also be provided to a user in its crimped position, thereby eliminating the need for on-site crimping.

As shown in FIG. 29 prosthetic valve 200 is advanced towards valve retaining assembly 2500. Blocking member 2502 is attached to a fixation shaft 2904 that is connected at an opposite end to a point within the catheter handle, and is thereby held static. Alternately, a catheter handle can be provided with controls that allow for controlled movement of fixation shaft 2904. Preferably, such controls have the ability to lock fixation shaft 2904 in a static position if such controls are provided. At this point in the attachment process, valve retaining assembly 2500 is in the position described and shown with reference to FIG. 28, that is, the blocking member 2502 is in its upwardmost position with respect to housing member 2508 and spring 2514 is compressed. Valve retaining assembly 2500 can be forced into this position by pinching outer tube 2902 and housing member 2508, thereby creating friction between outer tube 2902 and housing member 2508, and then pulling both outer tube 2902 and housing member 2508 downward, away from prosthetic valve 200 in FIG. 29. This forces downward movement of housing member 2508 relative to blocking member 2502, thereby compressing spring 2514 and resulting in blocking member 2502 reaching its uppermost position with respect to housing member 2508.

Figure 30:
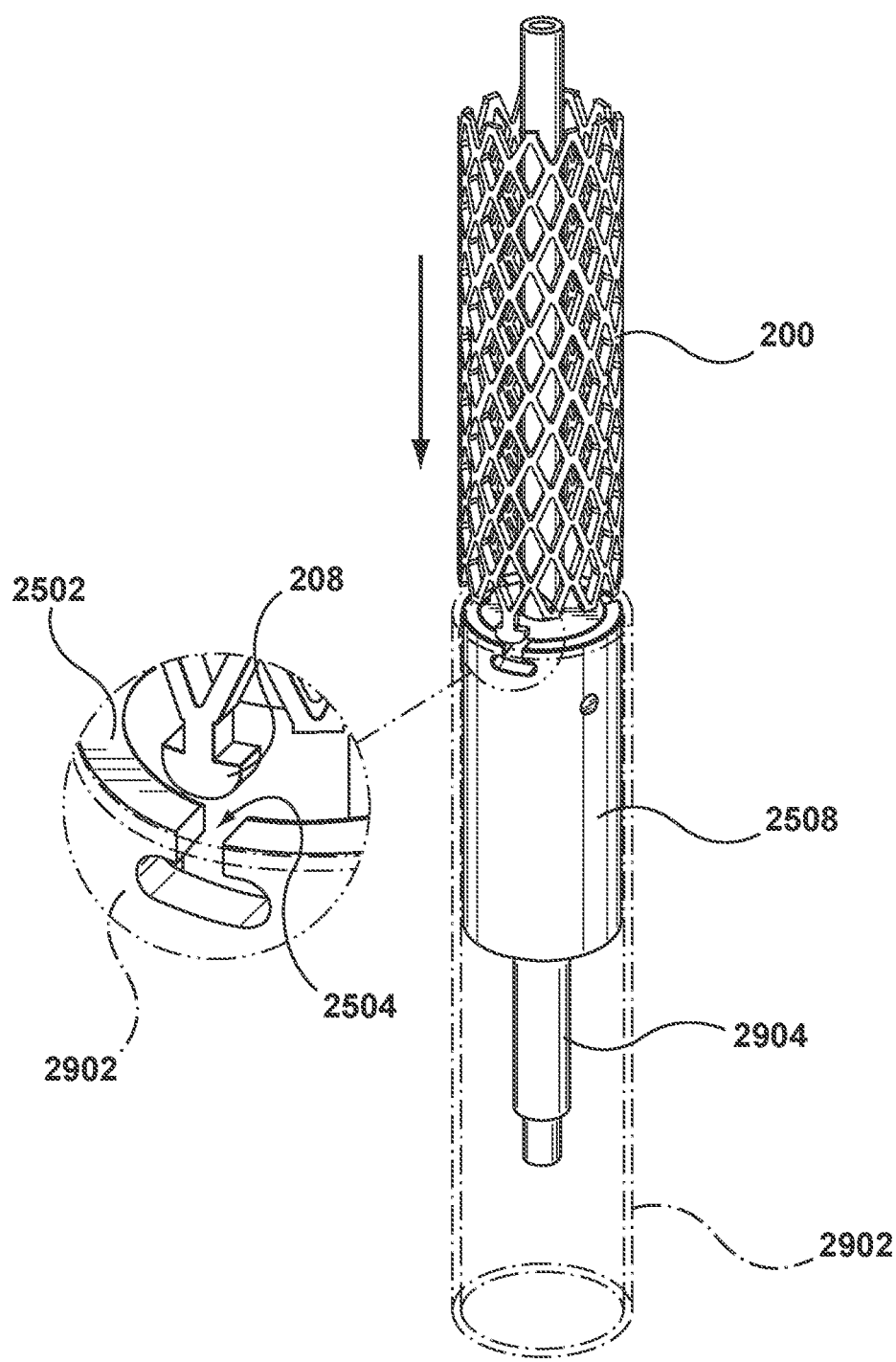
FIG. 30 is a perspective view of the valve retaining assembly of FIG. 25 at another stage of mounting a prosthesis thereto.
Figure 31:
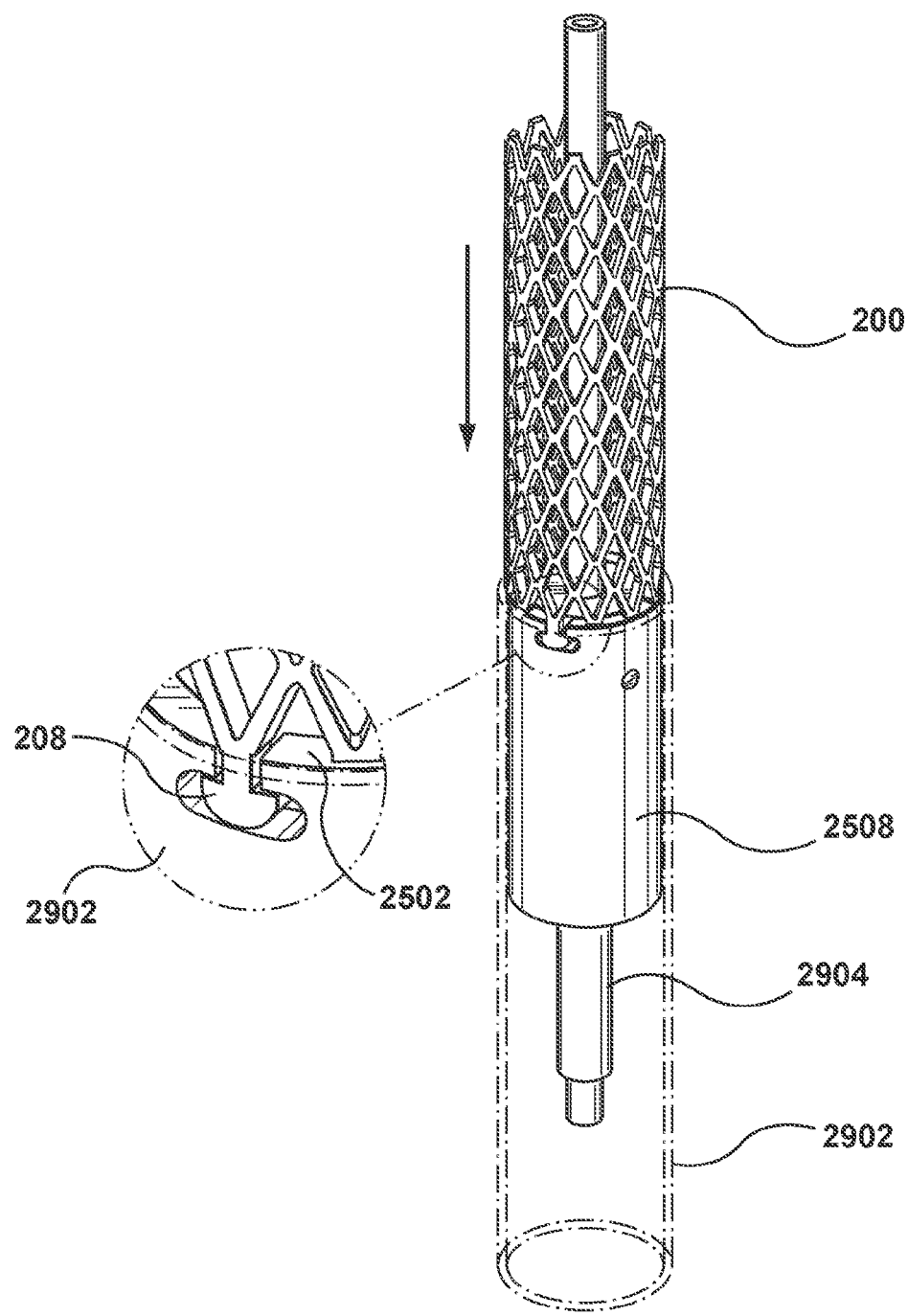
FIG. 31 is a perspective view of the valve retaining assembly of FIG. 25 at another stage of mounting a prosthesis thereto.
Figure 32:
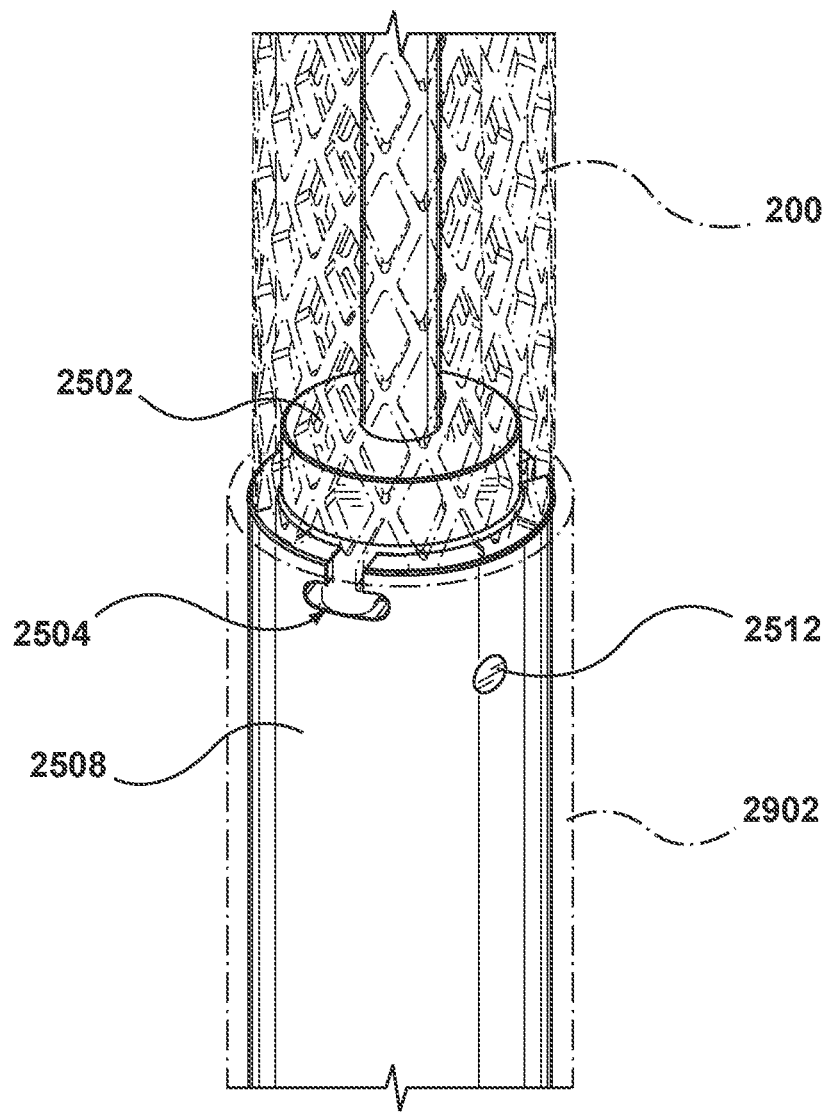
FIG. 32 is a perspective view of the valve retaining assembly of FIG. 25 with a prosthesis mounted thereto.

As shown in FIG. 30, prosthetic valve 200 is advanced to valve retaining assembly 2500. As shown in FIGS. 31-32, fixation hooks 208 of prosthetic valve 200 are placed within valve retainer slots 2504 from the inside of housing member 2508. As best seen in FIG. 32, blocking member 2502 is in its upwardmost position allowing fixation hooks 208 to be placed in retainer slots 2504 from the inside. Because outer tube 2902 covers the exterior opening of retainer slots 2504, fixation hooks 208 are held in place in retainer slots 2504. Each of the fixation hooks 208 of prosthetic valve 200 are inserted into their respective retainer slots 2504 in a similar manner. It is understood that prosthetic valve 200 can be formed with any number of fixation hooks 208, and that valve retaining assembly 2500 can be formed with a corresponding number of retainer slots 2504. When the fixation hooks 208 are housed within retainer slots 2504, the prosthetic valve 200 is in the position shown in FIG. 31. During this entire procedure friction should be kept between outer tube 2902 and housing member 2508 by clamping or pinching the outer tube 2902 and housing member 2508. This clamping can be achieved, for example, with a clamping tool or with a user's fingers.

Once all fixation hooks 208 are secured within retainer slots 2504, outer tube 2902 and housing member 2508 are moved upwards while still maintaining pressure or friction between those two components so that housing member 2508 moves upwards with respect to blocking member 2502. Blocking member 2502 is connected to the fixation shaft 2904, which is held static, and therefore blocking member 2502 does not move when outer tube 2902 and housing member 2508 are slid upwards along the axis of the delivery shaft.

Figure 33:
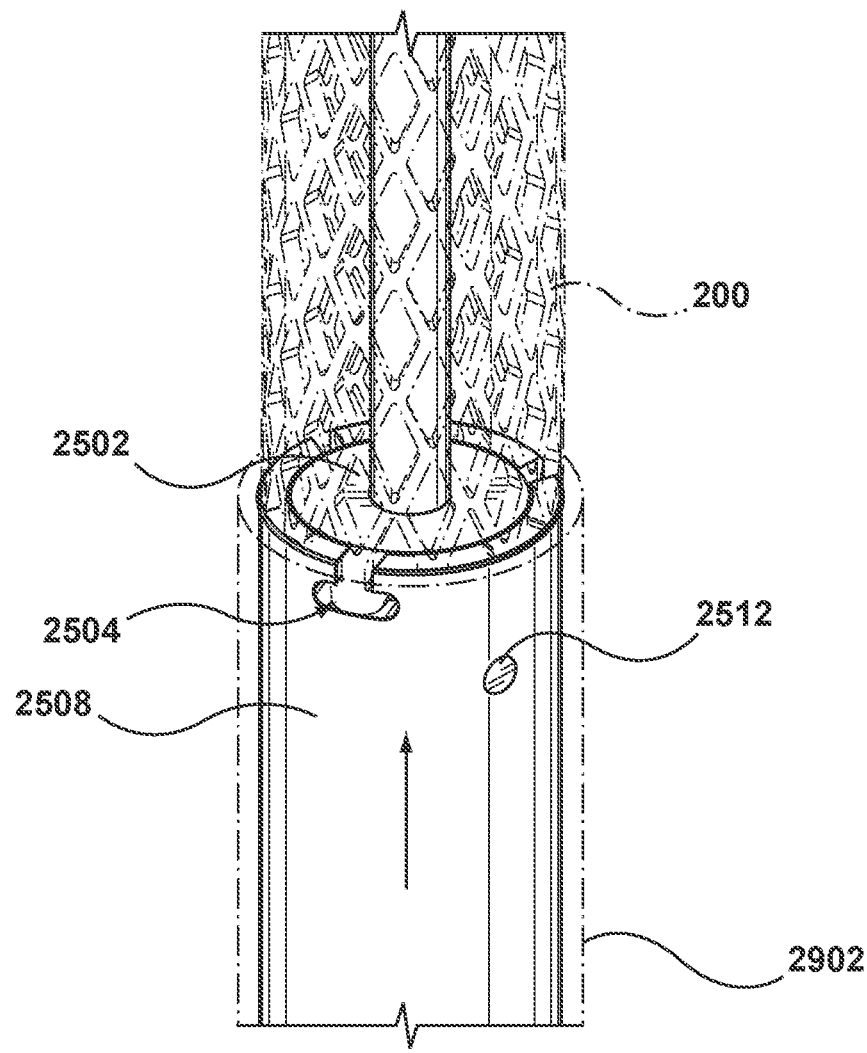
FIG. 33 is another perspective view of the valve retaining assembly of FIG. 25 with a prosthesis mounted thereto.

When outer tube 2902 and housing member 2508 reach their upwardmost position, that is, when the top of outer tube 2902 and the top of housing member 2508 are flush with the top of blocking member 2502, the pressure between outer tube 2902 and housing member 2508 can be released. This position is shown in FIG. 33.

Figure 34:
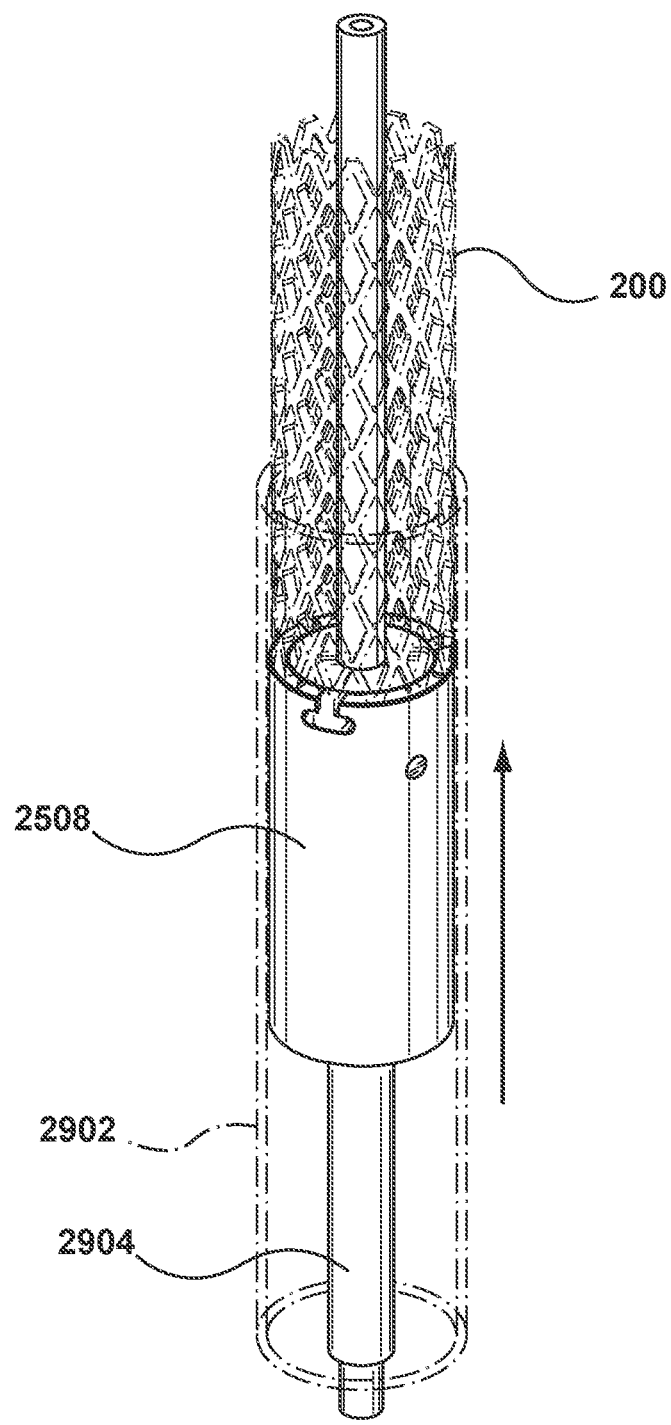
FIG. 34 is a third perspective view of the valve retaining assembly of FIG. 25 with a prosthesis mounted thereto.

Because, as best seen in FIGS. 25-28, the top portion 2803 of blocking member 2502 has a larger diameter than the lower portion of blocking member 2502, the top portion 2803 of blocking member 2502 fits snuggly against the interior opening of retainer slots 2504 when blocking member 2502 is in its fully down position. As a result, when valve retaining assembly 2500 is in the position shown in FIG. 33, fixation hooks 208 within retainer slots 2504 are prevented from escaping to the inside of housing member 2508 by the top portion 2803 of blocking member 2502, while fixation hooks 208 are prevented from exiting the exterior opening of retainer slots 2504 by outer tube 2902. Outer tube 2902 can then be advanced upward over the prosthetic valve 200 as shown in FIG. 34.

Figure 35:
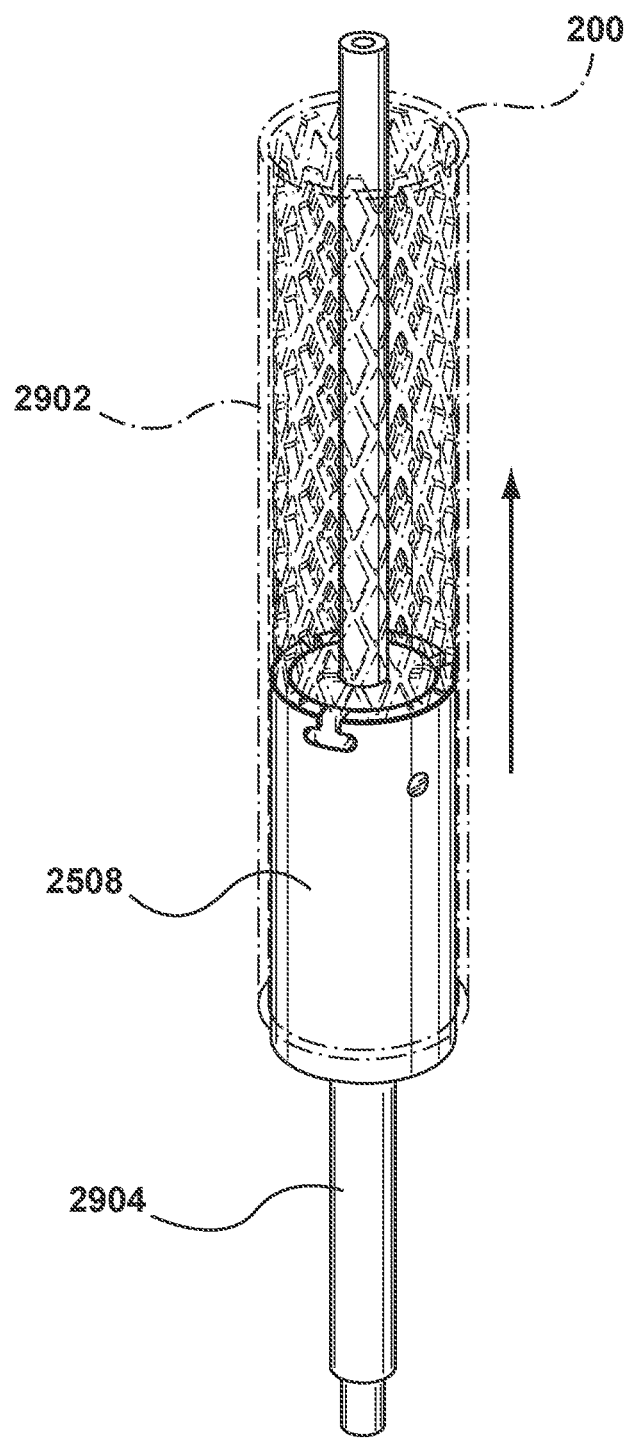
FIG. 35 is a fourth perspective view of the valve retaining assembly of FIG. 25 with a prosthesis mounted thereto.

FIG. 35 depicts valve retaining assembly 2500 with a prosthetic valve 200 mounted thereto with outer tube 2902 fully advanced to entirely cover the prosthetic valve 200. In this configuration, prosthetic valve 200 can be delivered to a desired body location.

Thus, once fixation hooks 208 are positioned within retainer slots 2504, the eyelets are prevented from escaping from the exterior opening of retainer slots 2504 and the interior opening of retainer slots 2504. Specifically, the interior opening of retainer slots 2504 is obstructed by blocking member 2502, and the exterior opening of retainer slots 2504 is obstructed by outer tube 2902. The terms obstruct, obstructed, or obstructing, as used with reference to the various embodiments of the present invention described herein, are intended to mean covering a sufficient amount of an opening so as to prevent fixation hooks 208 or their equivalent from exiting the retainer slots 2504. In one embodiment, outer tube 2902 can be configured similar to sleeve 1602 as described regarding FIG. 16.

Figure 36:
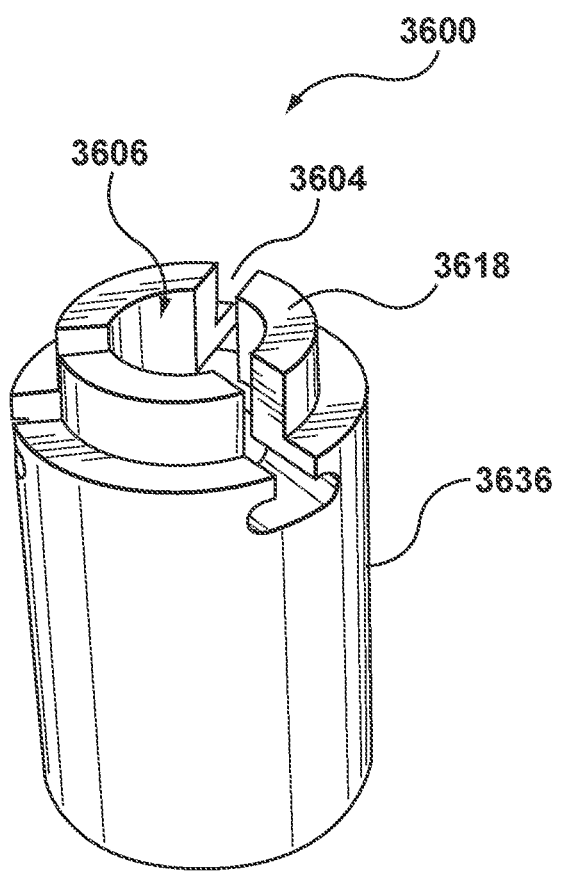
FIG. 36 illustrates a valve retaining assembly according to another embodiment of the present invention.

FIGS. 36-39 illustrate another embodiment of a valve retaining assembly 3600. FIG. 36 illustrates another embodiment of a valve retainer. Valve retainer 3636 can have a central lumen 3606 extends through the center of valve retainer 3636. Three retainer slots 3604 are provided around the upper perimeter of valve retainer 3636. Three upwardly extending walls 3618 are positioned between the retainer slots 3604.

Figure 37:
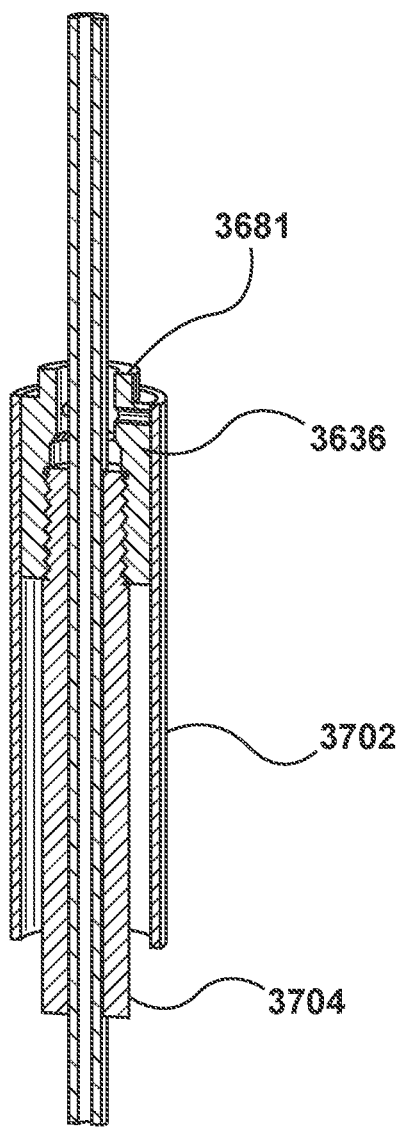
FIG. 37 illustrates a cross-section of the valve retaining assembly of FIG. 36.

FIG. 37 shows valve retainer 3636 at the distal end of a delivery system. As shown in FIG. 37, an outer tube 3702 is positioned around valve retainer 3636. Valve retainer 3636 is secured to a fixation shaft 3704.

Figure 38:
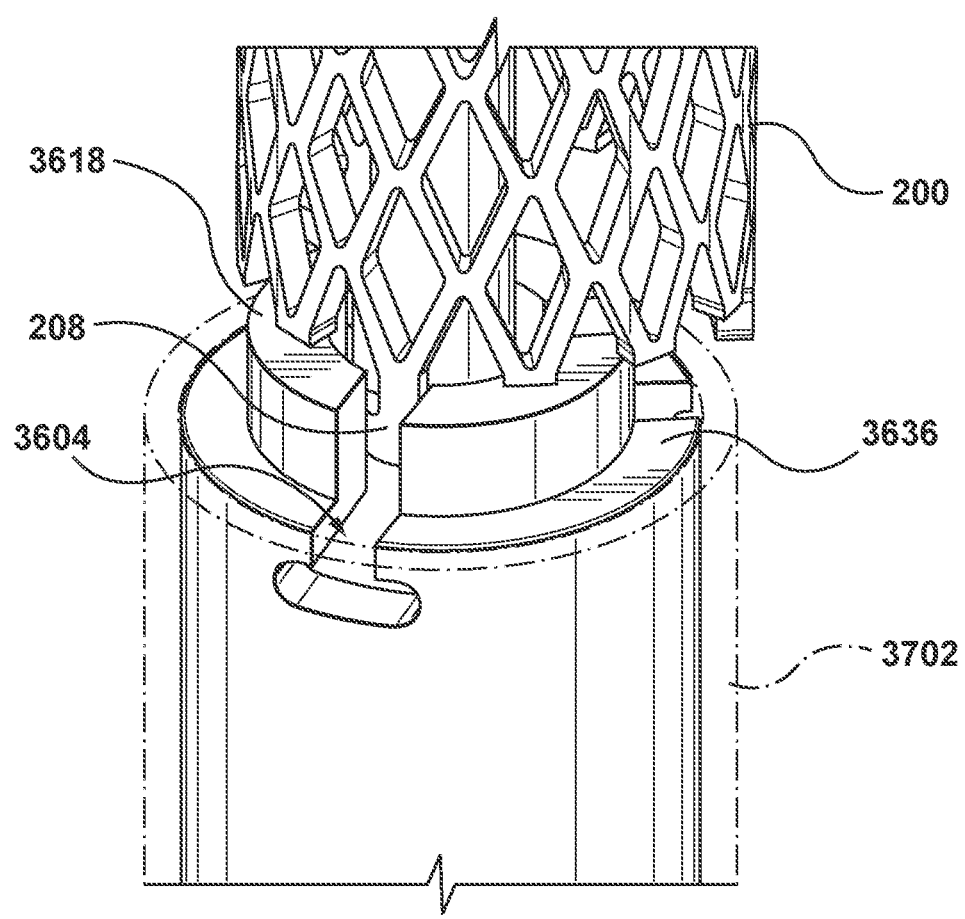
FIG. 38 is a perspective view of the valve retaining assembly of FIG. 36 at one stage of mounting a prosthesis thereto.

FIG. 38 illustrates a method by which a prosthetic valve 200 can be secured within valve retainer 3636. Specifically, a prosthetic valve 200 in its crimped configuration is advanced towards valve retainer 3636. Fixation hooks 208 of prosthetic valve 200 are inserted within lumen 3606 and inside extending walls 3618. The top of outer tube 3702 is flush with the top shoulder 3820 of valve retainer 3636, excluding extending walls 3618. Thus, when fixation hooks are inserted into retainer slots 3604 they are prevented from exiting the outside of retainer slots 3604. In one embodiment, prosthetic valve 200 is pre-biased to an expanded position such that when fixation hooks 208 are inserted into retainer slots 3604 and pressure is released from prosthetic valve 200, the fixation hooks 208 are naturally forced against the outer tube 3702 by the pre-bias of prosthetic valve 200.

Figure 39:
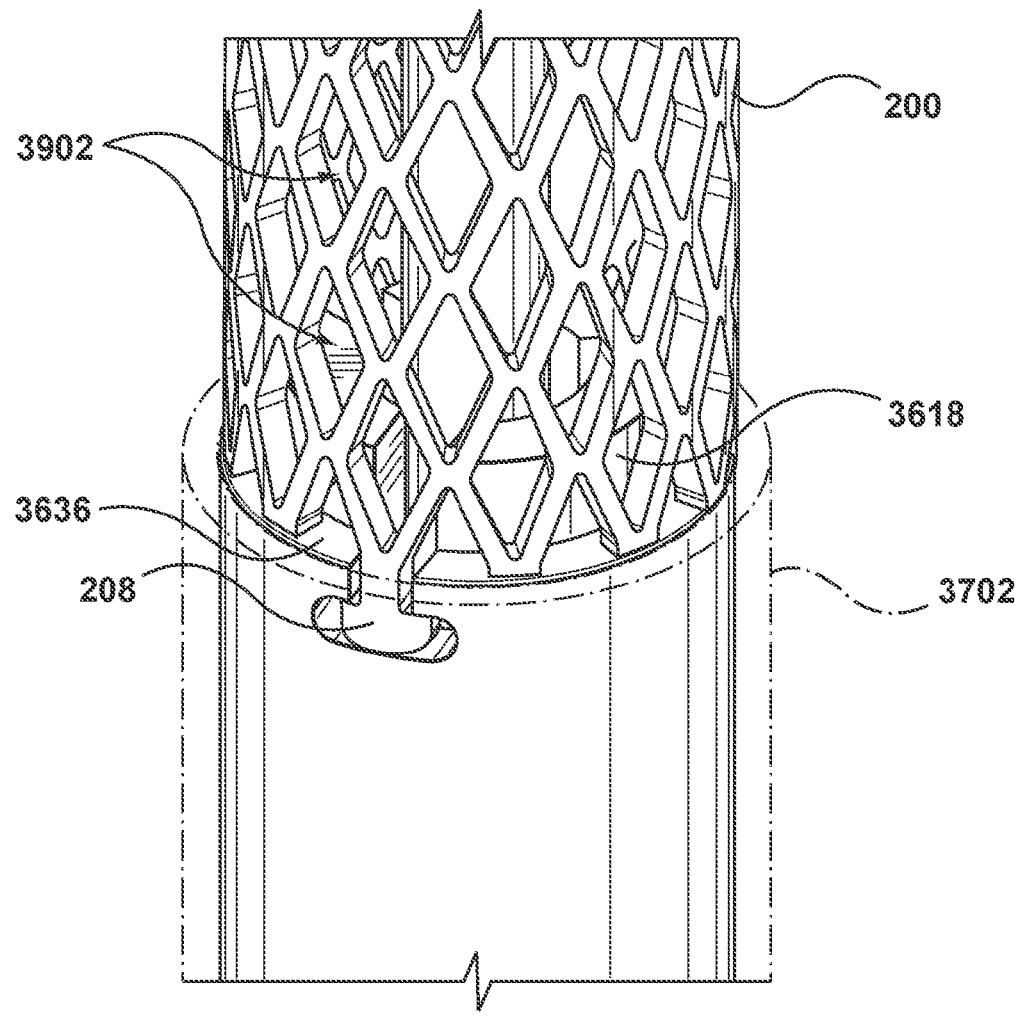
FIG. 39 is a perspective view of the valve retaining assembly of FIG. 36 with a prosthesis mounted thereto.

FIG. 39 illustrates a prosthetic valve 200 fully attached to valve retainer 3636. As shown in FIG. 39, once all fixation hooks 208 are fully placed within retainer slots 3604 the diameter of prosthetic valve 200 is allowed to expand slightly. Because prosthetic valve 200 has a slightly larger diameter in this configuration, the cells 3902 of prosthetic valve 200 are also slightly larger. As a result, when prosthetic valve 200 is in this configuration, cells 3902 can no longer fit through the inside of retainer slot 3604 because of the expansion of the outer perimeter of cells 3902. The outer perimeters of the expanded cells 3902 abut against the extending walls 3618. The fixation hooks 208 are prevented from escaping from the outside of retainer slots 3604 by outer tube 3702. Outer tube 3702 can then be advanced to cover the prosthetic valve 200 completely, and thereafter delivered to a desired body location. After the prosthetic valve 200 is delivered to a desired body location, outer tube 3702 can be slid downward off the prosthetic valve 200, allowing fixation hooks 208 to escape from the outside of retainer slots 3604, and thereby allowing prosthetic valve 200 to deploy in a body lumen to its pre-biased expanded shape. Generally, deployment of the prosthetic valve 200 is achieved in the same manner with the other embodiments of valve retainers and valve retaining assemblies described herein. In one embodiment, outer tube 3702 can be configured similar to sleeve 1602 as described regarding FIG. 16.

Figure 40A:
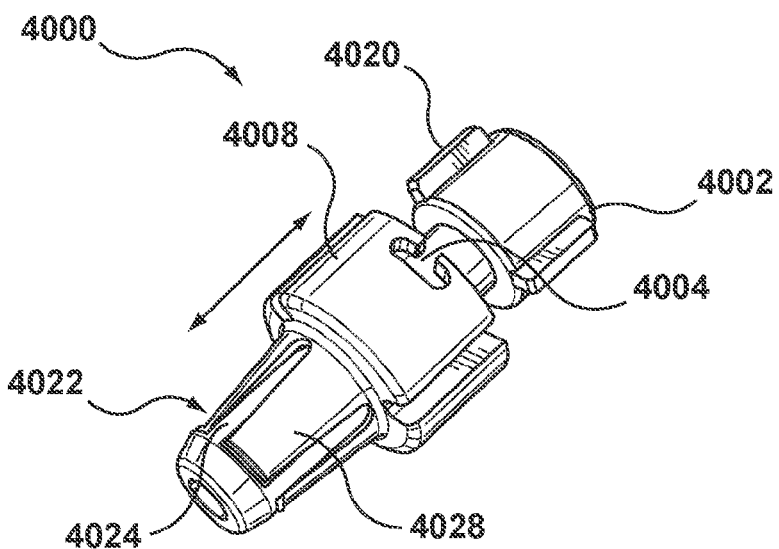
FIG. 40A illustrates a valve retaining assembly according to another embodiment of the present invention.
Figure 40B:
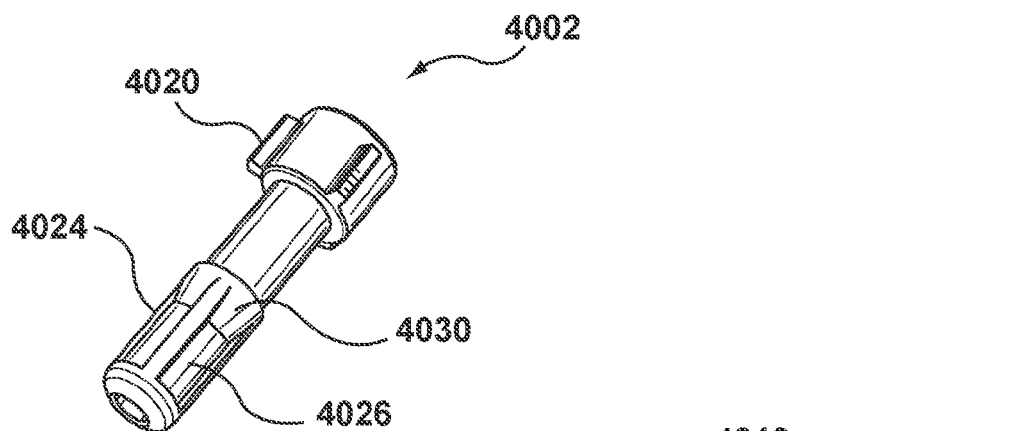
FIG. 40B illustrates a first member of the valve retaining assembly of FIG. 40A.
Figure 40C:
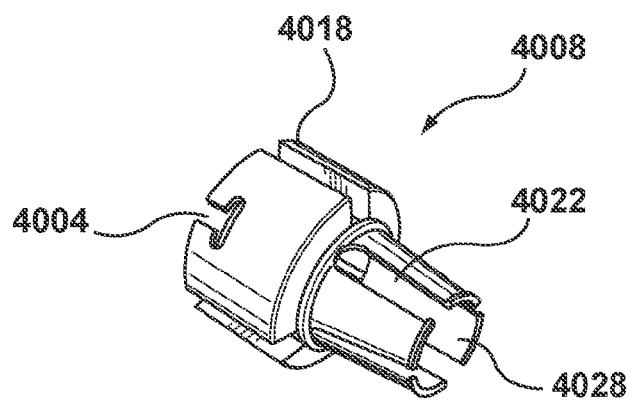
FIG. 40C illustrates a second member of the valve retaining assembly of FIG. 40A.

FIGS. 40A, 40B and 40C illustrate another embodiment of a valve retaining assembly according to the present invention. Valve retaining assembly 4000 includes a blocking member 4002 and a housing member 4008. In one embodiment, blocking member 4002 includes one or more upper tabs 4020, one or more lower tabs 4024, a ridge 4030 approximately mid-way down blocking member 4002, and one or more recesses 4026. In one embodiment, housing member 4008 includes one or more retainer slots 4004, one or more upper channels 4018, one or more lower channels 4022, and one or more flanges 4028. It is understood that the specific number of upper tabs 4020, lower tabs 4024, recesses 4026, upper channels 4018, lower channels 4022, and flanges 4028 can vary in other embodiments of the present invention.

In one embodiment, housing member 4008 can slide over blocking member 4002 until flanges 4028 are even with blocking member recesses 4026. Recesses 4026 are approximately the same size as flanges 4028 so that flanges 4028 fit securely within recesses 4026. In one embodiment, flanges 4028 can be biased inward. Lower tabs 4024 of blocking member 4002 also fit within lower channels 4022 of housing member 4008 to prevent rotation of housing member 4008 relative to blocking member 4002.

Figure 41:
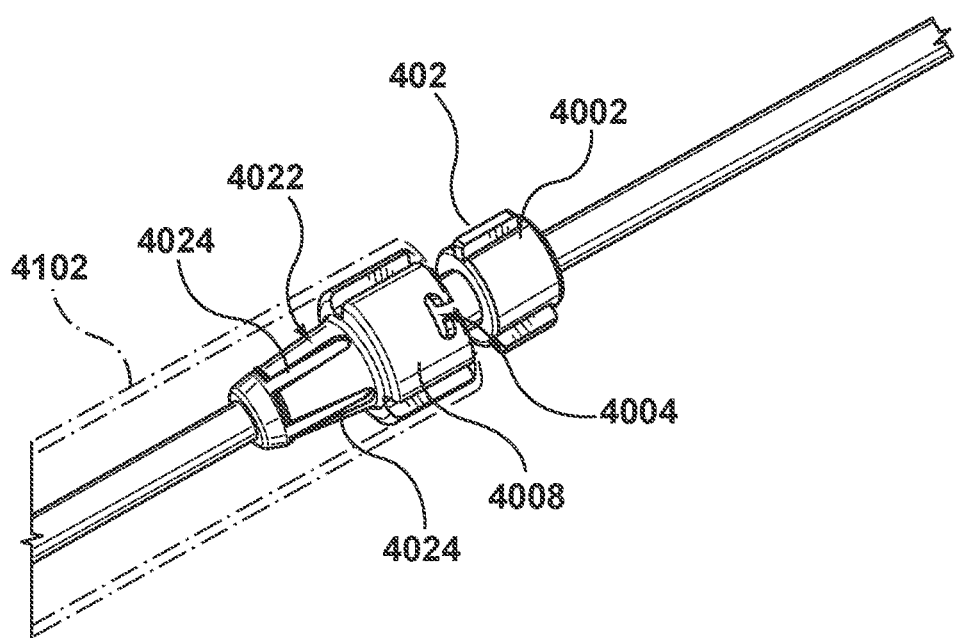
FIG. 41 is a perspective view of the valve retaining assembly of FIG. 40A.
Figure 42:
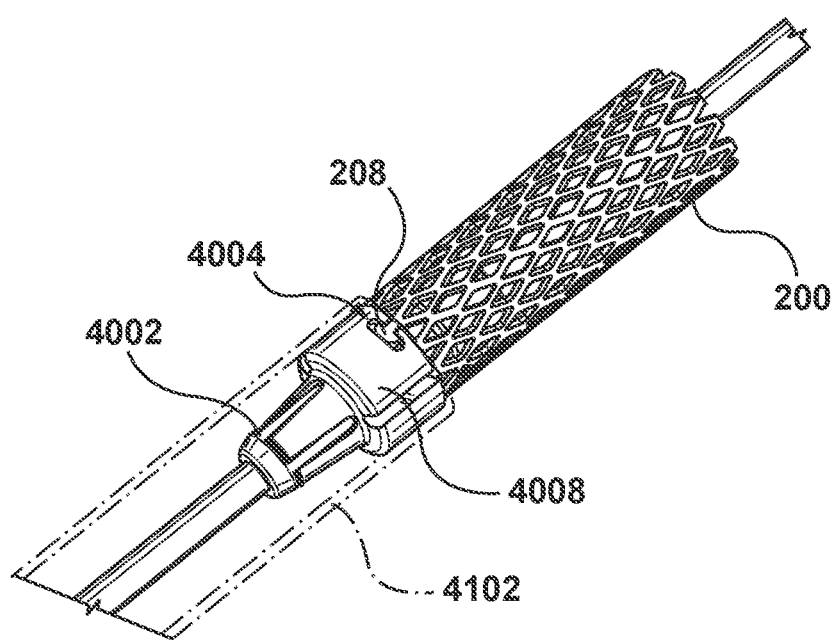
FIG. 42 is a perspective view of the valve retaining assembly of FIG. 40A with a prosthesis mounted thereto.
Figure 43:
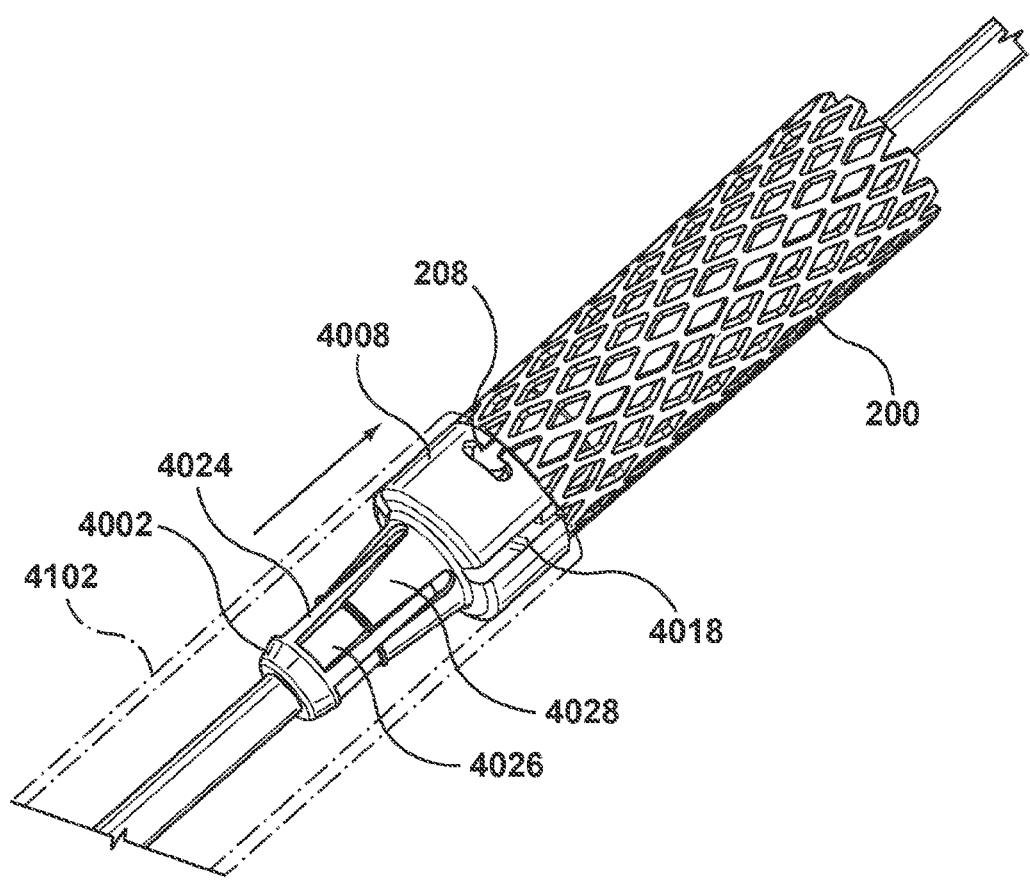
FIG. 43 is another perspective view of the valve retaining assembly of FIG. 40A with a prosthesis mounted thereto.
Figure 44:
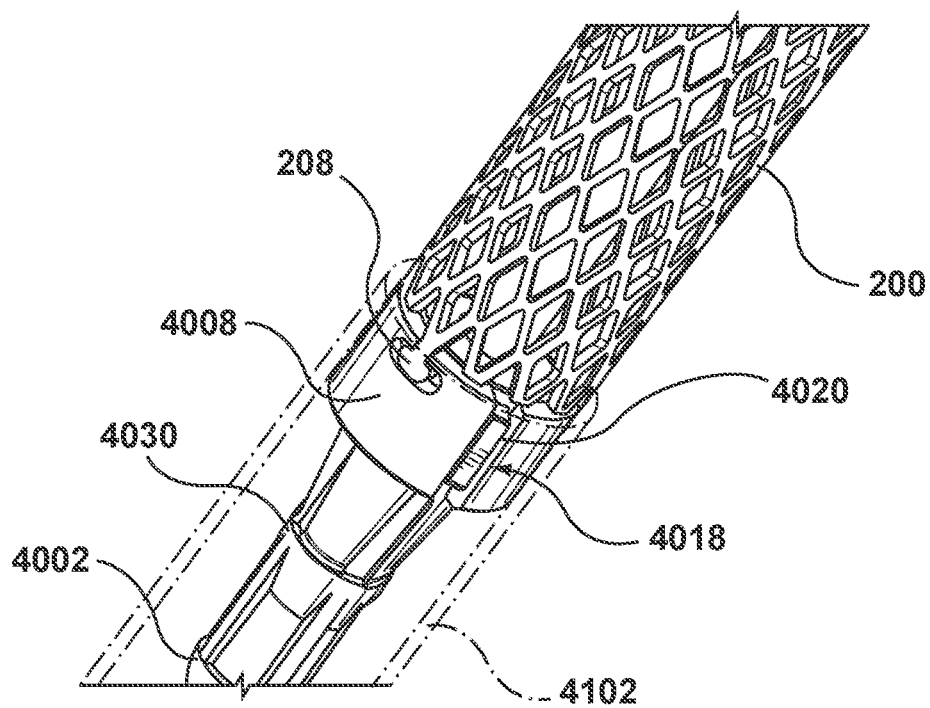
FIG. 44 is a third perspective view of the valve retaining assembly of FIG. 40A with a prosthesis mounted thereto.

FIG. 41 illustrates an outer tube 4102 positioned over valve retaining assembly 4000. Outer tube 4102 covers the outside of valve retainer slots 4004. While the valve retaining assembly 4000 is in this configuration, a prosthetic valve 200 is advanced towards the valve retaining assembly 4000 and fixation hooks 208 are inserted into retainer slots 4004 from the inside of housing member 4008, as shown in FIG. 42. Outer tube 4102 prevents fixation hooks 208 from escaping from the outside of retainer slots 4004. Once fixation hooks 208 are secured within retainer slots 4004, housing member 4008 and outer tube 4102 are simultaneously pushed upward towards prosthetic valve 200. In order to achieve this simultaneous movement pressure must be applied to outer tube 4102 in the area of housing member 4008 to create friction between outer tube 4102 and housing member 4008. As shown in FIGS. 43 and 44, forcing outer tube 4102 and housing member 4008 upward causing flanges 4028 of housing member 4008 to exit from recesses 4026 of blocking member 4002. Housing member 4008 and outer tube 4102 are advanced upwardly along blocking member 4002 until flanges 4028 of housing member 4008 snap into place above ridge 4030 of blocking member 4002. Upper channels 4018 of housing member 4008 receive upper tabs 4020 of blocking member 4002 in order to prevent rotation of blocking member 4002 relative to housing member 4008. Once housing member 4008 is fully advanced over blocking member 4002, fixation hooks 208 are prevented from exiting from the inside of retainer slots 4004 because the inside of retainer slots 4004 abut directly against the upper surface of blocking member 4002. Fixation hooks 208 are prevented from exiting the outside of retainer slots 4004 by outer tube 4102. Outer tube 4102 can then be advanced fully over prosthetic valve 200 for delivery to a desired location in a body. Outer tube 4102 can then be removed to deploy prosthetic valve 200. In one embodiment, outer tube 4102 can be configured similar to sleeve 1602 as described regarding FIG. 16.

Figure 45:
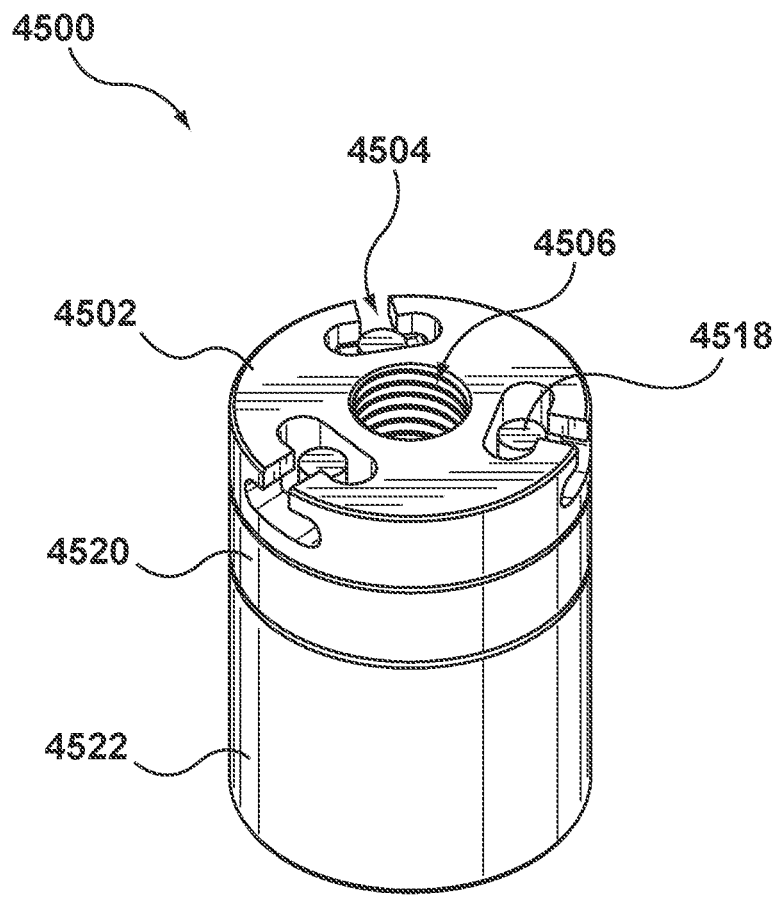
FIG. 45 illustrates a valve retaining assembly according to another embodiment of the present invention.

FIG. 45 illustrates a valve retaining assembly 4500 according to another embodiment of the present invention. Valve retaining assembly 4500 includes a main body 4502 with retainer slots 4504 formed therein. Retracting rods 4518 extend into retainer slots 4504. A central lumen 4506 extends through the center of main body 4502. Valve retaining assembly 4500 also includes a middle ring 4520 and a bottom ring 4522.

Figure 46:
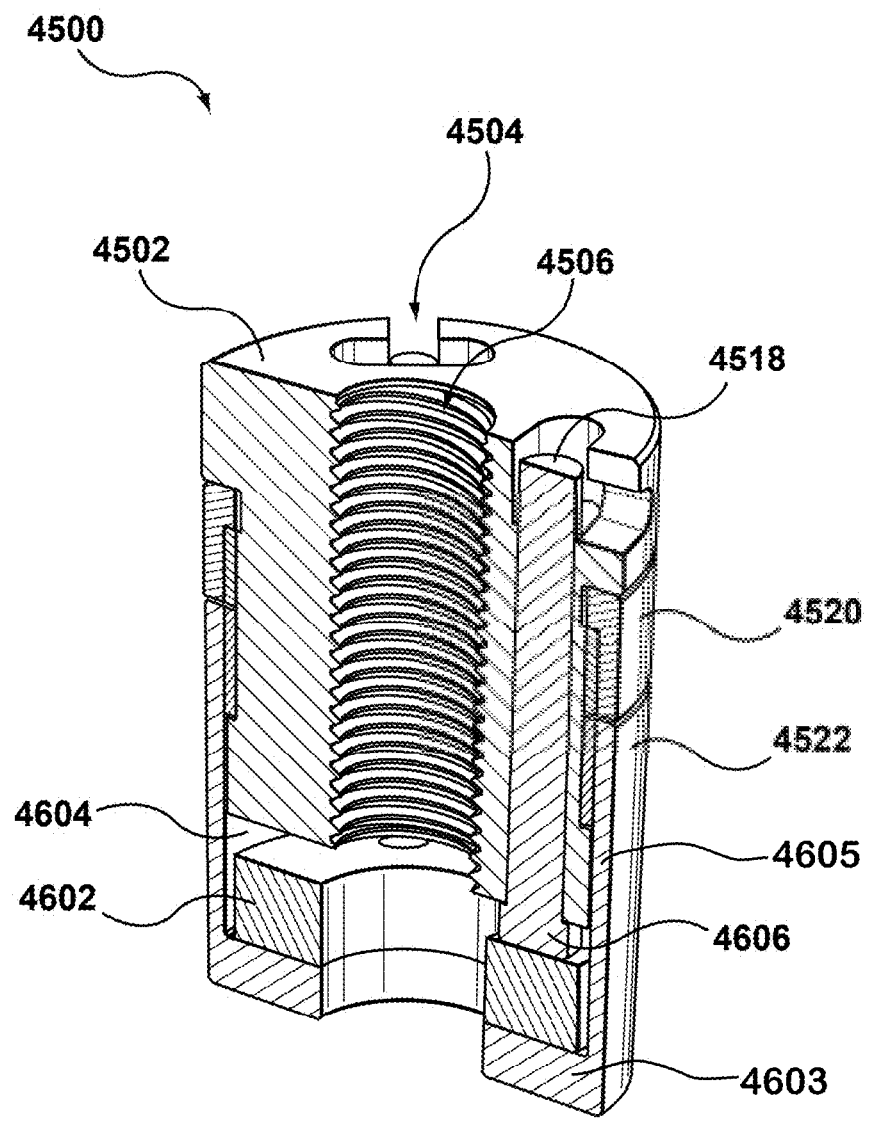
FIG. 46 illustrates a cross-section of the valve retaining assembly of FIG. 45.

FIG. 46 is a cross-section of valve retaining assembly 4500. As shown in FIG. 46, a disk 4602, which is preferably constructed of silicon, is positioned above the bottom surface 4603 of bottom ring 4522 and inside the cylindrical wall 4605 of bottom ring 4522. Main body 4502 extends inside both middle ring 4520 and bottom ring 4522. Bases 4606 of the retracting rods 4518 have a slightly larger diameter than the remainder of retracting rods 4518 such that the bottom of main body 4502 is spaced (shown at 4604) from the top of disk 4602 by the base 4606 of retracting rods 4518. In one embodiment, disk 4602 is compressible and resilient such that it can function as a spring when pressure is applied to the disk 4602. Although disk 4602 is shown, it is understood that other types of springs may be used to pre-bias retracting rods 4518 upwards into the position shown in FIG. 46. For example, a traditional coil spring or a plurality of coil springs can be used. Other types of mechanical springs can also be used. Disk 4602 can be formed of any other suitable, compressible and resilient material.

Figure 47:
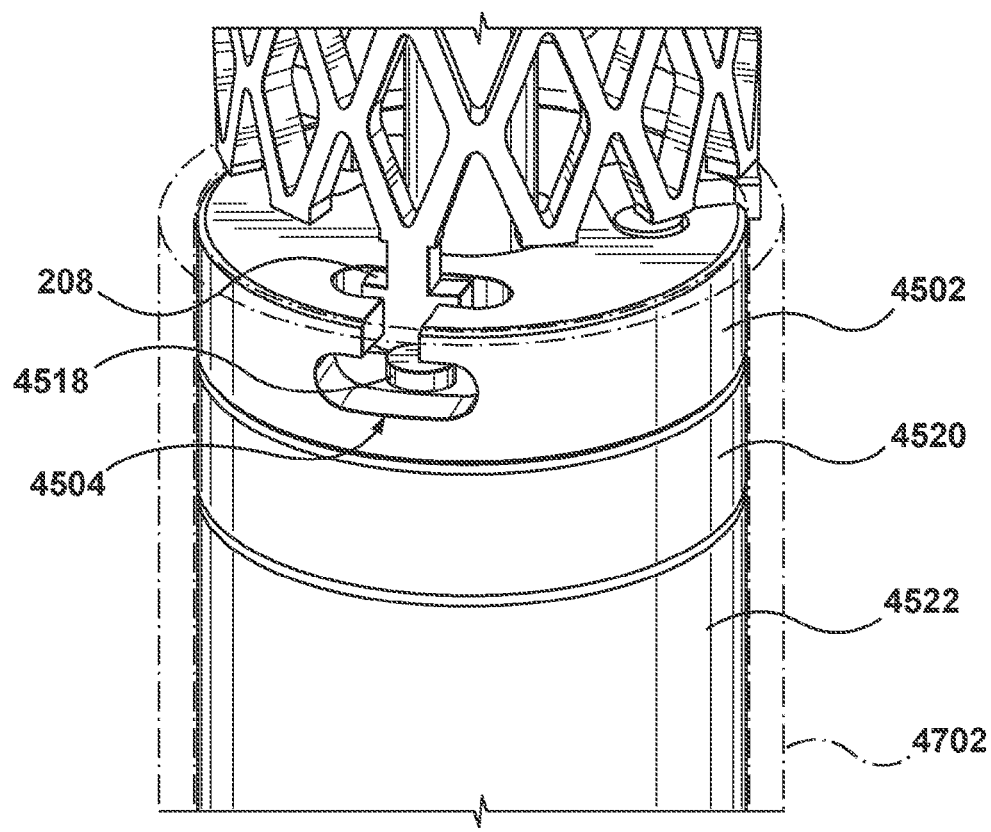
FIG. 47 is a perspective view of the valve retaining assembly of FIG. 45 at one stage of mounting a prosthesis thereto.
Figure 48:
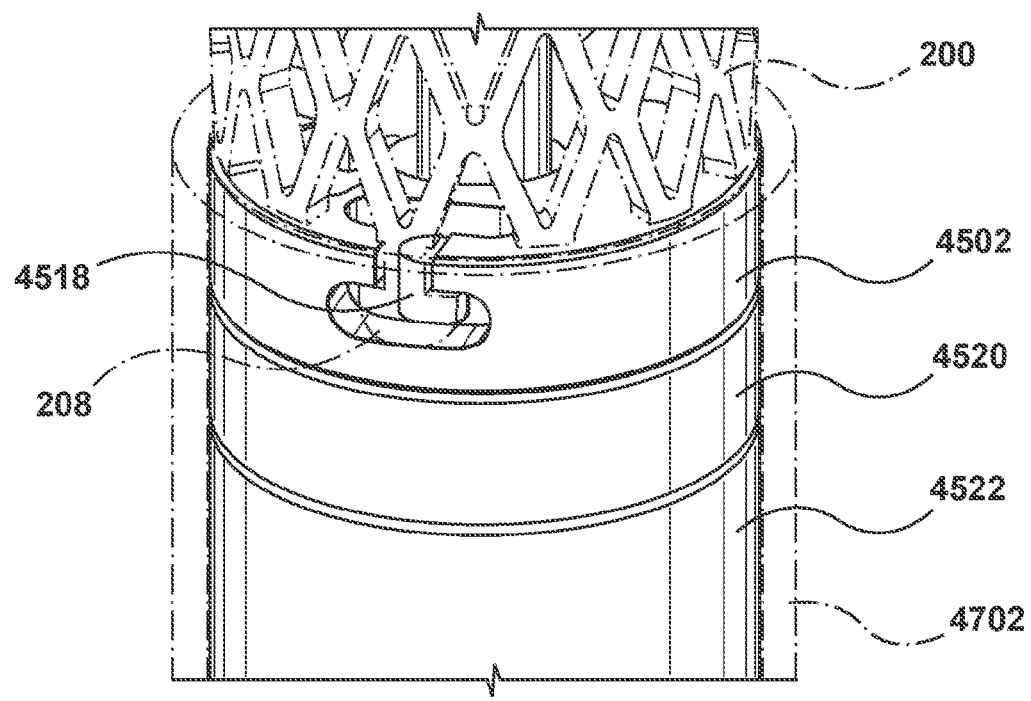
FIG. 48 is a perspective view of the valve retaining assembly of FIG. 45 with a prosthesis mounted thereto.

As shown in FIG. 47, an outer tube 4702 is positioned around main body 4502, middle ring 4520, and bottom ring 4522. To insert prosthetic valve 200 into the valve retaining assembly 4500, fixation hooks 208 are pressed downward against the top of retracting rods 4518. This downward pressure on retracting rods 4518 compresses the disk 4602 which allows the retracting rods 4518 to move out of retainer slots 4504. Fixation hooks 208 can be forced to the bottom of retainer slots 4504, and thereby self-expand into the outside opening of retainer slots 4504 because of the pre-bias of prosthetic valve 200. This configuration is shown in FIG. 48. Because the prosthetic valve 200 is pre-biased into an expanded position, once fixation hooks 208 reach the bottom of retainer slots 4504, fixation hooks 208 naturally expand into the outside opening of retainer slots 4504 and against outer tube 4702. After fixation hooks 208 are positioned against outer tube 4702, retracting rods 4518 return to their original upwardly biased position because there is no longer pressure on top of the retracting rods 4518 to compress disk 4602. Thus, the fixation hooks 208 are prevented from exiting the inside of retainer slots 4504 by the retracting rods 4518. Outer tube 4702 can then be slid completely over prosthetic valve 200 for delivery to a desired body location. Outer tube can then be removed to allow fixation hooks 208 to exit the outside of retainer slots 4504, thereby allowing prosthetic valve to assume its pre-biased expanded configuration. In one embodiment, outer tube 4702 can be configured similar to sleeve 1602 regarding FIG. 16.

Figure 49:
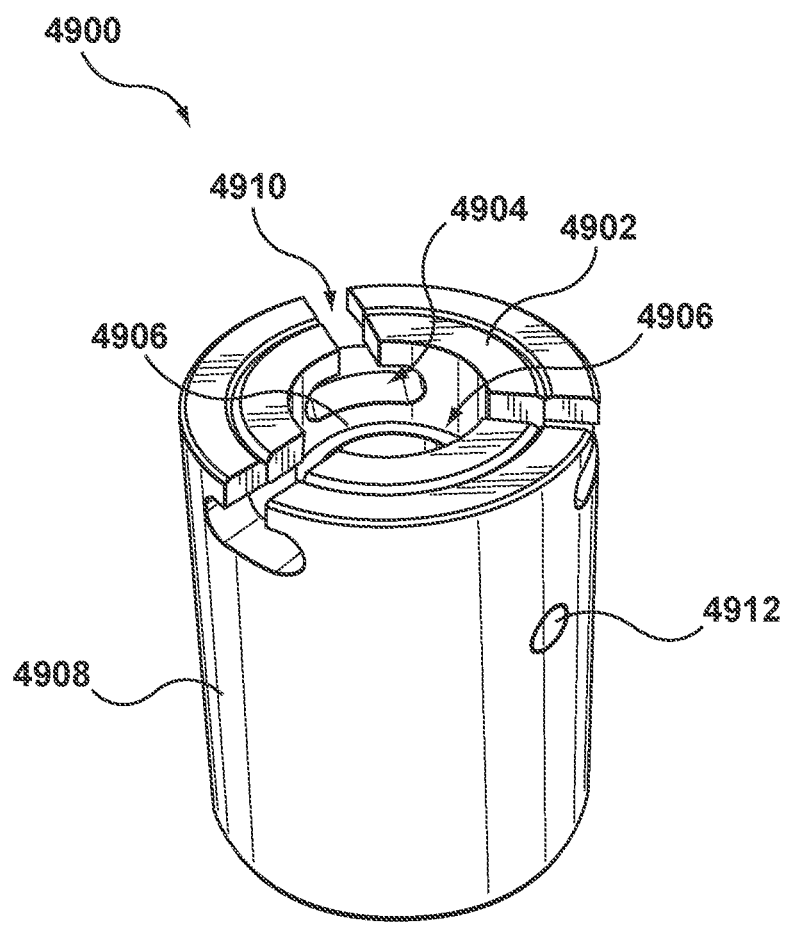
FIG. 49 illustrates a valve retaining assembly according to another embodiment of the present invention.

FIG. 49 depicts another embodiment of a valve retaining assembly according to the present invention. Valve retaining assembly 4900 includes a blocking member 4902 and a housing member 4908. Both blocking member 402 and housing member 4908 have retainer slots. Blocking member retainer slots 4904 are aligned with housing member retainer slots 4910 when valve retaining assembly 4900 is in the configuration show in FIG. 49. A central lumen 4906 extends through the center of blocking member 4902. Guide pins 4912 extend through holes in housing member 4908.

Figure 50:
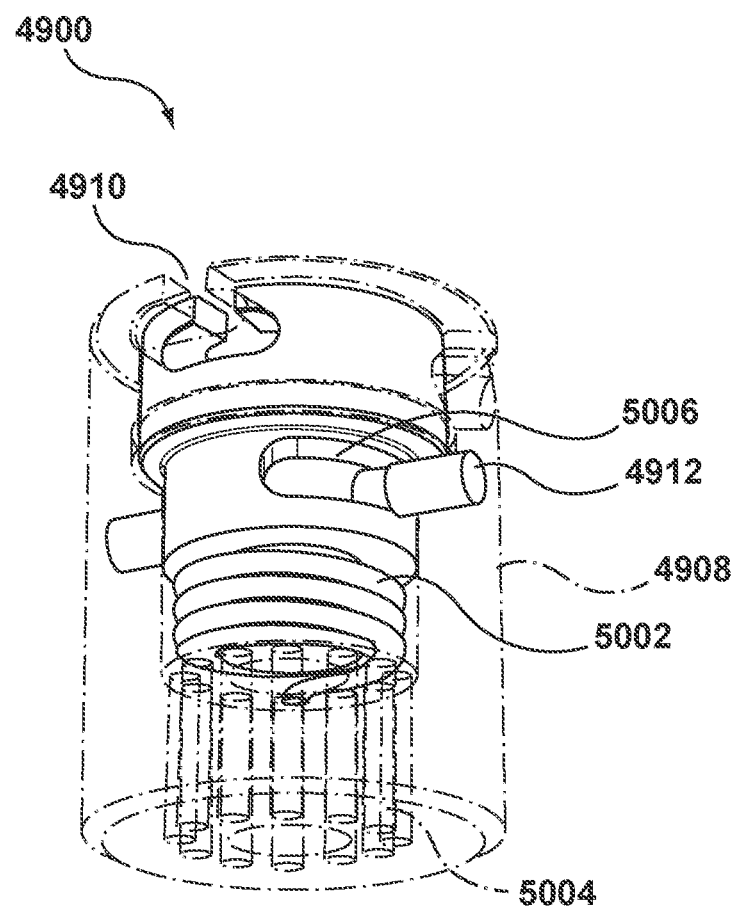
FIG. 50 is an alternate view of the valve retaining assembly of FIG. 49 showing the inside structure of the valve retaining assembly.

FIG. 50 is an inside view of valve retaining assembly 4900 when the housing member 4908 and blocking member 4902 are oriented as shown in FIG. 49. As shown in FIG. 50, valve retaining assembly 4900 includes a torsion spring 5002. A plurality of rods 5004 are positioned under torsion spring 5002 to secure torsion spring 5002 in place relative to housing member 4908. Torsion spring 5002 provides a rotational bias to blocking member 4902 rather than biasing blocking member 4902 up or down relative to housing member 4908. Channels 5006 in blocking member 4902 receive guide pins 4912 therein. The cooperation of guide pins 4912 and channels 5006 limits the range of rotation of blocking member 4902 relative to housing member 4908, and also prevents vertical movement of blocking member 4902 relative to housing member 4908.

Figure 51:
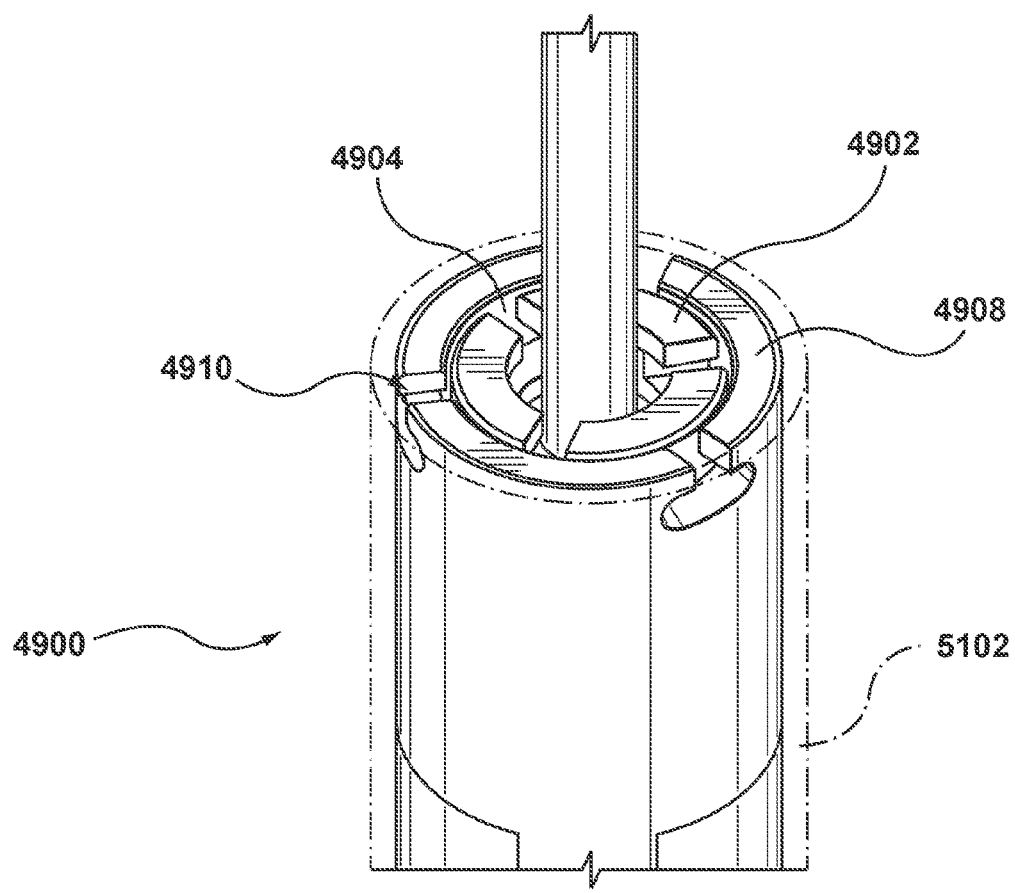
FIG. 51 is a perspective view of the valve retaining assembly of FIG. 49.
Figure 52:
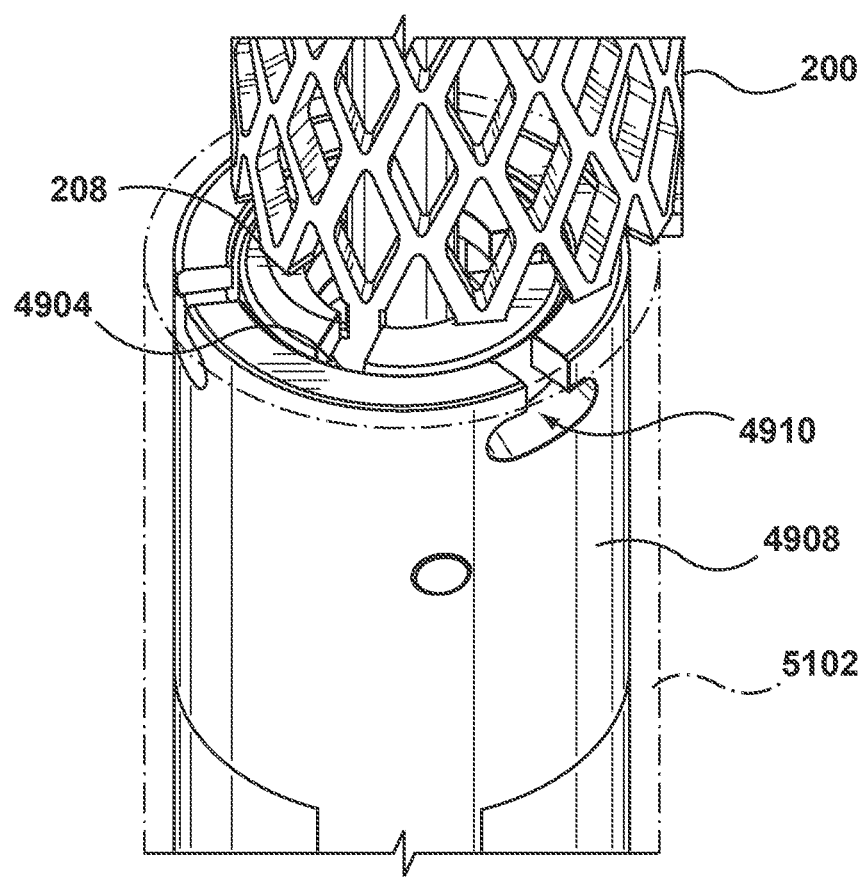
FIG. 52 is a perspective view of the valve retaining assembly of FIG. 49 at one stage of mounting a prosthesis thereto.
Figure 53:
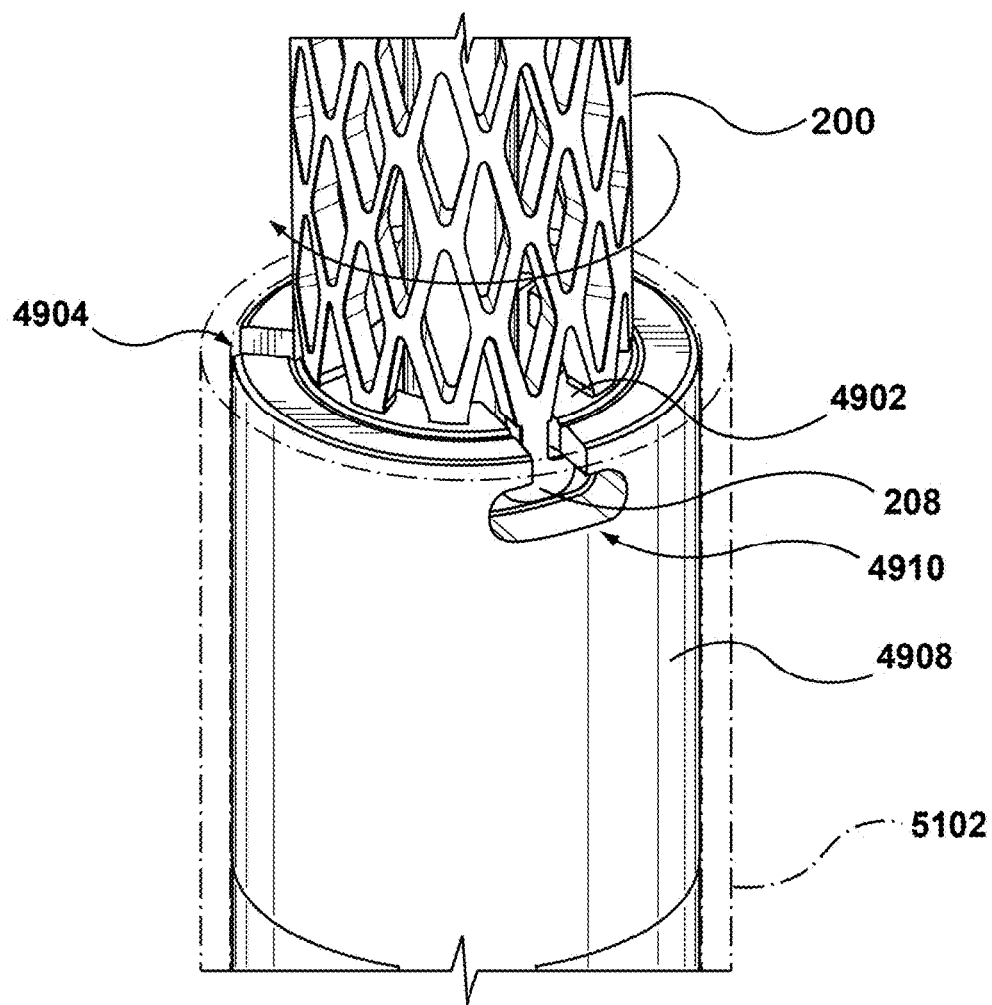
FIG. 53 is a perspective view of the valve retaining assembly of FIG. 49 at another stage of mounting a prosthesis thereto.
Figure 54:
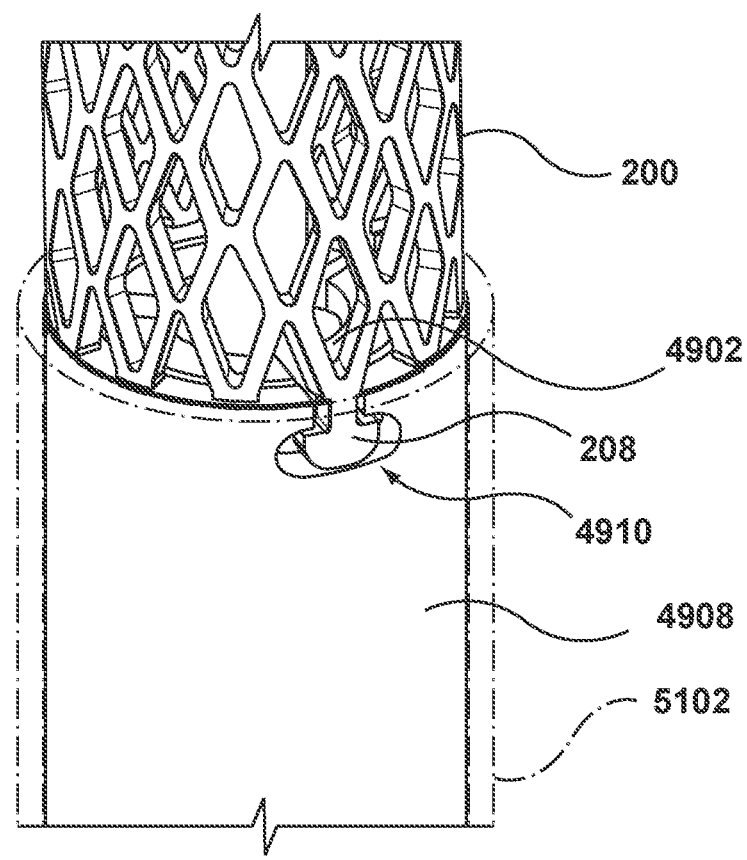
FIG. 54 is a perspective view of the valve retaining assembly of FIG. 49 at another stage of mounting a prosthesis thereto.

FIG. 51 shows valve retaining assembly 4900 in place over a delivery shaft. In the configuration shown in FIG. 51, valve retaining assembly 4900 is in a first position. An outer tube 5102 is positioned around housing member 4908. As shown in FIG. 51, blocking member 4902 has been rotated with respect to housing member 4908 such that blocking member retainer slots 4904 are not aligned with housing member retainer slots 4910. Torsion spring 5002 biases blocking member in this position. Outer tube 5102 covers the outside of housing member retainer slots 4910. While valve retaining assembly 4900 is in this configuration, the prosthetic valve 200 is advanced towards valve retaining assembly 4900 and fixation hooks 208 of prosthetic valve 200 are inserted into the blocking member retainer slots 4904 from the inside of blocking member 4902. After all fixation hooks 208 have been inserted into a blocking member retainer slot 4904, the user can rotate prosthetic valve 200 against the biasing force of torsion spring 5002 in order to bring blocking member retainer slots 4904 into alignment with housing member retainer slots 4910. Because prosthetic valve 200 is biased in an expanded position, once blocking member retainer slots 4904 are aligned with housing member retainer slots 410, fixation hooks 208 will pop out into housing member retainer slots 4910 until they press against outer tube 5102. In addition, because torsion spring 5002 biases the rotation of blocking member 4902 compared with housing member 4908 to the first position (shown in FIG. 51), when fixation hooks 208 exit blocking member retainer slots 4904, blocking member 4902 is pulled back to the first position by torsion spring 5002. That is, because of the natural bias of torsion spring 5002, torsion spring 5002 rotates blocking member 4902 back to a position wherein the blocking member retainer slots 4904 are not aligned with housing member retainer slots 4910. Fixation hooks 208 are thereby prevented from exiting the inside of housing member retainer slots 4910 by the walls of blocking member 4902 and fixation hooks 208 are prevented from exiting the outside of housing member retainer slots 4910 by outer tube 5102. With reference to FIG. 50, the interaction of channels 5006 and guide pins 4912 limits the range of rotation of blocking member 4902 such that over rotation is not allowed. After fixation hooks 208 are secured within housing member retainer slots 4910 and blocking member 4902 has rotated back to its original starting position, outer tube 5102 can be advanced over prosthetic valve 200 and valve 200 can be delivered to a desired body location. Outer tube can then be removed to allow fixation hooks 208 to exit the outside of retainer slots 4504, thereby allowing prosthetic valve to assume its pre-biased expanded configuration. In one embodiment, outer tube 5102 can be configured similar to sleeve 1602 in FIG. 16.

Preferably, the entire process, including securing a valve assembly to a loading ring or valve retainer, crimping the valve assembly, removing the crimping accessories from the catheter assembly, and moving the catheter assembly 100 to its closed configuration, is performed in a saline bath by a user.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

EXAMPLES

The following paragraphs serve as examples of the above-described embodiments.

Example 1

One embodiment of the present invention provides a prosthesis retaining assembly for securing an implantable prosthesis to a catheter assembly. The prosthesis retaining assembly comprises a blocking member having a central lumen and a housing member connected to the blocking member. A plurality of prosthesis retaining slots is formed in the housing member. The blocking member is positioned inside the housing member and the blocking member is movable relative to the housing member. The prosthesis retaining slots are configured to retain a portion of a prosthesis therein.

The prosthesis retaining assembly can include an outer tube surrounding the housing member. The prosthesis retaining assembly can include a biasing member connected to the blocking member and the housing member, wherein the biasing member biases the blocking member to a first position relative to the housing member. The housing member can have a bottom surface and a top surface. The biasing member can bias the blocking member away from the bottom surface of the housing member. The biasing spring can be configured to rotationally bias the blocking member to a first position relative to the housing member. The housing member can include an exterior surface and an interior surface, wherein the prosthesis retaining slots have an exterior opening opened to the exterior surface of the housing member and an interior opening opened to the interior surface of the housing member. The blocking member can be configured to be movable between a first position wherein the blocking member does not obstruct the interior opening of the prosthesis retaining slots and a second position wherein the blocking member obstructs the interior opening of the prosthesis retaining slots. The outer tube can obstruct the exterior opening of the prosthesis retaining slots.

Example 2

Another embodiment of the present invention provides a prosthesis retaining assembly for securing an implantable prosthesis to a catheter assembly. The prosthesis retaining assembly includes a valve retainer having a central lumen, the valve retainer having a top surface and a bottom surface, wherein prosthesis retaining slots are formed in the top surface. The prosthesis retaining assembly further includes a plurality of walls extending from the top surface of the valve retainer, the spaces between the walls defining channels that are open to the prosthesis retaining slots. The prosthesis retaining assembly further includes an outer tube, wherein the valve retainer is positioned inside the outer tube. The prosthesis retaining slots are configured to retain a portion of a prosthesis therein.

The valve retainer can include an exterior surface and an interior surface, and the prosthesis retaining slots can have an exterior opening opened to the exterior surface of the valve retainer and an interior opening opened to the interior surface of the valve retainer. The channels defined by the walls can be configured to prevent a retained portion of a prosthesis from exiting the interior opening of the prosthesis retaining slots. The outer tube can be slidable with respect to the valve retainer. The outer tube can be configured to assume a first position that obstructs the exterior opening of the valve retainer.

Example 3

Another embodiment of the present invention provides a prosthesis retaining assembly for securing an implantable prosthesis to a catheter assembly. The prosthesis retaining assembly includes a blocking member having a central lumen therethrough and a housing member connected to the blocking member, wherein a plurality of prosthesis retaining slots are formed in the housing member. The prosthesis retaining assembly further includes a plurality of retaining rods and a biasing member, wherein the biasing member is configured to bias the retaining rods to a first position corresponding to the position of the prosthesis retaining slots. The blocking member is positioned at least partially inside the housing member. The prosthesis retaining slots are configured to retain a portion of a prosthesis therein.

The retaining rods can include a base, and wherein the base of the retaining rods can space the blocking member away from the biasing member. The blocking member can include an outer surface and an interior surface, and wherein the prosthesis retaining slots have an exterior opening opened to the exterior surface of the blocking member and an interior opening opened to the interior surface of the blocking member. When the retaining rods are in the first position, the retaining rods can obstruct the interior opening of the prosthesis retaining slots. The retaining rods can be configured to be movable to a second position that does not obstruct the interior opening of the prosthesis retaining slots. The biasing member can include a silicon disk. The biasing member can include a spring.

What is claimed is:

1. A prosthesis retaining assembly for securing an implantable prosthesis to a catheter assembly, the prosthesis retaining assembly comprising:
   a first member including,
      a central longitudinal axis,
      a central lumen,
      a first end surface,
      a longitudinal passage radially offset from the central lumen, the longitudinal passage extending to the first end surface,
      a prosthesis retaining slot configured to retain a portion of the prosthesis, the retaining slot being configured to retain a portion of the prosthesis such that when the portion of the prosthesis is retained within the retaining slot longitudinal movement of the prosthesis relative to the first member is prevented, the retaining slot having an inner opening intersecting with the longitudinal passage and an outer opening intersecting with an outer surface of the first member; and
   a second member positioned within the longitudinal passage of the first member, the second member being movable relative to the first member between
      a first position at which a portion of the second member is positioned adjacent to and obstructs a portion of the inner opening of the retaining slot preventing the portion of the prosthesis retained within the retaining slot from exiting the inner opening of the retaining slot in a radially inward direction towards the central longitudinal axis, and
      a second position at which the portion of the second member is moved relative to the retaining slot such that the portion of the prosthesis can pass through the inner opening of the retaining slot in a radially outward direction away from the central longitudinal axis.

2. The prosthesis retaining assembly of claim 1, wherein the second member is a rod.

3. The prosthesis retaining assembly of claim 2, further comprising:
   a ring, a portion of the ring being disposed around a portion of the outer surface of the first member, the ring including a lip extending radially inward such that the second member is disposed between the lip of the ring and the first end surface of the first member.

4. The prosthesis retaining assembly of claim 3, wherein the longitudinal passage includes a second opening at a second end surface of the first member, wherein the second member extends through the second opening, and wherein the second end surface of the first member is disposed longitudinally between the lip of the ring and the first end surface of the first member.

5. The prosthesis retaining assembly of claim 4, wherein the portion of the second member is a first end portion of the second member, and wherein a second end portion of the second member opposite the first end portion extends out of the second opening of the longitudinal passage.

6. The prosthesis retaining assembly of claim 5, wherein the second end portion of the second member has a larger cross-sectional profile than the second opening of the longitudinal passage such that the second end portion of the second member is prevented from entering the longitudinal passage through the second opening of the longitudinal passage.

7. The prosthesis retaining assembly of claim 6, further comprising a biasing member disposed between the second end of the second member and the lip of the ring, wherein biasing member biases the second member to the first position.

8. The prosthesis retaining assembly of claim 7, wherein the biasing member is a disk, wherein the disk is compressible and resilient.

9. The prosthesis retaining assembly of claim 7, wherein the biasing member is a spring.

10. The prosthesis retaining assembly of claim 2, wherein the second member is biased to the first position.

11. The prosthesis retaining assembly of claim 10,
   wherein the prosthesis retaining assembly is configured such that with the second member in the first position, the portion of prosthesis may be inserted into the longitudinal passage at the first end surface of the first member, and
   wherein pressure applied by the portion of the prosthesis against the second member overcomes the bias to move the second member towards the second position until the second member does not obstruct the inner opening of the retaining slot, thereby permitting the portion of the prosthesis to expand radially outward through the inner opening of the retaining slot and into the retaining slot.

12. The prosthesis retaining assembly of claim 11, further comprising an outer tube disposed radially around the first member, wherein the outer tube includes a first position blocking the outer opening of the retaining slot, thereby preventing the portion of the prosthesis from exiting the outer opening of the retaining slot.

13. The prosthesis retaining assembly of claim 12, wherein the outer tube is configured to be moved to a second position wherein the outer tube does not block the outer opening of the retainer slot, thereby enabling the portion of the prosthesis to self-expand radially outward through the outer opening during deployment of the prosthesis.

* * * * *